(12) United States Patent
Stevenson

(10) Patent No.: US 7,765,005 B2
(45) Date of Patent: Jul. 27, 2010

(54) APPARATUS AND PROCESS FOR REDUCING THE SUSCEPTABILITY OF ACTIVE IMPLANTABLE MEDICAL DEVICES TO MEDICAL PROCEDURES SUCH AS MAGNETIC RESONANCE IMAGING

(75) Inventor: Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 1477 days.

(21) Appl. No.: 11/097,999

(22) Filed: Mar. 31, 2005

(65) Prior Publication Data

US 2005/0197677 A1 Sep. 8, 2005

Related U.S. Application Data

(63) Continuation-in-part of application No. 10/825,900, filed on Apr. 15, 2004, now Pat. No. 6,999,818, and a continuation-in-part of application No. 10/842,967, filed on May 10, 2004, now Pat. No. 7,038,900, and a continuation-in-part of application No. 10/778,954, filed on Feb. 12, 2004, now Pat. No. 6,985,347.

(60) Provisional application No. 60/607,276, filed on Sep. 2, 2004.

(51) Int. Cl.
*A61N 1/375* (2006.01)

(52) U.S. Cl. ............ 607/37; 607/2; 607/3; 607/4; 607/5; 607/36; 429/180; 429/181; 429/182; 429/183; 429/184

(58) Field of Classification Search ............ 607/37; 429/180–189
See application file for complete search history.

(56) References Cited

U.S. PATENT DOCUMENTS

| | | | |
|---|---|---|---|
| 2,756,375 A | 7/1956 | Peck | |
| 3,235,939 A | 2/1966 | Rodriguez et al. | |
| 3,266,121 A | 8/1966 | Rayburn | |
| 3,538,464 A | 11/1970 | Walsh | |
| 3,617,830 A | 11/1971 | Perna, Jr. | |
| 3,881,493 A | 5/1975 | Cannon | |
| 3,920,888 A | 11/1975 | Barr | |

(Continued)

OTHER PUBLICATIONS

C. Gabriel et al.; The Dielectric Properties of Biological Tissues: I. Literature Survey; Phys. Med. Biol. 41 (1996), 2231-2249; IOP Publishing Ltd., UK.

(Continued)

*Primary Examiner*—Carl H Layno
*Assistant Examiner*—Paula J Stice
(74) *Attorney, Agent, or Firm*—Kelly Lowry & Kelley, LLP

(57) ABSTRACT

A feedthrough terminal assembly for an active implantable medical device (AIMD) includes a plurality of leadwires extending from electronic circuitry of the AIMD, and a lossy ferrite inductor through which the leadwires extend in nonconductive relation for increasing the impedance of the leadwires at selected RF frequencies and reducing magnetic flux core saturation of the lossy ferrite inductor through phase cancellation of signals carried by the leadwires. A process is also provided for filtering electromagnetic interference (EMI) in an implanted leadwire extending from an AIMD into body fluids or tissue, wherein the leadwire is subjected to occasional high-power electromagnetic fields such as those produced by medical diagnostic equipment including magnetic resonance imaging.

80 Claims, 66 Drawing Sheets

U.S. PATENT DOCUMENTS

| | | | |
|---|---|---|---|
| 4,038,990 | A | 8/1977 | Thompson |
| 4,041,587 | A | 8/1977 | Kraus |
| 4,083,022 | A | 4/1978 | Nijman |
| 4,144,509 | A | 3/1979 | Boutros |
| 4,148,003 | A | 4/1979 | Colburn et al. |
| 4,152,540 | A | 5/1979 | Duncan et al. |
| 4,220,813 | A | 9/1980 | Kyle |
| 4,247,881 | A | 1/1981 | Coleman |
| 4,248,237 | A | 2/1981 | Kenny |
| 4,254,775 | A | 3/1981 | Langer |
| 4,314,213 | A | 2/1982 | Wakino |
| 4,352,951 | A | 10/1982 | Kyle |
| 4,362,792 | A | 12/1982 | Bowsky et al. |
| 4,421,947 | A | 12/1983 | Kyle |
| 4,424,551 | A | 1/1984 | Stevenson et al. |
| 4,436,093 | A | 3/1984 | Belt |
| 4,456,786 | A | 6/1984 | Kyle |
| 4,500,159 | A | 2/1985 | Briones et al. |
| 4,737,601 | A | 4/1988 | Gartzke |
| 4,741,710 | A | 5/1988 | Hogan et al. |
| 4,853,824 | A | 8/1989 | Tsuzurahara |
| 4,887,609 | A | 12/1989 | Cole, Jr. |
| 4,899,760 | A | 2/1990 | Jaeb et al. |
| 4,951,672 | A | 8/1990 | Buchwald et al. |
| 4,952,357 | A * | 8/1990 | Euteneuer .................. 264/129 |
| 4,991,580 | A | 2/1991 | Moore |
| 5,032,692 | A | 7/1991 | DeVolder |
| 5,070,605 | A | 12/1991 | Daglow et al. |
| 5,142,430 | A | 8/1992 | Anthony |
| 5,217,010 | A | 6/1993 | Tsitlik et al. |
| 5,333,095 | A | 7/1994 | Stevenson et al. |
| 5,406,444 | A | 4/1995 | Selfried |
| 5,440,447 | A | 8/1995 | Shipman et al. |
| 5,531,003 | A | 7/1996 | Seifried et al. |
| 5,539,611 | A | 7/1996 | Hegner et al. |
| 5,540,959 | A | 7/1996 | Wang |
| 5,620,476 | A | 4/1997 | Truex et al. |
| 5,650,759 | A | 7/1997 | Hittman et al. |
| 5,670,063 | A | 9/1997 | Hegner et al. |
| 5,735,884 | A | 4/1998 | Thompson et al. |
| 5,751,539 | A | 5/1998 | Stevenson et al. |
| 5,759,197 | A | 6/1998 | Sawchuk et al. |
| 5,825,608 | A | 10/1998 | Duva et al. |
| 5,827,997 | A | 10/1998 | Chung et al. |
| 5,905,627 | A | 5/1999 | Brendel et al. |
| 5,973,906 | A | 10/1999 | Stevenson et al. |
| 6,008,980 | A | 12/1999 | Stevenson et al. |
| 6,349,025 | B1 | 2/2002 | Fraley et al. |
| 6,506,972 | B1 | 1/2003 | Wang |
| 6,529,103 | B1 * | 3/2003 | Brendel et al. .............. 333/182 |
| 6,673,999 | B1 | 1/2004 | Wang et al. |
| 6,713,671 | B1 | 3/2004 | Wang et al. |
| 6,760,628 | B2 | 7/2004 | Weiner et al. |
| 6,765,144 | B1 | 7/2004 | Wang et al. |
| 6,768,053 | B1 | 7/2004 | Wang et al. |
| 6,778,856 | B2 | 8/2004 | Connelly et al. |
| 6,815,609 | B1 | 11/2004 | Wang et al. |
| 6,819,958 | B2 | 11/2004 | Weiner et al. |
| 2002/0165588 | A1 * | 11/2002 | Fraley et al. .................. 607/37 |

OTHER PUBLICATIONS

S. Gabriel et al.; The Dielectric Properties of Biological Tissues: II. Measurements in the Frequency Range 10 Hz to 20 GHz; Phys. Med. Biol. 41 (1996), 2251-2269; IOP Pub.UK.

S. Gabriel et al.; The Dielectric Properties of Biological Tissues: III. Parametric Models for the Dielectric Spectrum of Tissues; Phys. Med. Biol. 41 (1996), 2271-2293; IOP Publishing, UK.

Frank G. Shellock, PhD.; Biomedical Implants and Devices: Assessment of Magnetic Field Interactions With a 3.0-Tesla MR System; Journal of Magnetic Resonance Imaging 16:721-732 (2002); published online in Wiley InterScience, USA.

Dewinder S. Bhachu, MSc and Emanuel Kanal, MD; Implantable Pulse Generators (Pacemakers) and electrodes: Safety in the Magnetic Resonance Imaging Scanner Environment Journal of Magnetic Resonance Imaging 12:201-204 (2000); Crown copyright 2000, UK.

Beth A. Schueler, PhD. et al.; MRI Compatibility and Visibility Assessment of Implantable Medical Devices; Journal of Magnetic Resonance Imaging 9:596-603 (1999); USA.

Christian Teissl, MS et al.; Magnetic Resonance Imaging and Cochlear Implants: Compatibility and Safety Aspects; Journal of Magnetic Resonance Imaging 9:26-38 (1999); Austria.

Frank G. Shellock, PhD.; Magnetic Resonance Safety Update 2002: Implants and Devices; Journal of Magnetic Resonance Imaging 16:485-496 (2002) published online in Wiley InterScience; USA.

Wes Clement et al.; Estimation of Effective Lead Loop Area for Implantable Pulse Generators and Implantable Cardioverter Defibrillators; AAMI Pacemaker EMC Task Force; Apr. 12, 2004; pp. 1-10; USA.

Wilson Greatbatch, PE, FACC et al.; Magnetic Resonance Safety Testing of a Newly-Developed Fiber-Optic Cardiac Pacing Lead; Journal of Magnetic Resonance Imaging 16:97-103 (2002); published online in Wiley InterScience; USA.

Roger Christoph Luchinger; Safety Aspects of Cardiac Pacemakers in Magnetic Resonance Imaging; dissertation submitted to Swiss Federal Institute of Technology Zurich; pp. 1-131; Switzerland.

* cited by examiner

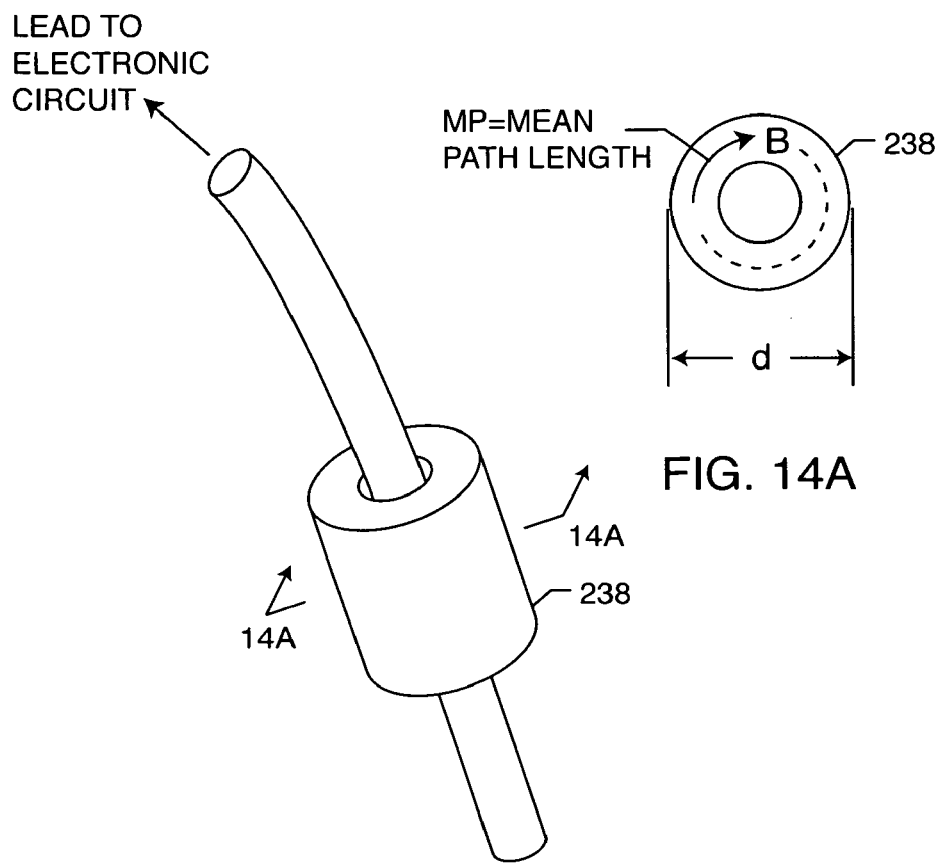
FIG. 14A
FIG. 14
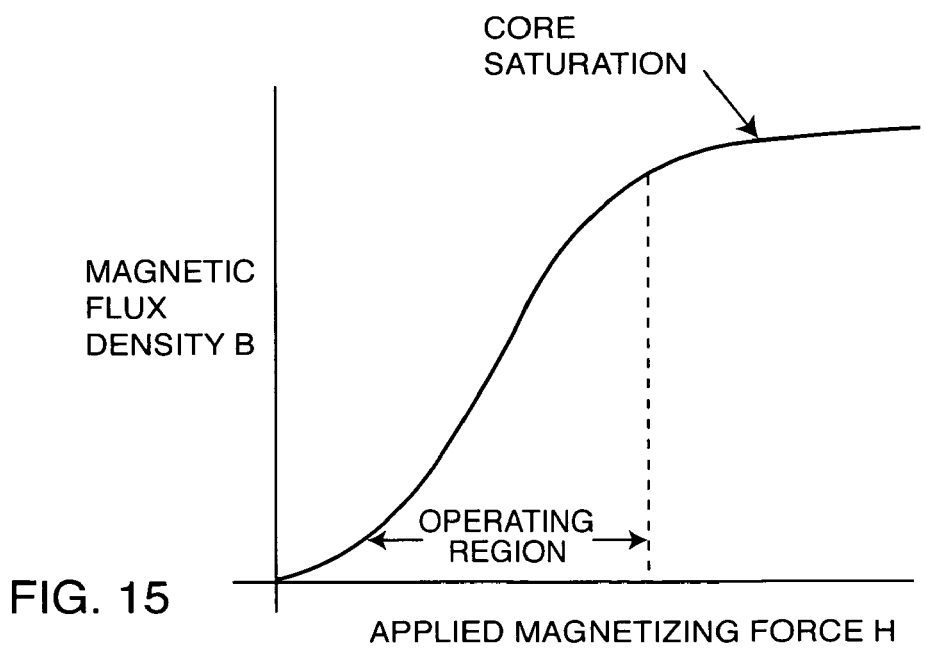
FIG. 15

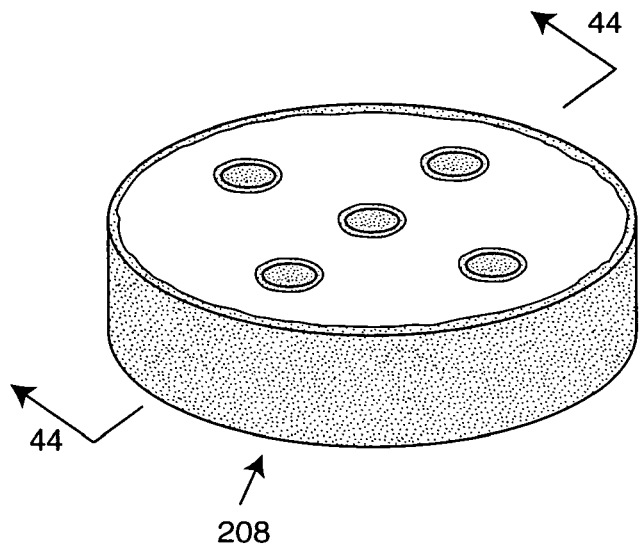
FIG. 43
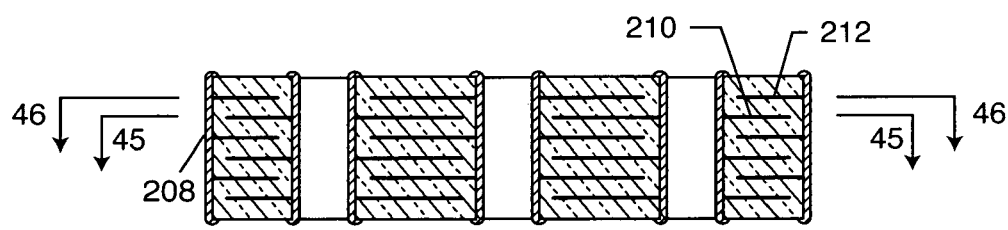
FIG. 44
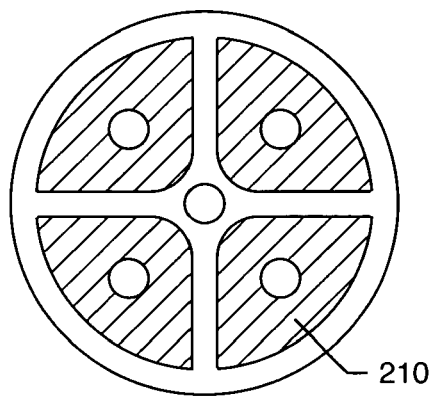 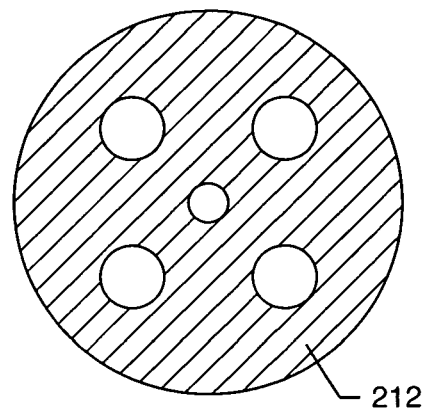
FIG. 45  FIG. 46

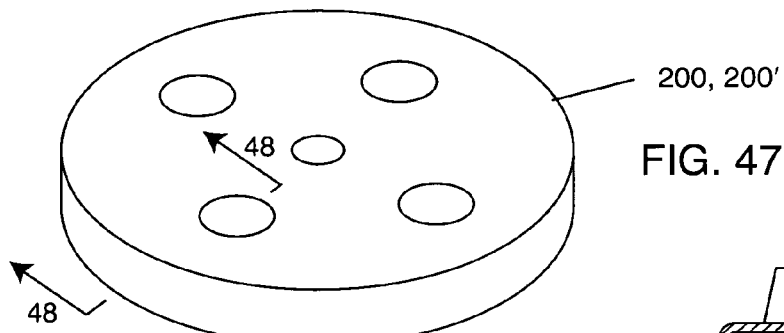
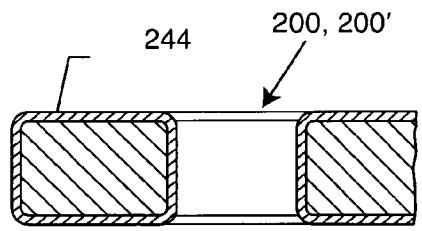
FIG. 47
FIG. 48
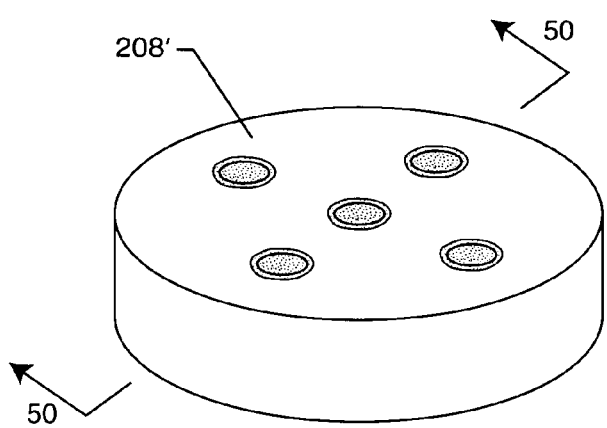
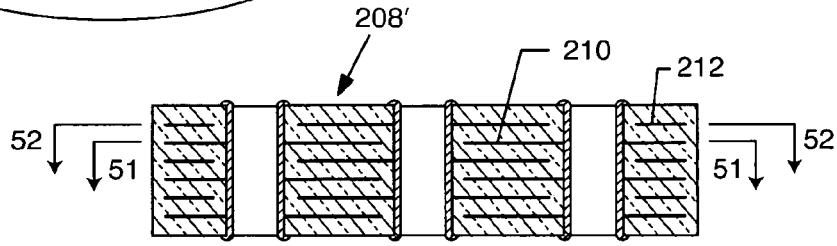
FIG. 49
FIG. 50
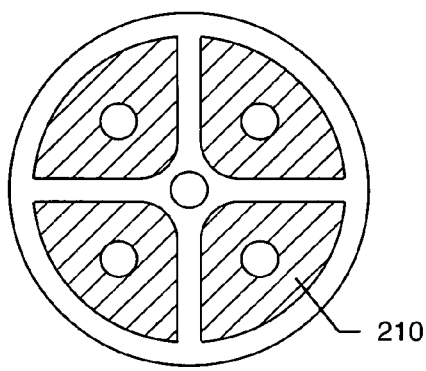 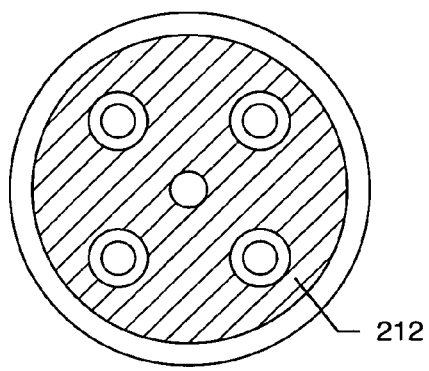
FIG. 51     FIG. 52

BODY FLUID SIDE ↓

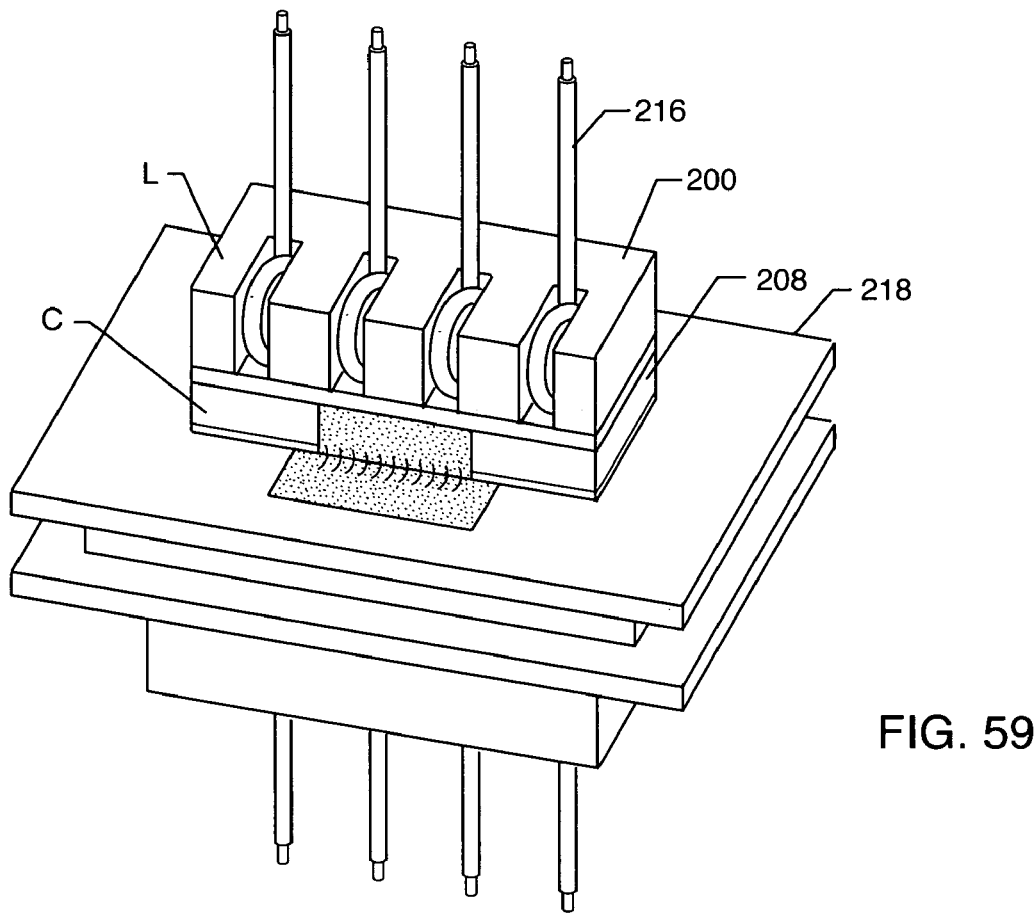
FIG. 59
BODY FLUID SIDE ↓
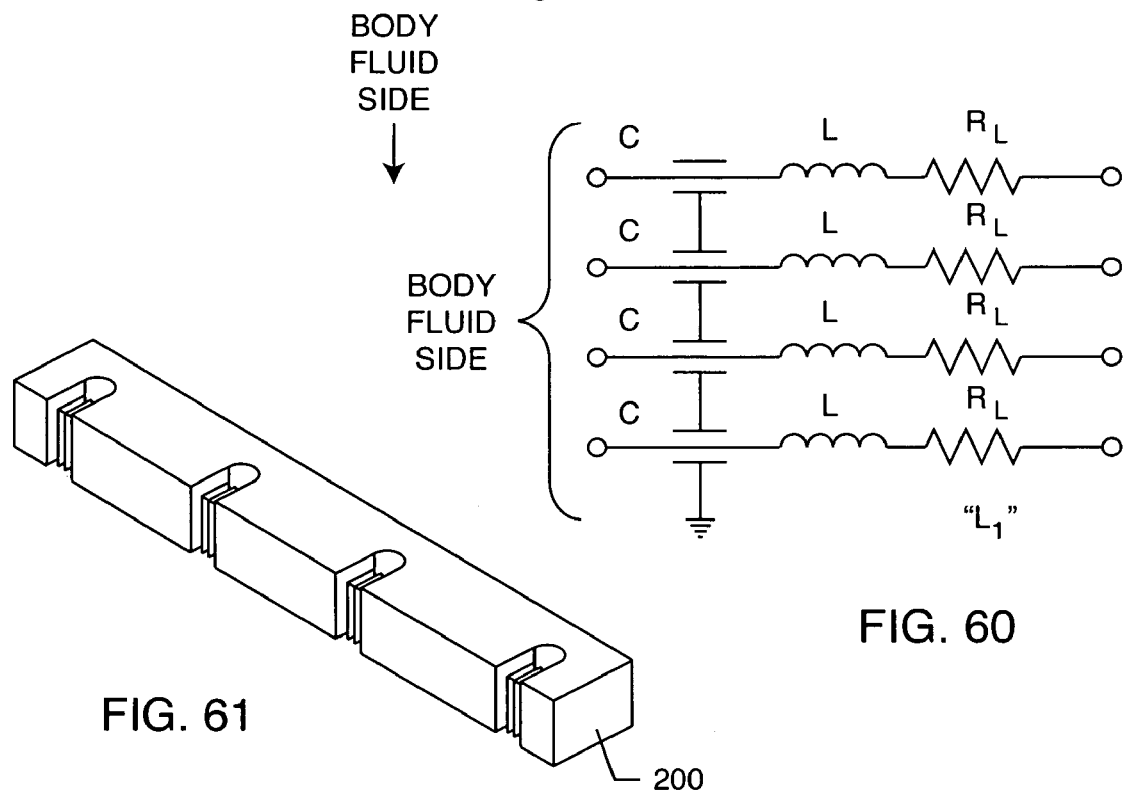
FIG. 61
FIG. 60

BODY FLUID SIDE ↓

BODY FLUID SIDE ↓

BODY FLUID SIDE
↓

BODY FLUID SIDE

BODY FLUID SIDE

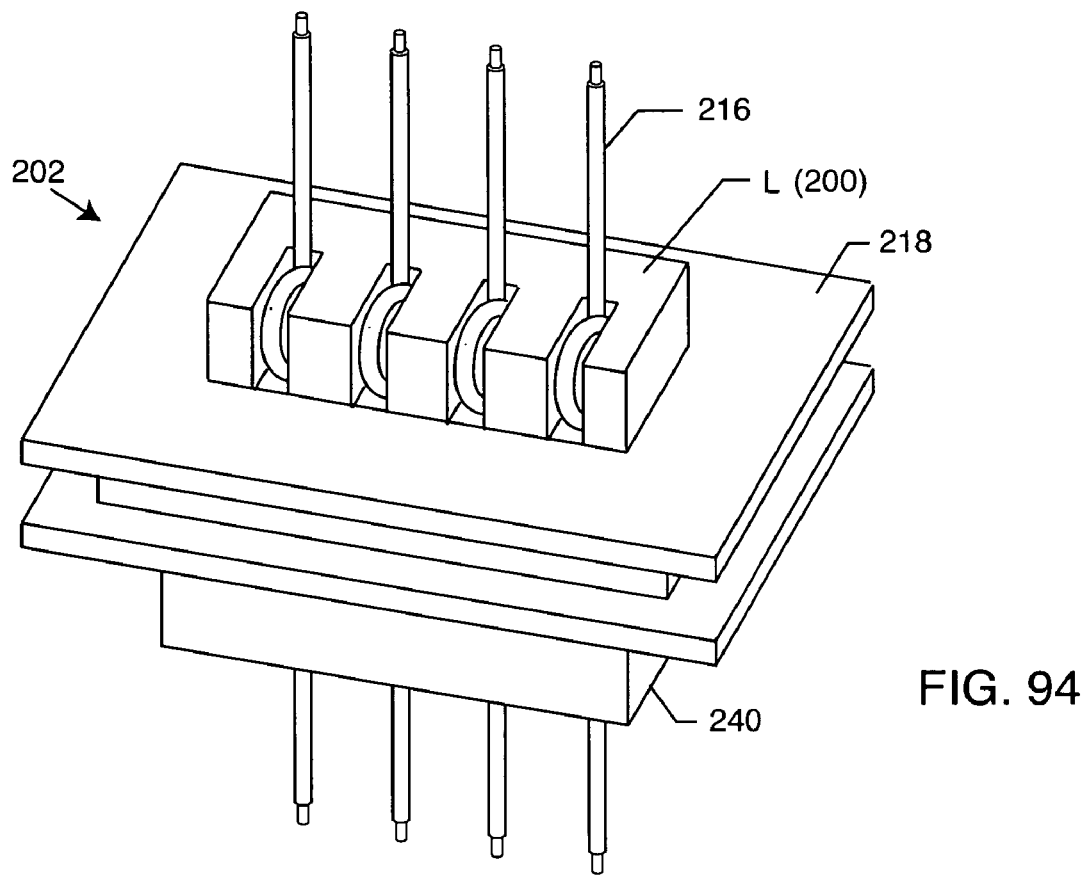
FIG. 94
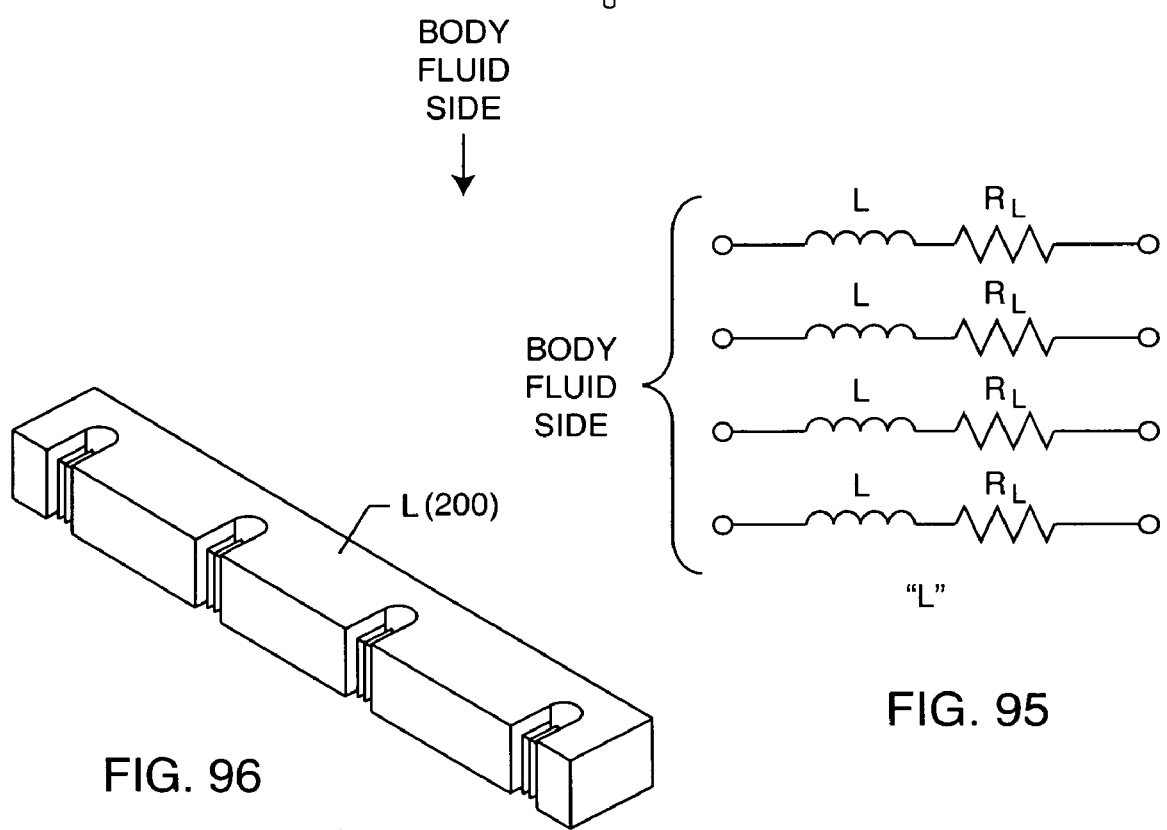
FIG. 95
FIG. 96

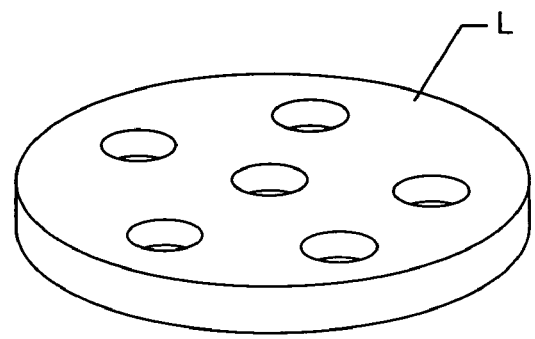
FIG. 98A
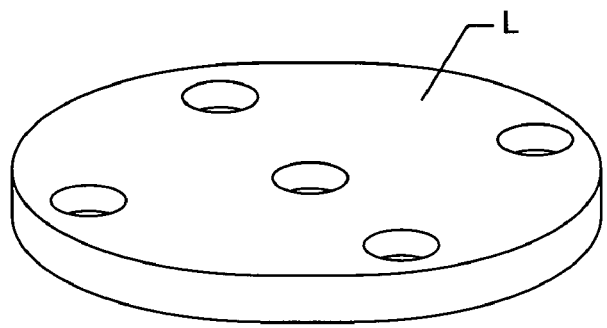
FIG. 98B
FIG. 98C
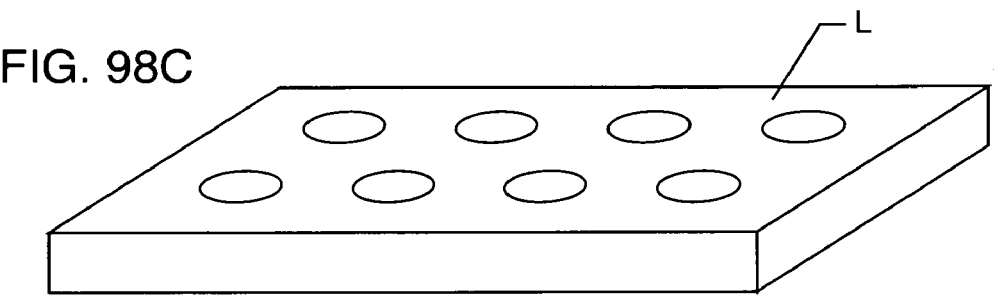
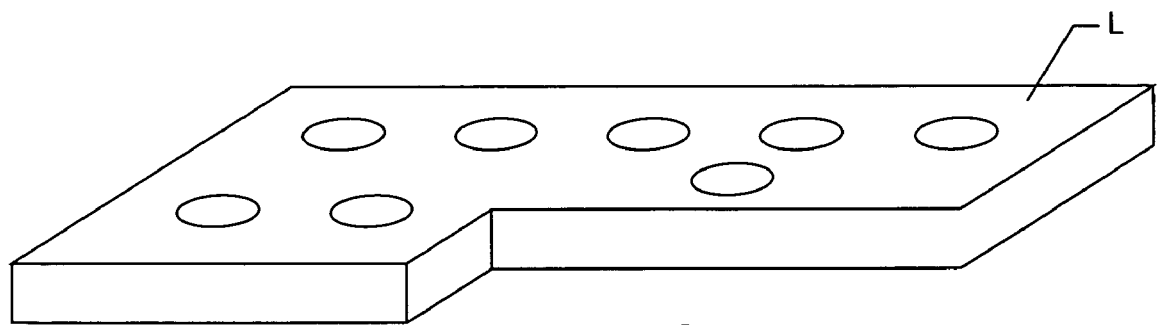
FIG. 98D

"L"

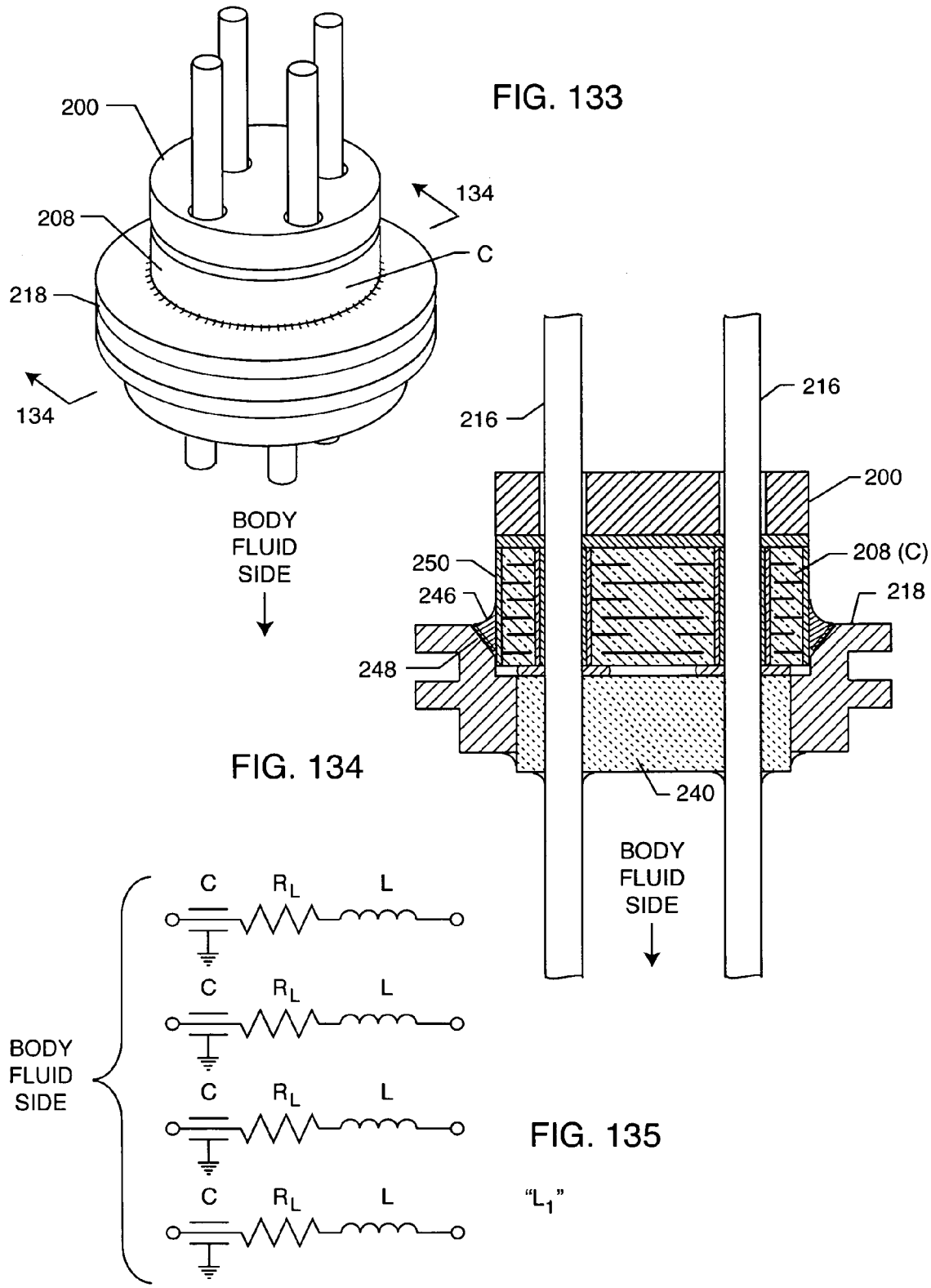

APPARATUS AND PROCESS FOR REDUCING THE SUSCEPTIBILITY OF ACTIVE IMPLANTABLE MEDICAL DEVICES TO MEDICAL PROCEDURES SUCH AS MAGNETIC RESONANCE IMAGING

RELATED APPLICATIONS

This is a Continuation-in-Part of U.S. patent application Ser. No. 10/825,900 filed on Apr. 15, 2004, now U.S. Pat. No. 6,999,818 the contents of which are incorporated herein by reference. This is also a Continuation-in-Part of U.S. patent application Ser. No. 10/842,967, filed May 10, 2004 now U.S. Pat. No. 7,038,900. This application is also a Continuation-in-Part of U.S. patent application Ser. No. 10/778,954, filed Feb. 12, 2004 now U.S. Pat. No. 6,985,347. This application also claims priority from U.S. Provisional Application Ser. No. 60/607,276, filed Sep. 2, 2004.

BACKGROUND OF THE INVENTION

This invention relates generally to EMI filter assemblies, particularly of the type used in active implantable medical devices (AIMDs) such as cardiac pacemakers, cardioverter defibrillators and the like, which decouple and shield internal electronic components of the medical device from undesirable electromagnetic interference (EMI) signals.

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Guidant, one will see that the use of MRI is generally contra-indicated with pacemakers and implantable defibrillators. See also "Safety Aspects of Cardiac Pacemakers in Magnetic Resonance Imaging", a dissertation submitted to the Swiss Federal Institute of Technology Zurich presented by Roger Christoph Luchinger. "Dielectric Properties of Biological Tissues: I. Literature Survey", by C. Gabriel, S. Gabriel and E. Cortout; "Dielectric Properties of Biological Tissues: II. Measurements and the Frequency Range 0 Hz to 20 GHz", by S. Gabriel, R. W. Lau and C. Gabriel; "Dielectric Properties of Biological Tissues: III. Parametric Models for the Dielectric Spectrum of Tissues", by S. Gabriel, R. W. Lau and C. Gabriel; and "Advanced Engineering Electromagnetics, C. A. Balanis, Wiley, 1989, all of which are incorporated herein by reference.

However, an extensive review of the literature indicates that MRI is indeed often used with pacemaker patients. The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. An absolute contra-indication for pacemaker patients means that pacemaker and ICD wearers are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI magnetic field, programming the pacemaker to fixed or asynchronous pacing mode (activation of the reed switch), and then careful reprogramming and evaluation of the pacemaker and patient after the procedure is complete. There have been reports of latent problems with cardiac pacemakers after an MRI procedure occurring many days later.

There are three types of electromagnetic fields used in an MRI unit. The first type is the main static magnetic field which is used to align protons in body tissue. The field strength varies from 0.5 to 1.5 Tesla in most of the currently available MRI units in clinical use. Some of the newer MRI system fields can go as high as 4 to 5 Tesla. This is about 100,000 times the magnetic field strength of the earth. A static magnetic field can induce powerful mechanical forces on any magnetic materials implanted within the patient. This would include certain components within the cardiac pacemaker itself and or leadwire systems. It is not likely (other than sudden system shut down) that the static MRI magnetic field can induce currents into the pacemaker leadwire system and hence into the pacemaker itself. It is a basic principle of physics that a magnetic field must either be time-varying as it cuts across the conductor, or the conductor itself must move within the magnetic field for currents to be induced. The lossy ferrite inductor or toroidal slab concept as described herein is not intended to provide protection against static magnetic fields such as those produced by magnetic resonance imaging.

The second type of field produced by magnetic resonance imaging is the pulsed RF field which is generated by the body coil or head coil. This is used to change the energy state of the protons and illicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during measurements and usually has a frequency of 21 MHz to 64 MHz to 128 MHz depending upon the static magnetic field strength.

The third type of electromagnetic field is the time-varying magnetic gradient fields which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements.

Feedthrough terminal pin assemblies are generally well known in the art for use in connecting electrical signals through the housing or case of an electronic instrument. For example, in implantable medical devices such as cardiac pacemakers, defibrillators and the like, the terminal pin assembly comprises one or more conductive terminal pins supported by an insulator structure for feedthrough passage of electrical signals from the exterior to the interior of the medical device. Many different insulator structures and related mounting methods are known for use in medical devices wherein the insulator structure provides a hermetic seal to prevent entry of patient body fluids into the medical device housing, where such body fluids could otherwise interfere with the operation of and/or cause damage to internal electronic components of the medical device.

In the past, two primary technologies have been employed to manufacture the hermetic seal. One technique involves the use of an alumina insulator which is metallized to accept brazing material. This alumina insulator is brazed to the terminal pin or pins, and also to an outer metal ferrule of titanium or the like. The alumina insulator supports the terminal pin or pins in insulated spaced relation from the ferrule which is adapted for suitable mounting within an access opening formed in the housing of the medical device. In an alternative technique, the hermetic seal comprises a glass-based seal forming a compression or matched fused glass seal for supporting the terminal pin or pins within an outer metal ferrule.

The feedthrough terminal pins are typically connected to one or more leadwires which, in the example of a cardiac pacemaker, sense signals from the patient's heart and also couple electronic pacing pulses from the medical device to the patient's heart. Unfortunately, these leadwires can act as an antenna to collect stray electromagnetic interference (EMI) signals for transmission via the terminal pins into the interior of the medical device. Such unwanted EMI signals can disrupt proper operation of the medical device, resulting in malfunction or failure. For example, it has been documented that stray EMI signals emanating from cellular telephones can inhibit pacemaker operation, resulting in asynchronous pacing, tracking and missed beats. To address this problem, hermetically sealed feedthrough terminal pin assemblies have been designed to include a feedthrough capacitor for decoupling EMI signals in a manner preventing such unwanted signals from entering the housing of the implantable medical device. See, for example, U.S. Pat. Nos. 4,424,551; 5,333,095; 5,751,539; 5,905,627; 5,973,906; 6,008,980; and 6,566.978. These prior art feedthrough capacitor EMI filters generally provide a high degree of attenuation to EMI in the frequency range between 450 and 3000 MHz.

While feedthrough capacitor filter assemblies have provided a significant advance in the art, a remaining area of concern is powerful low frequency emitters like MRI. As previously mentioned, feedthrough capacitors, as described in the prior art, work by providing a low impedance to ground (the overall electromagnetic shield of the implantable medical device) thereby by-passing such high frequency signals before they can enter and disrupt sensitive pacemaker electronic circuitry. However, when a pacemaker leadwire system is exposed to a powerful time varying electromagnetic field, such as induced by MRI, the last thing that is desirable is to create a low impedance in the leadwire system. Low impedance in the leadwire system only increases the current that would flow in the leads thereby creating additional leadwire heating and/or myocardial tissue necrosis at the pacemaker TIP to RING interface. Accordingly, it would be desirable to actually raise the impedance of the leadwire system at certain critical frequencies thereby reducing the undesirable currents in the leadwire system.

It is instructive to note how voltages and EMI are induced into an implanted leadwire system. At very low frequency (VLF), voltages are induced at the input to the cardiac pacemaker as currents circulate throughout the patient's body. Because of the vector displacement between the pacemaker can and, for example, the TIP electrode, voltage drop across body tissues may be sensed due to Ohms Law and the circulating RF signal. At higher frequencies, the implanted leadwire systems actually act as antennas where currents are induced along their length. These antennas are not very efficient due to the damping effects of body tissue; however, this can often be offset by body resonances. At very high frequencies (such as cellular telephone frequencies), EMI signals are induced only into the first area of the leadwire system (for example, at the header block of a cardiac pacemaker). This has to do with the wavelength of the signals involved and where they couple efficiently into the system. Magnetic field coupling into an implanted leadwire system is based on loop areas. For example, in a cardiac pacemaker, there is a loop formed by the leadwire as it comes from the cardiac pacemaker housing to its distal TIP located in the right ventricle. The return path is through body fluid and tissue generally straight from the TIP electrode in the right ventricle back up to the pacemaker case or housing. This forms an enclosed area which can be measured from patient X-rays in square centimeters. The inventor has participated with the Association for the Advancement of Medical Instrumentation (AAMI) through their Committee PC69, which is chaired by Mitchell Shein of the United States Food and Drug Administration (FDA). This committee is known as the Pacemaker EMC Task Force. One of the recent accomplishments of this committee was to visit various pacemaker centers around the United States and to trace patient X-rays and actually measure these loop areas. The report was recently issued which indicates that the average loop area is 200 to 225 square centimeters. This is an average and is subject to great statistical variation. For example, in a large adult patient with an abdominal implant, the implanted loop area is much larger (greater than 450 square centimeters).

Relating now to the specific case of MRI, the magnetic gradient fields would be induced through enclosed loop areas. However, the pulsed RF fields, which are generated by the body coil, would also be induced into the leadwire system by antenna action.

There are a number of potential problems with MRI, including:

(1) Closure of the pacemaker reed switch. When a pacemaker is brought close to the MRI scanner, the reed switch can close, which puts the pacemaker into a fixed rate or asynchronous pacing mode. Asynchronous pacing may compete with the patient's underlying cardiac rhythm. This is one reason why patients have generally been advised not to undergo MRI. Fixed rate or asynchronous pacing for most patients is not an issue. However, in patients with unstable conditions, such as myocardial ischemia, there is a substantial risk for ventricular fibrillation during asynchronous pacing. In most modern pacemakers the magnetic reed switch function is programmable. If the magnetic reed switch response is switched off, then synchronous pacing is still possible even in strong magnetic fields. The possibility to open and re-close the reed switch in the main magnetic field by the gradient field cannot be excluded. However, it is generally felt that the reed switch will remain closed due to the powerful static magnetic field. It is theoretically possible for certain reed switch orientations at the gradient field to be capable of repeatedly closing and re-opening the reed switch.

(2) Reed switch damage. Direct damage to the reed switch is theoretically possible, but has not been reported in any of the known literature. In an article written by Roger Christoph Luchinger of Zurich, he reports on testing in which reed switches were exposed to the static magnetic field of MRI equipment. After extended exposure to these static magnetic fields, the reed switches functioned normally at close to the same field strength as before the test.

(3) Pacemaker displacement. Some parts of pacemakers, such as the batteries and reed switch, contain ferrous magnetic materials and are thus subject to mechanical forces during MRI. Pacemaker displacement may occur in response to magnetic force or magnetic torque.

(4) Radio frequency field. At the frequencies of interest in MRI, RF energy can be absorbed and converted to heat. The power deposited by RF pulses during MRI is complex and is dependent upon the power and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. The cause of heating in an MRI environment is two fold: (a) RF field coupling to the lead can occur which induces significant local heating; and (b) currents induced during the RF transmission can cause local Ohms Law heating next to the distal TIP electrode of the implanted lead. The RF field in an MRI scanner can produce enough energy to induce leadwire currents sufficient to destroy some of the adjacent myocardial tissue. Various ablation has also been observed. The effects of this heating are not readily detectable by monitoring during the MRI. Indications that heating has occurred would include an increase in pacing threshold, myocardial perforation and lead penetration, or even arrhythmias caused by scar tissue. Such long term heating effects of MRI have not been well studied yet.

(5) Alterations of pacing rate due to the applied radio frequency field. It has been observed that the RF field may induce undesirable fast pacing (QRS complex) rates. There are two mechanisms which have been proposed to explain rapid pacing: direct interference with pacemaker electronics or pacemaker reprogramming (or reset). In both of these cases, it would be desirable to raise the impedance, make the feedthrough capacitor more effective and provide a very high degree of protection to AIMD electronics. This will make alterations in pacemaker pacing rate and/or pacemaker reprogramming much more unlikely.

(6) Time-varying magnetic gradient fields. The contribution of the time-varying gradient to the total strength of the MRI magnetic field is negligible, however, pacemaker systems could be affected because these fields are rapidly applied and removed. The time rate of change of the magnetic field is directly related to how much electromagnetic force and hence current can be induced into a leadwire system. Luchinger reports that even using today's gradient systems with a time-varying field up to 50 Tesla per second, the induced currents are likely to stay below the biological thresholds for cardiac fibrillation. A theoretical upper limit for the induced voltage by the time-varying magnetic gradient field is 20 volts. Such a voltage during more than 0.1 milliseconds could be enough energy to directly pace the heart.

(7) Heating. Currents induced by time-varying magnetic gradient fields may lead to local heating. Researchers feel that the calculated heating effect of the gradient field is much less as compared to that caused by the RF field and therefore may be neglected.

There are additional problems possible with implantable cardioverter defibrillators (ICDs). ICDs use different and larger batteries which could cause higher magnetic forces. The programmable sensitivity in ICDs is normally much higher than it is for pacemakers, therefore, ICDs may falsely detect a ventricular tachyarrhythmia and inappropriately deliver therapy. In this case, therapy might include anti-tachycardia pacing, cardio version or defibrillation (high voltage shock) therapies. MRI magnetic fields may prevent detection of a dangerous ventricular arrhythmia or fibrillation. There can also be heating problems of ICD leads which are expected to be comparable to those of pacemaker leads. Ablation of vascular walls is another concern.

In summary, there are a number of studies that have shown that MRI patients with active implantable medical devices, such as cardiac pacemakers, can be at risk for potential hazardous effects. However, there are a number of anecdotal reports that MRI can be safe for extremity imaging of pacemaker patients (only when an MRI is thought to be an absolute diagnostic necessity). The effect of an MRI system on the function of pacemakers and ICDs depends on various factors, including the strength of the static magnetic field, the pulse sequence (gradient and RF field used), the anatomic region being imaged, and many other factors. Further complicating this is the fact that each manufacturer's pacemaker and ICD designs behave differently. Most experts still conclude that MRI for the pacemaker patient should not be considered safe. Paradoxically, this also does not mean that the patient should not receive MRI. The physician must make an evaluation given the pacemaker patient's condition and weigh the potential risks of MRI against the benefits of this powerful diagnostic tool. As MRI technology progresses, including higher field gradient changes over time applied to thinner tissue slices at more rapid imagery, the situation will continue to evolve and become more complex. An example of this paradox is a pacemaker patient who is suspected to have a cancer of the lung. Treatment of such a tumor may require stereotactic imaging only made possible through fine focus MRI. With the patient's life literally at risk, the physician may make the decision to perform MRI in spite of all of the previously described attendant risks to the pacemaker system.

It is clear that MRI will continue to be used in patients with an implantable medical device. There are a number of other hospital procedures, including electrocautery surgery, lithotripsy, etc., to which a pacemaker patient may also be exposed. Accordingly, there is a need for circuit protection devices which will improve the immunity of active implantable medical device systems to diagnostic procedures such as MRI. There is also a need to provide increased filtering for AIMD's due to the recent proliferation in the marketplace of new higher power emitters. These include aftermarket cellular telephone amplifiers, associated higher gain antennas and radio frequency identification (RFID) readers and scanners. The present invention fulfills all of these needs and provides other related advantages.

SUMMARY OF THE INVENTION

The present invention resides in a feedthrough terminal assembly for an active implantable medical device (AIMD) including a plurality of leadwires extending from electronic circuitry of the AIMD, and a lossy ferrite inductor through which the leadwires extend in non-conductive relation for increasing the impedance of the leadwires at selected RF frequencies and reducing magnetic flux core saturation of the lossy ferrite inductor through phase cancellation of signals carried by the leadwires. The present invention also resides in a process for filtering electromagnetic interference (EMI) in an implanted leadwire extending from an active implantable medical device (AIMD) into body fluids or tissue, wherein the leadwire is subjected to occasional high-power electromagnetic fields such as those produced by medical diagnostic equipment including magnetic resonance imaging. In the process of the present invention, the leadwire is passed through an inductive and resistive low pass filter element to increase EMI protection of AIMD electronics and to raise the output impedance of the AIMD circuitry thereby reducing currents induced in the implanted leadwire by the occasional high-power electromagnetic fields, wherein the low pass filter element has a diameter-to-thickness ratio of at least 1:1.

Both the feedthrough terminal assembly and related process are specifically designed for use with active implantable medical devices including a cardiac pacemaker, an implantable defibrillator, a congestive heart failure device, a hearing implant, a neurostimulator, a drug pump, a ventricular assist device, an insulin pump, a spinal cord stimulator, an implantable sensing system, an artificial heart, an incontinence device, a bone growth stimulator, a gastric pacemaker, or a prosthetic device.

In the novel feedthrough terminal assemblies described herein, the leadwires may comprise a first leadwire extending from the electronic circuitry of the AIMD through a housing of the AIMD to a point within a human body. A second leadwire may be conductively coupled to at least a portion of the AIMD housing and the AIMD circuitry. A conformal coating is provided over the lossy ferrite inductor, which coating preferably comprises Paralene C, D, E or N.

In several embodiments, an insulator is disposed between the lossy ferrite inductor and the leadwires. One or more additional lossy ferrite inductors may be provided through which the leadwires extend in non-conductive relation. The lossy ferrite inductors may be disposed adjacent to one another and each can be comprised of materials having different physical or electrical properties. When a hermetic insulator is disposed between the leadwires and the ferrule, the lossy ferrite inductors may be disposed on opposite sides of the insulator.

Advantageously, the lossy ferrite inductor may be bonded to the insulator to form a beam-like structure. Moreover, the lossy ferrite inductor may include an aperture through which a leak detection gas can be detected.

In several embodiments, leadwires are wound around the lossy ferrite inductor to form multiple turns. Adjacent portions of the wound leadwire are electrically insulated from one another. The lossy ferrite inductor may further include a notch for receiving the wound leadwire. Further, the lossy ferrite inductor may include multiple notches therein. At least two leadwires may be wound about the lossy ferrite inductor to form one or more turns, and the turn count for the leadwires need not be equal.

Means are also provided for maintaining the lossy ferrite inductor in close association with the AIMD without laminating or bonding the inductor to another component. Such maintaining means may comprise a mechanical lock, a deformation in the leadwire, a cured polymer, or a wire bond pad attached to the leadwire.

At least two of the leadwires may be routed through the lossy ferrite inductor in opposite directions. As shown in one of the illustrated embodiments, the at least two leadwires comprise Tip and Ring leadwires for the active implantable medical device. Moreover, a phase cancellation antenna may be provided which extends through the lossy ferrite inductor in non-conductive relation.

The feedthrough terminal assembly may further include a feedthrough filter capacitor having a first set of electrode plates conductively coupled to at least one of the leadwires, and a second set of electrode plates conductively coupled to a housing, ferrule or ground plane of the active implantable medical device. Such an assembly may form an "L", "Pi", "T", "LL", "5 element" or higher order "n element" low pass filter circuit.

The lossy ferrite inductor may be bonded to the capacitor to form a beam-like structure. Further, the capacitor and the lossy ferrite inductor may be at least partially housed within a ferrule. In this case, an insulative cap is preferably disposed over the lossy ferrite inductor opposite the capacitor.

A second lossy ferrite inductor may be provided through which the leadwires extend in non-conductive relation. The lossy ferrite inductors may be disposed on opposite sides of the capacitor if desired.

The feedthrough capacitor may comprise first and second feedthrough capacitors associated with the lossy ferrite inductor. The first and second feedthrough capacitors may be disposed adjacent to opposite surfaces of the lossy ferrite inductor, and at least one of the capacitors may be internally grounded.

In an illustrated embodiment, the first and second capacitors each include a first set of electrode plates conductively coupled to at least one of the leadwires, and a second set of electrode plates conductively coupled to the AIMD housing, ferrule or ground plane. The first capacitor comprises an externally grounded capacitor, and the second capacitor comprises an internally grounded capacitor. A conductive material extends through both the first and second feedthrough capacitors to conductively couple the second set of electrode plates of the second capacitor with the second set of electrode plates of the first capacitor. Of course, the second set of electrode plates may be either externally or internally grounded to and conductively coupled with the AIMD housing, ferrule or ground plane.

The lossy ferrite inductor may comprise first and second lossy ferrite inductors arranged, with the capacitors, to form an "$LL_1$", "5 element" or an "n element" low pass filter circuit, whereby the first inductor is disposed on the body fluid side of the first capacitor, and the second inductor is disposed between the first and second capacitor. Preferably, the inductance of the first inductor is relatively large in comparison with the second inductor and the capacitance of the first capacitor is relatively small in comparison with the second capacitor.

In other embodiments, the lossy ferrite inductor may be disposed on a body fluid side of the feedthrough assembly as part of an "L", "L2", "T", "LL", "5 element" or "n element" low pass filter circuit.

A wire bond pad may be conductively coupled to at least one of the leadwires, and a surface of the inductor may be configured to form a tortuous path between at least one of the leadwires and an adjacent conductor.

Another aspect of the present invention resides in novel processes for filtering electromagnetic interference in a plurality of leadwires extending from an active implantable medical device (AIMD) to different points within a human body. In particular, the process involves the steps of passing the leadwires through a common lossy inductive element to increase the impedance of the leadwires at selected RF frequencies and reduce the magnetic flux core saturation of the inductive element through phase cancellation of signals carried by the leadwires.

Moreover, a process is provided for filtering the electromagnetic signals in a plurality of leadwires extending from an active implantable medical device into body fluids or tissue, wherein the leadwires are subjected to occasional high-power electromagnetic fields or signals generated by AIMD circuitry or external sources such as medical diagnostic equipment including magnetic resonance imaging (MRI). The steps comprise conductively coupling the leadwires to respective sets of electrode plates within a feedthrough capacitor optimized for electromagnetic interference (EMI) filtering, and passing the leadwires through a common inductive element disposed adjacent to the feedthrough capacitor and between the AIMD circuitry and the feedthrough capacitor, for decoupling signals induced on the leadwires by the occasional high-power electromagnetic fields or signals generated by AIMD circuitry or external sources, from the feedthrough capacitor, to protect AIMD circuitry from ringback of energy from the feedthrough capacitor induced by the occasional high-power electromagnetic fields or signals.

In various embodiments, the processes of the present invention may include the steps of placing the inductive element on a body fluid side of a feedthrough assembly as part of an L, L2, T, $LL_1$, 5 element, or "n element" low pass filter circuit. Further, the process may include the step of forming a tortuous path on a surface of the inductive element between at least one of the leadwires and an adjacent conductor. Moreover, all of the variations described above in connection with the novel feedthrough terminal assembly may be applied to the process to accomplish varying and highly desirable results in particular applications.

Other features and advantages of the present invention will become apparent from the following more detailed description, taken in conjunction with the accompanying drawings which, by way of example, illustrate the principles of the invention.

BRIEF DESCRIPTION OF THE DRAWINGS

The accompanying drawings illustrate the invention. In such drawings:

FIG. 14 illustrates use of a ferrite bead inductor with a lead to an electronic circuit;

FIG. 14A is a sectional view taken generally along the line 14A-14A of FIG. 14;

FIG. 15 is an illustration of a ferrite core saturation curve for the ferrite bead of FIG. 14;

FIG. 43 is a perspective view of the lower feedthrough capacitor illustrated in FIG. 36;

FIG. 44 is a sectional view taken generally along the line 44-44 of FIG. 43;

FIG. 45 is a sectional view taken generally along the line 45-45 of FIG. 44;

FIG. 46 is a sectional view taken generally along the line 46-46 of FIG. 44;

FIG. 47 is a perspective view of a sintered lossy ferrite inductor, two of which are shown in FIG. 36;

FIG. 48 is an enlarged, fragmented sectional view taken generally along the line 48-48 of FIG. 47;

FIG. 49 is a perspective view of the internally grounded upper feedthrough filter capacitor shown in FIG. 36;

FIG. 50 is a sectional view taken generally along the line 50-50 of FIG. 49;

FIG. 51 is a sectional view taken generally along the line 51-51 of FIG. 50;

FIG. 52 is a sectional view taken generally along the line 52-52 of FIG. 50;

FIG. 59 is a perspective view of an inline quadpolar terminal including a lossy ferrite inductor with multiple turns of leadwire co-bonded to an inline quadpolar feedthrough capacitor;

FIG. 60 is an electrical schematic diagram of the "$L_1$" filter circuit of FIG. 59;

FIG. 61 is a perspective view of an improved inline lossy ferrite inductor which facilitates passing multiple turns;

FIG. 94 is a perspective view of an inline quadpolar lossy ferrite inductor similar to that shown in FIG. 59, except the feedthrough capacitor has been removed;

FIG. 95 is an electrical schematic diagram of the structure shown in FIG. 94;

FIG. 96 is a perspective view of a modified lossy ferrite inductor assembly that may be utilized in connection with the structure of FIG. 94;

FIGS. 98A-98D illustrate various examples of the shapes that the lossy ferrite inductor can take;

FIG. 117 is a sectional view similar to FIG. 86, but employing the novel lossy ferrite inductor of FIG. 113;

FIG. 118 illustrates the schematic diagram of the "L" EMI filtered terminal assembly of FIG. 117;

FIG. 119 is an enlarged fragmented perspective view of a portion of the terminal lead shown in FIG. 117, illustrating that a portion of an insulator is removed from the lead as it extends upwardly through the capacitor;

FIG. 120 is a perspective view of a unipolar lossy ferrite inductor designed with a novel slot arrangement;

FIG. 121 is a cross-sectional view taken generally along the line 121-121 of FIG. 120;

FIG. 122 is a cross-sectional view illustrating a two-turn "L" lossy ferrite inductor of FIG. 120;

FIG. 123 is a fragmented perspective view of a novel two-turn unipolar inductor embodying the present invention;

FIG. 124 is a perspective view of a unipolar lossy ferrite inductor with four slots;

FIG. 125 is a perspective view illustrating the novel four-turn unipolar lossy ferrite inductor of FIG. 124 mounted to a hermetic terminal and assembled;

FIG. 126 is a perspective view of an inline quadpolar lossy ferrite inductor having four slots in accordance with the present invention;

FIG. 127 is a perspective view of a quadpolar feedthrough filter terminal assembly wherein the lossy ferrite inductor is loosely seated on top of an alumina insulator without any bonding material, showing various fastening devices;

FIG. 128 is a sectional view taken generally along the line 128-128 of FIG. 127;

Figure 127:
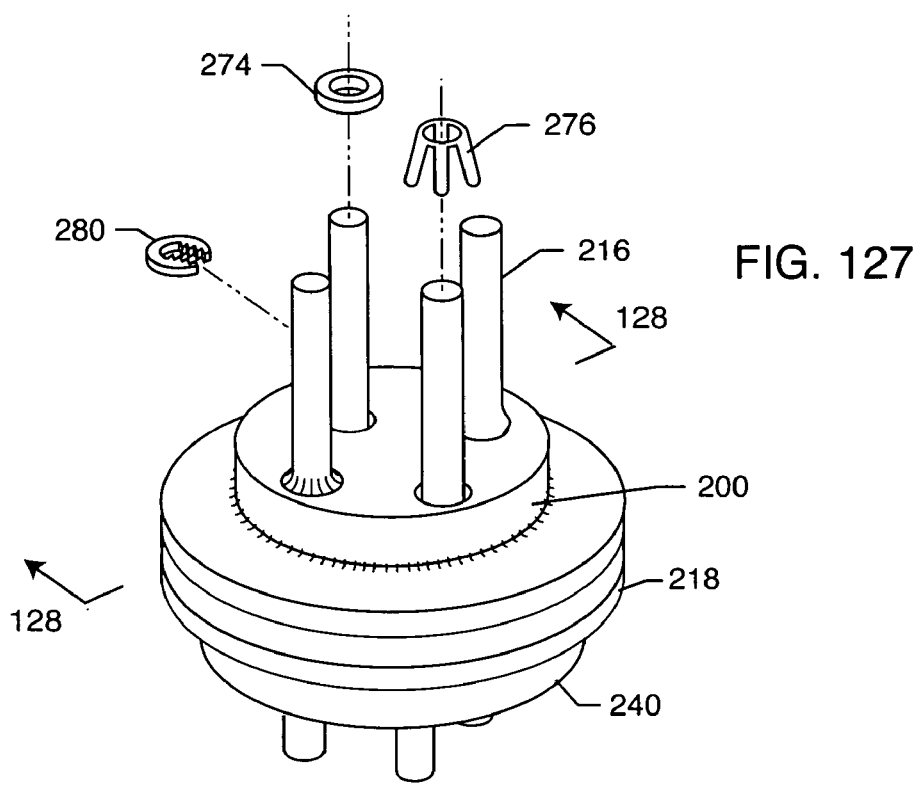
Figure 128:
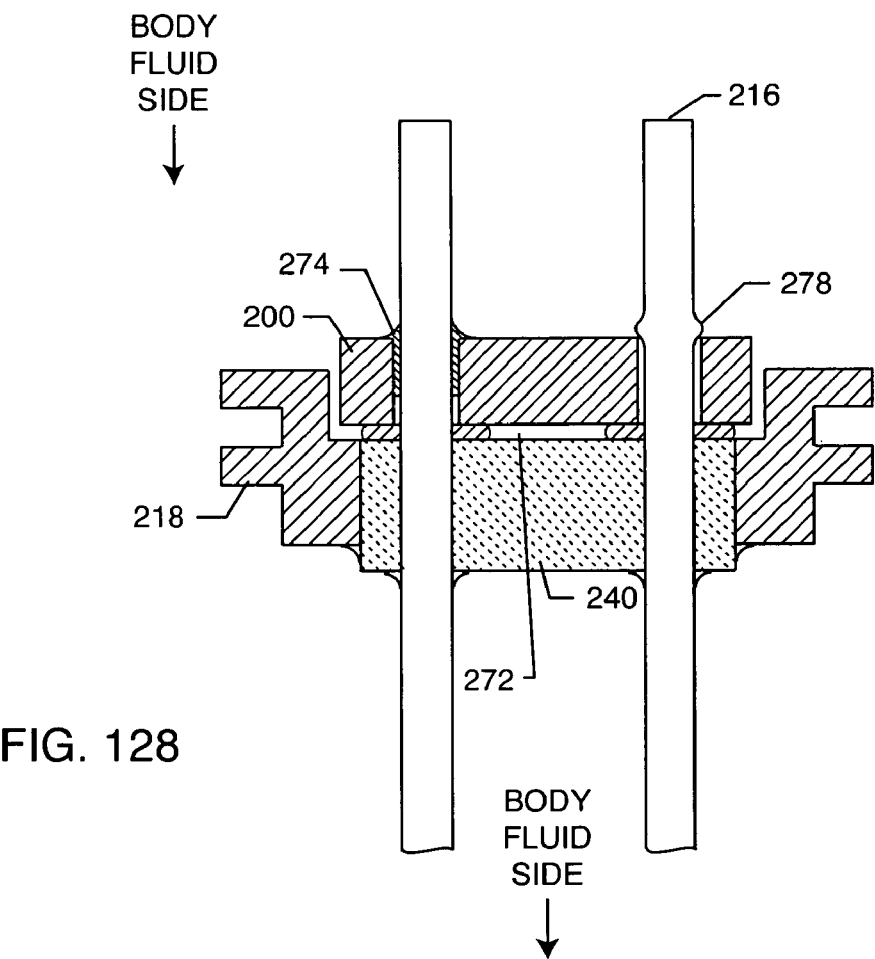
Figure 129:
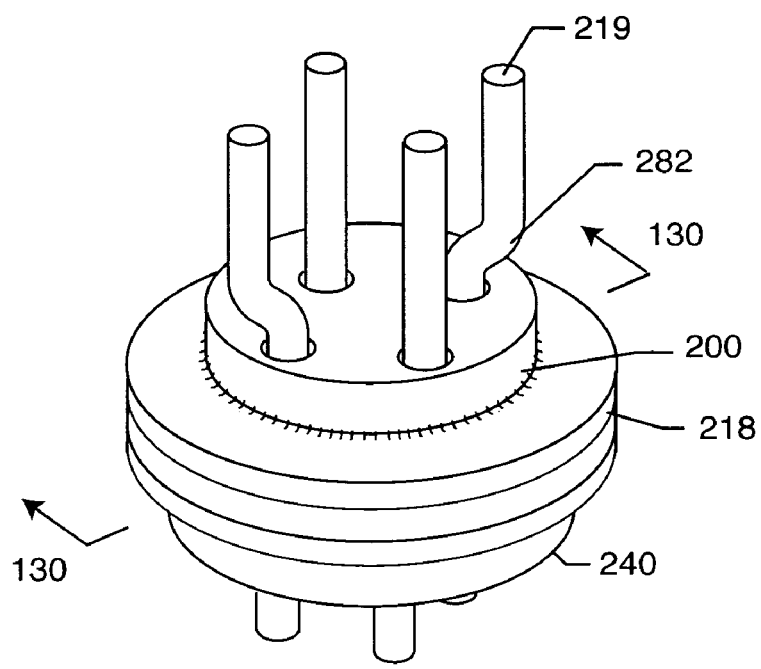
Figure 130:
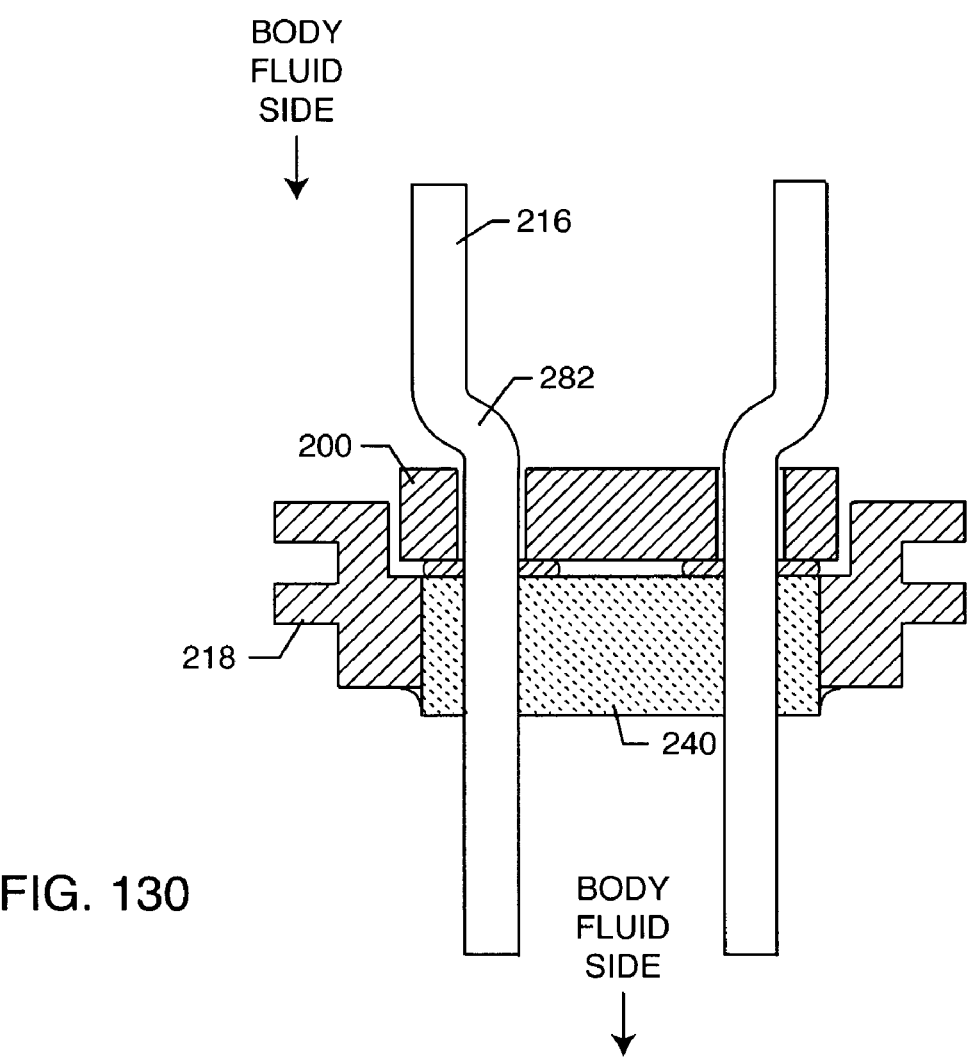

FIG. 129 is a perspective view of a quadpolar feedthrough filter terminal assembly similar to that illustrated in FIGS. 127 and 128, illustrating another embodiment thereof;

FIG. 130 is a sectional view taken generally along the line 130-130 of FIG. 129.

Figure 131:
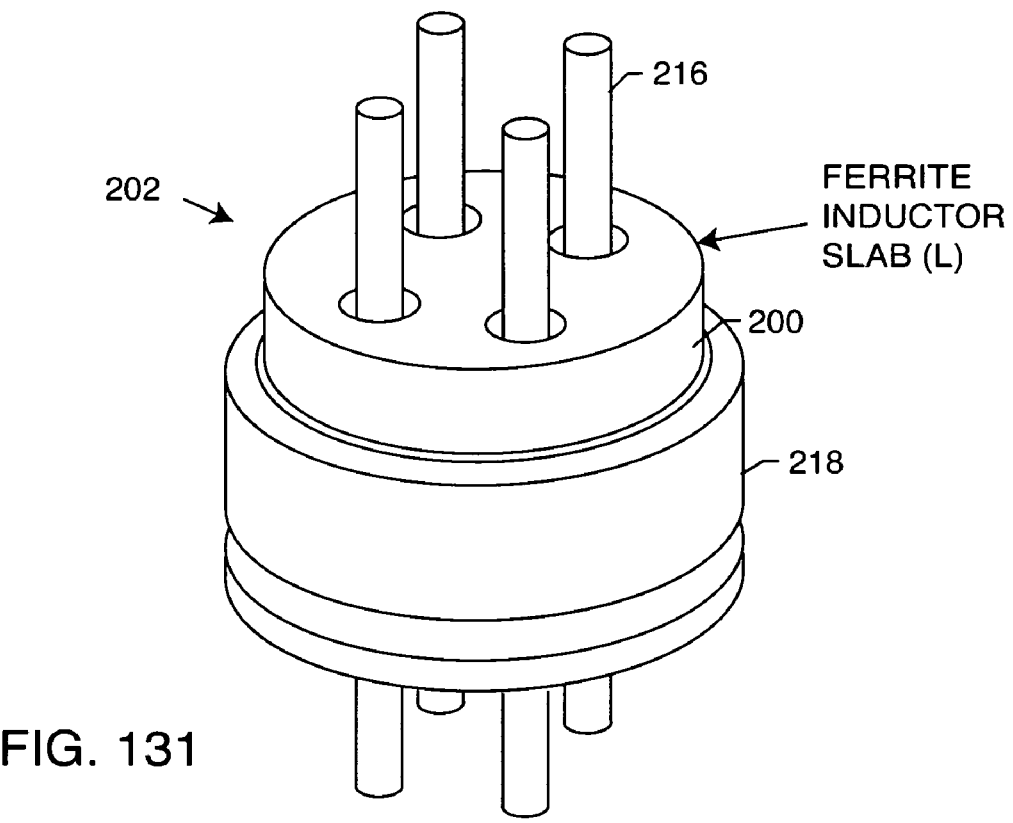
Figure 132:
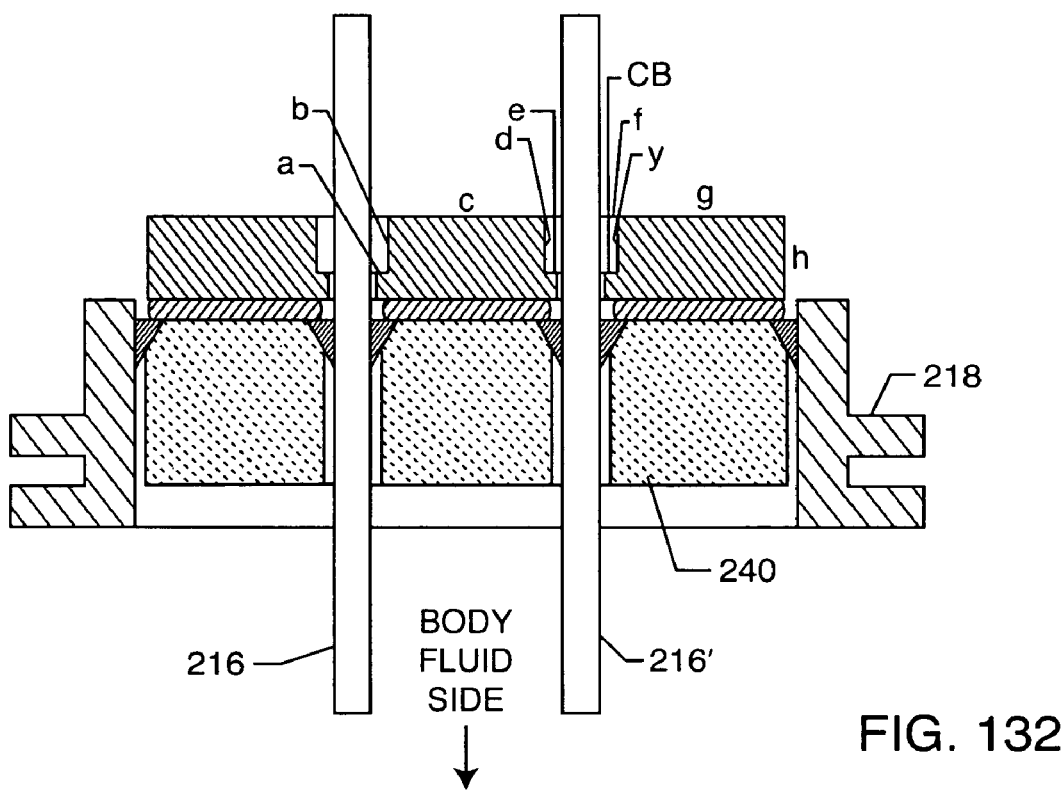
Figure 136:
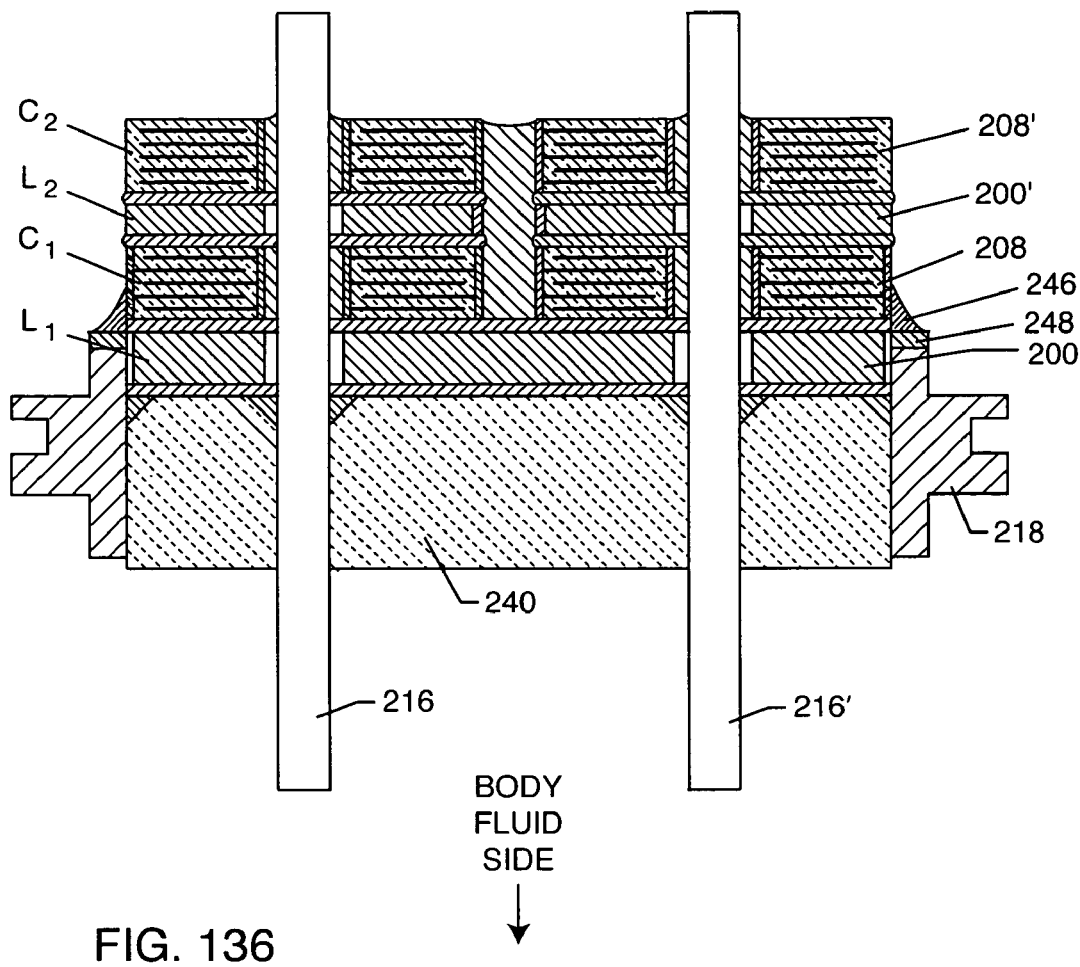
Figure 137:
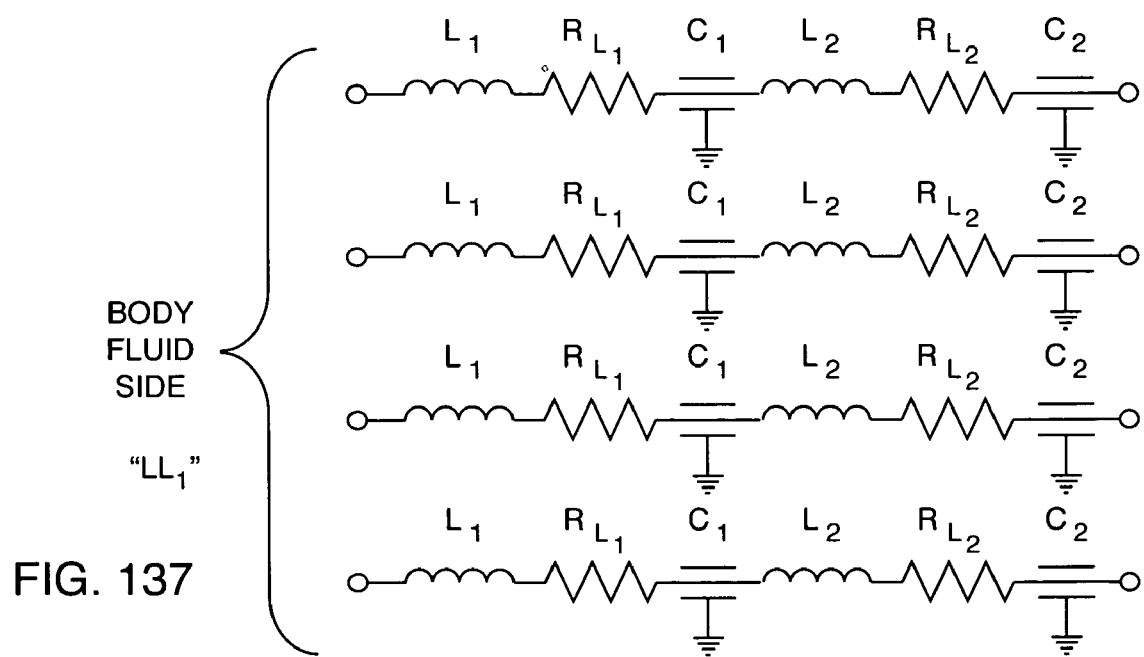

FIG. 131 is a perspective view of a quadpolar EMI terminal wherein recesses are formed in the lossy inductor slab adjacent to the egress point of the terminal pins;

FIG. 132 is a sectional view through the quadpolar terminal of FIG. 131;

FIG. 133 is a top and side perspective view of another quadpolar "$L_1$" L-circuit EMI filter;

FIG. 134 is a sectional view taken generally along the line 134-134 of FIG. 133;

FIG. 135 is the schematic diagram of the "$L_1$" quadpolar filter of FIG. 133;

FIG. 136 is a sectional view similar to FIG. 134, illustrating the configuration of "double L" ($LL_2$) circuit; and FIG. 137 is a schematic diagram for the "$LL_2$" filter of FIG. 136.

DETAILED DESCRIPTION OF THE PREFERRED EMBODIMENTS

As shown in the drawings for purposes of illustration, the present invention relates to a lossy ferrite inductor with both resistive and inductive properties 200 (hereinafter referred to as "lossy ferrite inductor"), which is installed in proximity or adjacent to the hermetic terminal 202 of an active implantable medical device (AIMD) 204. The lossy ferrite inductor 200 can be combined with a feedthrough filter capacitor assembly 206 which includes a capacitor 208 having first and second sets of conductive electrode plates 210, 212 embedded within an insulative or dielectric body 214, which is mounted to the hermetic terminal 202 of the implantable medical device 204. At least one feedthrough terminal pin or leadwire 216 extends through the lossy ferrite inductor 200 in non-conductive relation. When used in combination with a feedthrough capacitor 208, the feedthrough terminal pin 216 extends through the capacitor in conductive relation with the first set of electrode plates 210. An outer ferrule, housing or ground plane 218 is mounted adjacent to the capacitor in conductive relation with the second set of electrode plates 212.

The lossy ferrite inductor 200 works to absorb EMI energy (convert to heat) and increase the impedance of the leadwire system 220 of the implantable medical device 204. On the other hand, the feedthrough capacitor 208, which is well known in the art, reduces the impedance to ground thereby shunting or bypassing high frequency electromagnetic signals.

Feedthrough capacitors used by themselves are very effective high frequency filters. However, due to capacitance, size, and circuit current limitations, they are not very effective low frequency filters. The lossy ferrite inductor concept as disclosed herein is extremely effective for a pulsed RF field. The lossy ferrite inductor 200 produces substantial series inductance and series resistance at these frequencies. Accordingly, this raises the impedance of the leadwire system 220 itself.

The resistive component of the lossy ferrite inductor also converts EMI from magnetic resonance imaging (MRI) into harmless heat. This results in substantially reduced current into the leadwire system 220.

RF currents induced into a pacemaker leadwire system 220 can be problematic in three ways: (1) there can be direct heating effects which cause the temperature to rise to excessive levels in the leadwire; (2) current flowing through body tissue 222 which can cause localized heating and body tissue damage; and (3) RF currents which enter into the input circuitry 224 of the cardiac pacemaker and cause the device to malfunction or fail electronically. The lossy ferrite inductor concept would have minimal to limited effect at a 1 kHz frequency. The reason is that the inductive reactance at this frequency is extremely low. Accordingly, the impedance of the leadwire system 220 would really not be substantially affected. There is some effect from resistive loss in the lossy ferrite inductor 200, but it too is minimal. The lossy ferrite inductor 200 concept as disclosed herein, has its highest efficacy for attenuating the pulse RF field component of magnetic resonance imaging. When combined with a feedthrough capacitor 208, this can reduce leadwire current and also provide a very high degree of protection to the electronics or input circuitry 224 of the medical device 204.

The novel lossy ferrite inductor concepts described herein will substantially raise both the inductance and resistivity at the MRI RF field frequencies. By raising the impedance of the implanted leadwire system 220, currents are reduced in the leadwires and also in the area of the pacemaker distal TIP electrode 226. The lossy ferrite inductor concept as described herein will further substantially reduce the susceptibility of both the active implantable medical device 204 and its associated leadwire systems 220 to the effects of MRI and other hospital diagnostic or surgical equipment.

Figure 21:
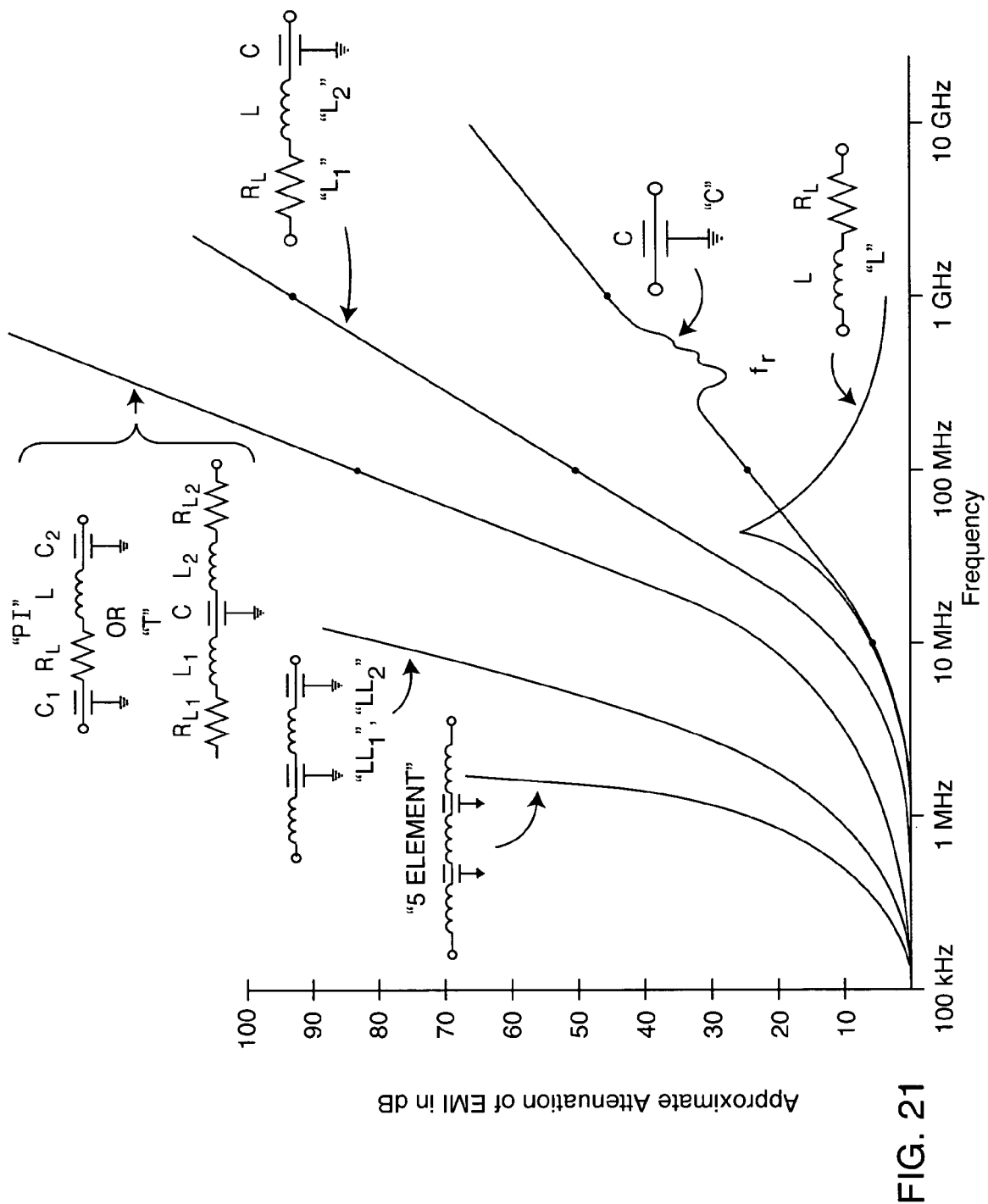
FIG. 21 illustrates attenuation slope curves for various low pass filter circuits.

The addition of the novel lossy ferrite inductor 200 increases the number of poles of the filter element. L, Pi, T, LL, 5 element and even n element circuits can all be realized. These circuits can have the lossy ferrite inductor 200 pointing toward the body fluid side of the system, towards the implantable medical device side of the system, or both. Increasing the number of poles, as previously described in U.S. patent application Ser. No. 10/825,900, increases the attenuation slope of the EMI filter as shown in FIG. 21. Accordingly, the novel lossy inductive ferrite concepts described herein not only raise the impedance of the leadwire system, but they also greatly improve the attenuation and effectiveness of the EMI filter installed at the input to the implantable medical device. As previously described in U.S. patent application Ser. No. 10/825,900, commonly used EMI filters are single pole devices consisting of a feedthrough capacitor and sometimes backed up by onboard rectangular MLCC chips. Adding multiple capacitor-inductor elements makes the feedthrough attenuation slope much steeper. Accordingly, this reduces the frequency at which the EMI filter starts to become effective (lowers its 3 dB point). Previous EMI filters offer effective attenuation at frequencies of 450 MHz and above. The novel multi-element EMI filtered feedthrough capacitor—inductor circuits described herein will create EMI filter circuitry that starts to become effective at 1 MHz and above. This is a substantial decrease in the frequency at which the EMI filter starts to become effective in comparison with the prior art.

This is not only important for MRI, lithotripsy and other diagnostic procedures. The patient environment is increasingly becoming more complex. New and more powerful emitters have recently been introduced to the marketplace, including cellular telephone amplifiers, high gain antennas for cellular telephones, cellular telephone jamming equipment, and both fixed and portable radio frequency identification (RFID) scanners and readers. These RFID scanners produce a very powerful (4 watts) digitally modulated field that is typically 13.56 or 915 MHz. Some systems work at other frequencies. Improved EMI filters as described herein will provide a much higher degree of immunity for the implantable medical device 204 from these new powerful emitters.

Also described are methods for preventing the lossy ferrite inductor 200 from saturating in the presence of extremely large DC, low frequency AC, and higher frequency RF fields. The present invention includes novel field cancellation effects due to the time difference of induced currents imposed in body fluid due to an incident electromagnetic field. The inventor has analyzed models of the complex permittivity of body tissue from various references. Wave propagation of high frequencies increases in body tissue thereby shortening the wavelength. This means that a substantial phase angle will occur between signals induced in the right ventricle leads as opposed to, for example, a biventricular lead placed outside the left ventricle. An example of these calculations is provided as follows:

Complex Permittivity:

$$\hat{\epsilon} = \epsilon_r' - j\epsilon_r''$$

Using the complex permittivity model for tissue from—S. Gabriel, R. W. Lau, and C. Gabriel, *The Dielectric Properties of Biological Tissues: III. Parametric Models for the Dielectric Spectrum of Tissues*.

$$\hat{\epsilon} = \epsilon_\infty + \sum_n \frac{\Delta\epsilon_n}{1+(j\omega\tau_n)^{(1-\alpha_n)}} + \frac{\sigma_i}{j\omega\epsilon_o}$$

Using the numbers for the above parameters for heart tissue, the calculated complex permittivity at 64 MHz is:

$$\hat{\epsilon} = 106.52 - j190.55$$

Therefore:

$$\epsilon_r' = 106.52$$

$$\epsilon_r'' = 190.55$$

The total conductivity from the tissue is the sum of the static ionic contribution, $\sigma_i$, and the alternating field conductivity, given by [1]:

$$\sigma_a = \omega\epsilon_o\epsilon_r''$$

$$\sigma = \sigma_i + \sigma_a = 0.7281 \text{ S/m}$$

The phase constant is calculated from the real part of the dielectric constant and the total conductivity by [1]:

$$\beta = \omega\sqrt{\mu\epsilon_o\epsilon_r'}\left\{\frac{1}{2}\left[\sqrt{1+\left(\frac{\sigma}{\omega\epsilon_o\epsilon_r'}\right)^2}+1\right]\right\}^2$$

$$\beta = 17.4120 \text{ rad/meter}$$

The wavelength and phase velocity are given by:

$$\lambda = \frac{2\pi}{\beta} = 0.454 \text{ meters}$$

$$v = \frac{\omega}{\beta} = 3.676 \times 10^6 \text{ meter/sec}$$

Assume that the separation in lead TIPs in an enlarged heart (congestive heart failure) is about 10 cm (~4 in), and convert the phase constant from radians/meter to degrees/meter:

$$\beta = 17.4120 \frac{\text{rad}}{\text{m}} \times \frac{180 \text{ deg}}{\pi \text{ rad}} = 997.6 \frac{\text{deg}}{\text{meter}}$$

$$997.6 \frac{\text{deg}}{\text{meter}} \times 0.1 \text{ meters} = 99.76 \text{ degrees phase difference}$$

Therefore the calculated phase difference between two points separated by 10 cm in heart tissue for an electromagnetic wave with a frequency of 64 MHz is approximately 99.76 degrees.

REFERENCES

1. C. A. Balanis, *Advanced Engineering Electromagnetics*, Wiley, 1989.
2. S. Gabriel, R. W. Lau, and C. Gabriel, "The Dielectric Properties of Biological Tissues: III. Parametric Models for the Dielectric Spectrum of Tissues", *Phys. Med. Biol.*, vol. 41, pp. 2251-2269 (1996).

The equations show that between the right ventricle and the left ventricle, an induced phase difference of 99.76 degrees can occur at a typical 64 MHz MRI pulsed RF field. This is a significant phase difference that can be used to reduce the core saturation effects in common inductors. This will be further described below. At other RF pulsed frequencies such as 128 MHz, the phase shifts will be even greater.

In many implantable medical devices 204, such as cardiac pacemakers, there are only leads implanted into one cardiac chamber. For example, single chamber bipolar pacemakers have one lead that drops into the right ventricle. Normally, this lead system consists of a TIP 226 which is embedded in myocardial tissue, and in a RING 228 which floats in the blood pool of the right ventricle. Sensing and pacing pulses are applied between TIP 226 and RING 228. Because of the close proximity of the TIP wire 230, which is surrounded by a spiral shaped RING wire 232, in a single chamber application there is little or no phase difference between the two leads as they are exposed to MRI signals. It is a novel feature of the present invention however, to route the leadwires 230, 232 that pass through the novel lossy ferrite inductor 200 in opposite directions. This produces field cancellation effects preventing the lossy ferrite inductor 200 from saturating.

Another inventive concept described herein is the presence of a cancellation antenna 234. This is a leadwire that exits the implantable medical device 204 and is routed in a different direction within the body tissue or venous system 222. For example, in the case of a cardiac pacemaker, leadwires are typically routed from either the left or the right pectoral muscle area into the subclavian vein and routed down through the vasculature into the bottom of the right ventricle. During this procedure it would be relatively easy for the surgeon to also route an additional leadwire across the top of the subclavian vein in the opposite direction. This will allow for maximum separation distance between the implanted leadwires thereby causing a maximum phase shift at the input to the cardiac pacemaker. This would also create additional field cancellation effects within the lossy ferrite inductor 200 as described herein.

The performance of any magnetic material will be degraded if it is operated under large DC or low frequency AC biases (MRI produces both of these effects). Under small bias conditions, increasing the applied magnetomotive force H applied to a magnetic core device includes a corresponding increase in magnetic flux B in the core. At some value of H, the magnetic flux B stops increasing. Increasing H beyond this value results in a rapid decrease in the permeability of the inductor. For this condition, magnetic theory terms the device "core saturated," as it is unable to support further increases in magnetic flux with increasing magnetomotive force input. When the slope of the B-H curve becomes nearly flat, which means it is in saturation, the instantaneous permeability (equal to the slope at the operating point) of the core will drop to a value of approximately one, or that of free space. However, even under this condition, the lossy ferrite inductors 200 have desirable lossy characteristics at EMI frequencies. When at saturation, the core will provide little noise attenuation. To attenuate MRI, it is important that the lossy ferrite inductor 200 maintain a large lossy impedance (ohmic loss). Using the novel concepts described herein, lossy ferrite inductors 200 designed to have a high resistive component may be used effectively even in the presence of a large low frequency magnetomotive force input.

In the description of the drawings which follows, functionally equivalent components among the various embodiments will be designated by the same reference number.

Figure 1:
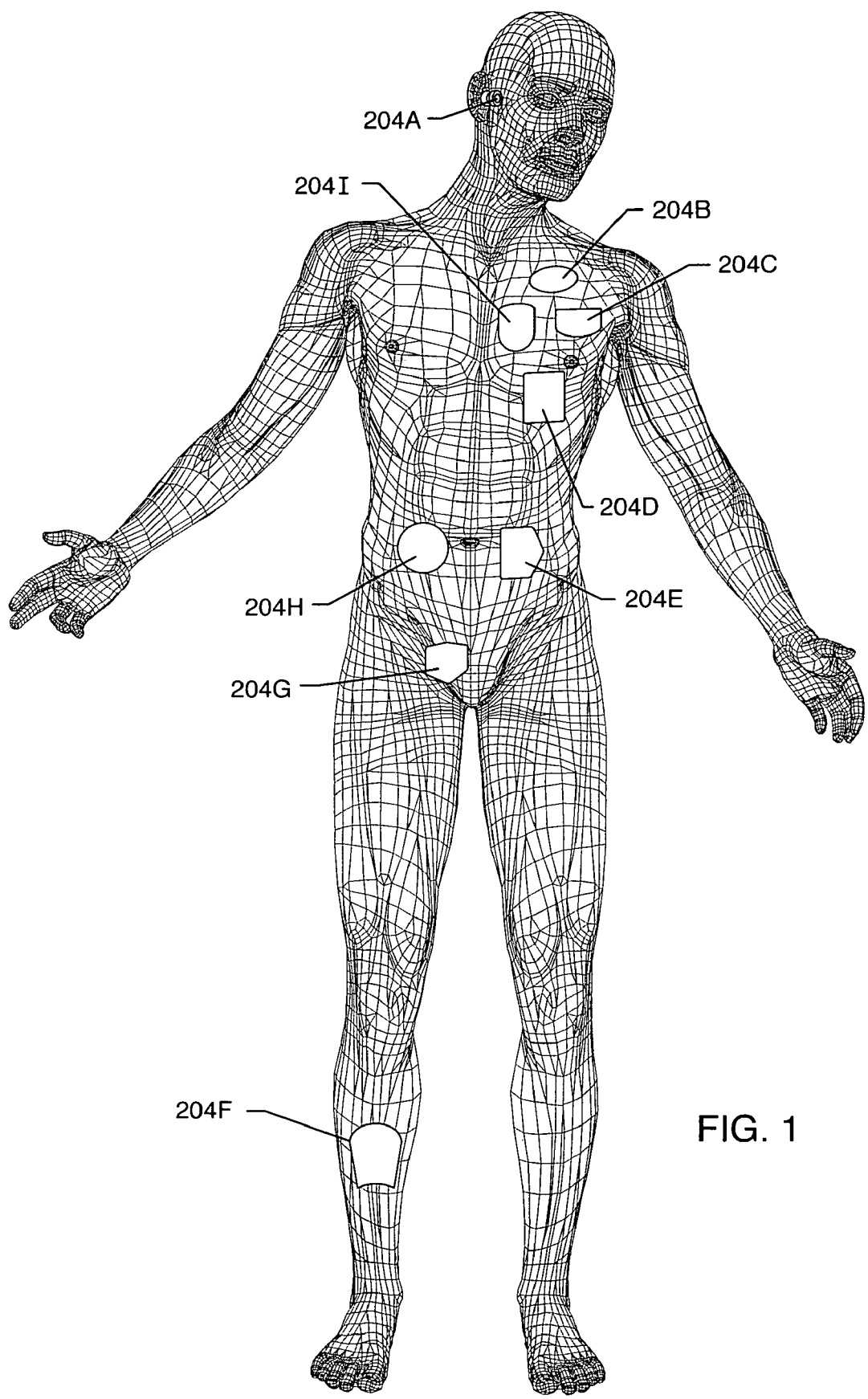
FIG. 1 is a schematic illustration of a human body illustrating various types of active implantable medical devices (AIMD's) currently in use.

FIG. 1 is an example of the various types of active implantable medical devices 204 that currently in use. FIG. 1 is a wire formed diagram of a generic human body showing a number of implanted medical devices. 204A is a family of hearing devices which can include the group of cochlear implants, piezoelectric sound bridge transducers and the like. 204B includes an entire variety of neurostimulators and brain stimulators. Neurostimulators are used to stimulate the vegas nerve for example to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. 204C shows a cardiac pacemaker which is well-known in the art. 204D includes the family of left ventricular assist devices (LVAD's), and artificial hearts, including the recently introduced artificial heart known as the Abiocor. 204E includes an entire family of drug pumps which can be used for dispensing of insulin, chemotherapy drugs, pain medications and the like. 204F includes a variety of bone growth stimulators for rapid healing of fractures. 204G includes urinary incontinence devices. 204H includes the family of pain relief spinal cord stimulators and anti-tremor stimulators. Insulin pumps are evolving from passive devices to ones that have sensors and closed loop systems. That is, real time monitoring of blood sugar levels will occur. These devices tend to be more sensitive to EMI than passive pumps that have no sense circuitry. 204H also includes an entire family of other types of neurostimulators used to block pain. 204I includes a family of implantable cardioverter defibrillators (ICD) devices and also includes the family of congestive heart failure devices (CHF). This is also known in the art as cardio resynchronization therapy devices, otherwise known as CRT devices.

Figure 2:
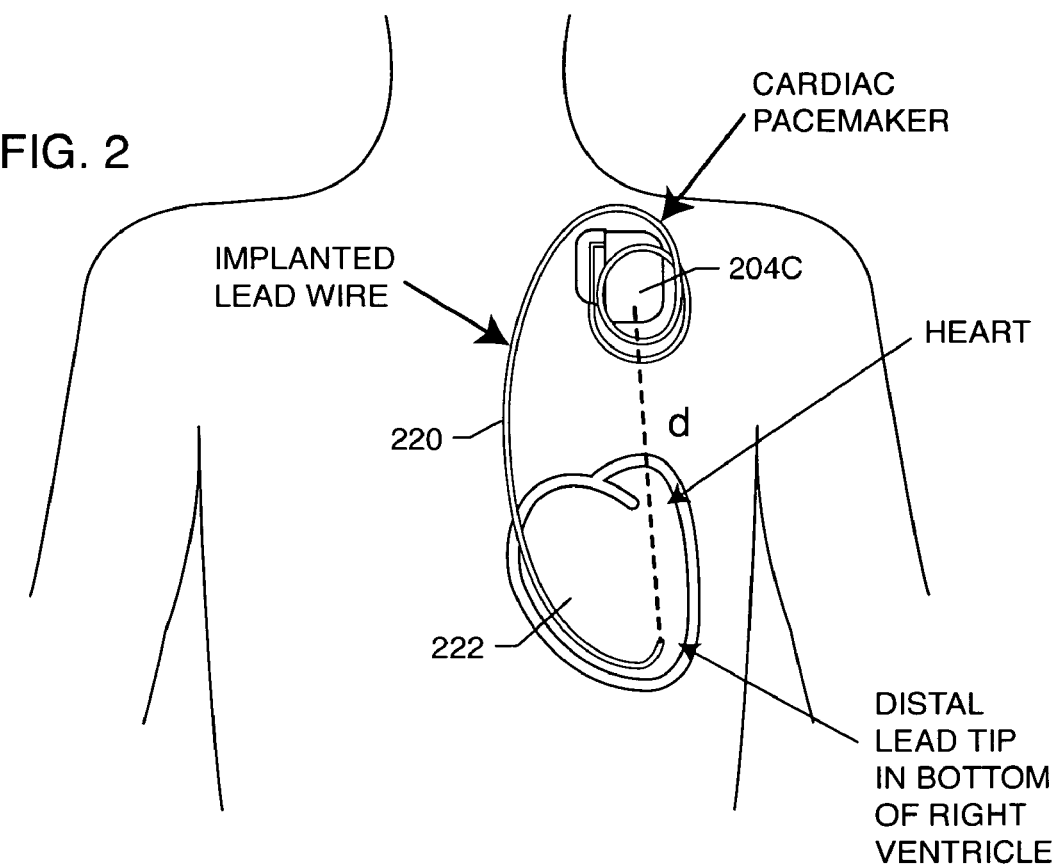
FIG. 2 is a schematic illustration of a unipolar pacing leadwire system for a cardiac pacemaker, wherein the pacing lead acts as an antenna to EMI (effective antenna length equals "d")

FIG. 2 is an illustration of a unipolar leadwire system for a cardiac pacemaker 204. Pacing pulses are delivered through the leadwire system 220 to the right ventricle of the heart. In a unipolar system, the leadwire TIP which is placed in the myocardial tissue 222 in the ventricle produces a pulse. The return is to the titanium can of the cardiac pacemaker 204C which one can consider as ground. This completes the electrical circuit. Unfortunately, this leadwire can also act as a very effective antenna, which can pick up stray electromagnetic signals. The type of antenna configuration illustrated in FIG. 2 is generally effective for electric fields. The pulsed RF field, which is generated by the body coil or head coil of an MRI, generally has both magnetic and electric field components.

Figure 3:
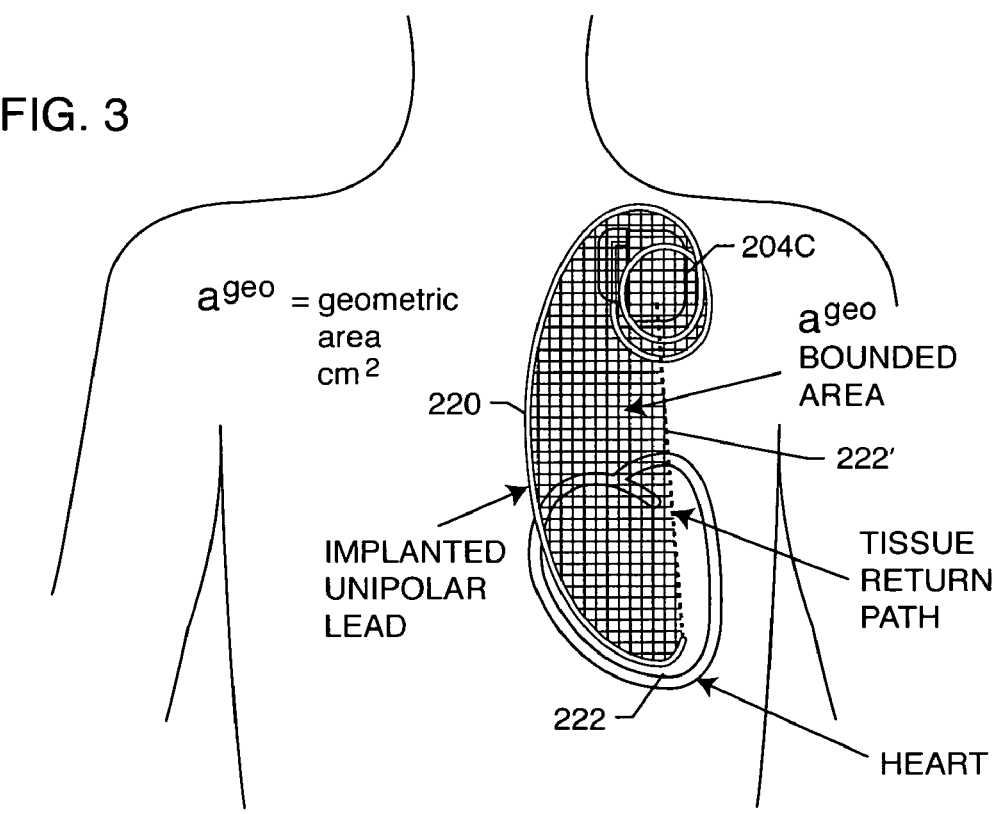
FIG. 3 is a schematic illustration of a bounded loop area of the leadwire system shown in FIG. 2, showing loop area(s) bounded by a unipolar pacing lead which couples with time-varying magnetic fields.

FIG. 3 illustrates a bounded loop area of the leadwire system 220 shown in FIG. 2. This bounded loop area is how coupling from magnetic fields can induce currents in the leadwire system 220. This comes from Faraday's Law of Induction. As one can see from FIG. 3, the leadwire system 220 does not form a complete loop. The bounded area is enclosed by the conductive leadwire system on the left and is returned through body tissue 222' on the right. Body tissue, of course, is a high reluctance path which thereby reduces the magnetic field coupling efficiency.

Figure 4:
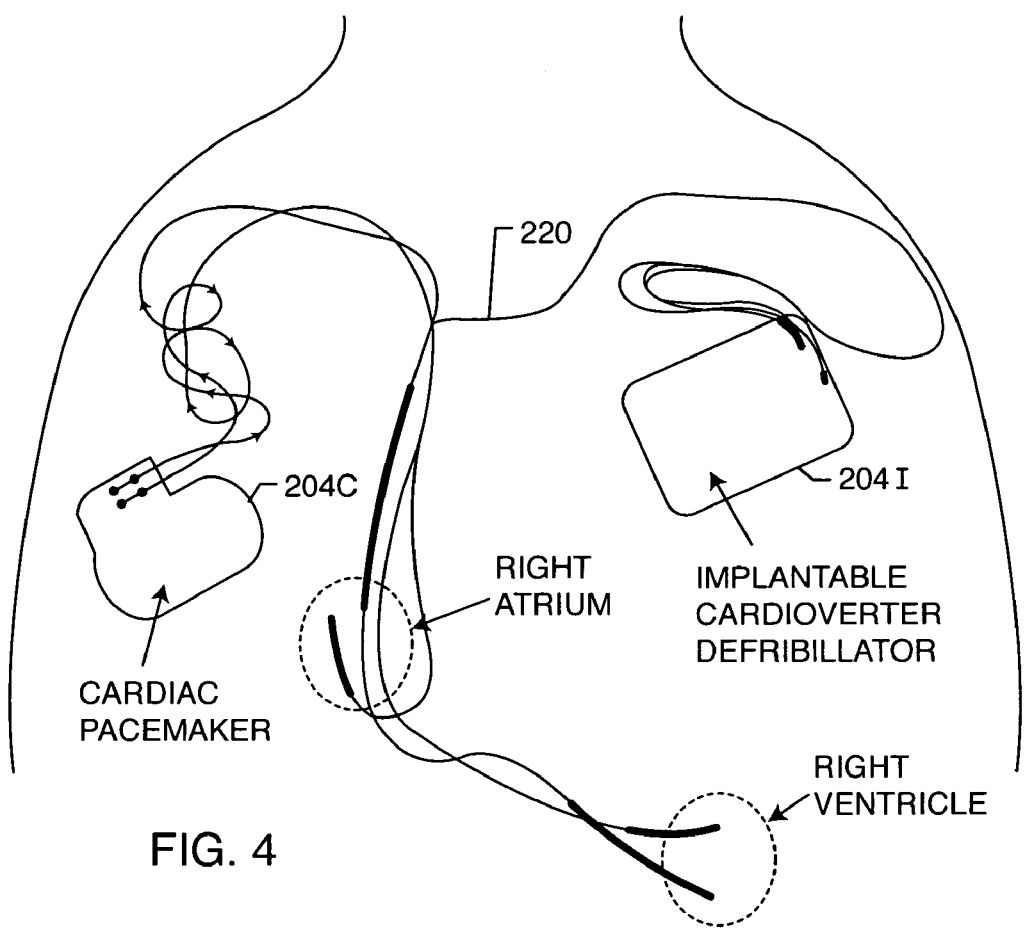
FIG. 4 is a tracing of a patient X-ray having both a pacemaker and a cardioverter defibrillator.

FIG. 4 is a very complicated tracing of an actual patient X-ray. This particular patient required both a cardiac pacemaker 204C and an implantable cardioverter defibrillator 204I'. The corresponding leadwire system 220, as one can see, makes for a very complicated antenna and loop coupling situation. The reader is referred to the article entitled "Estimation of Effective Lead Loop Area for Implantable Pulse Generator and Implantable Cardioverter Defibrillators" provided by the AAMI Pacemaker EMC Task Force.

Figure 5:
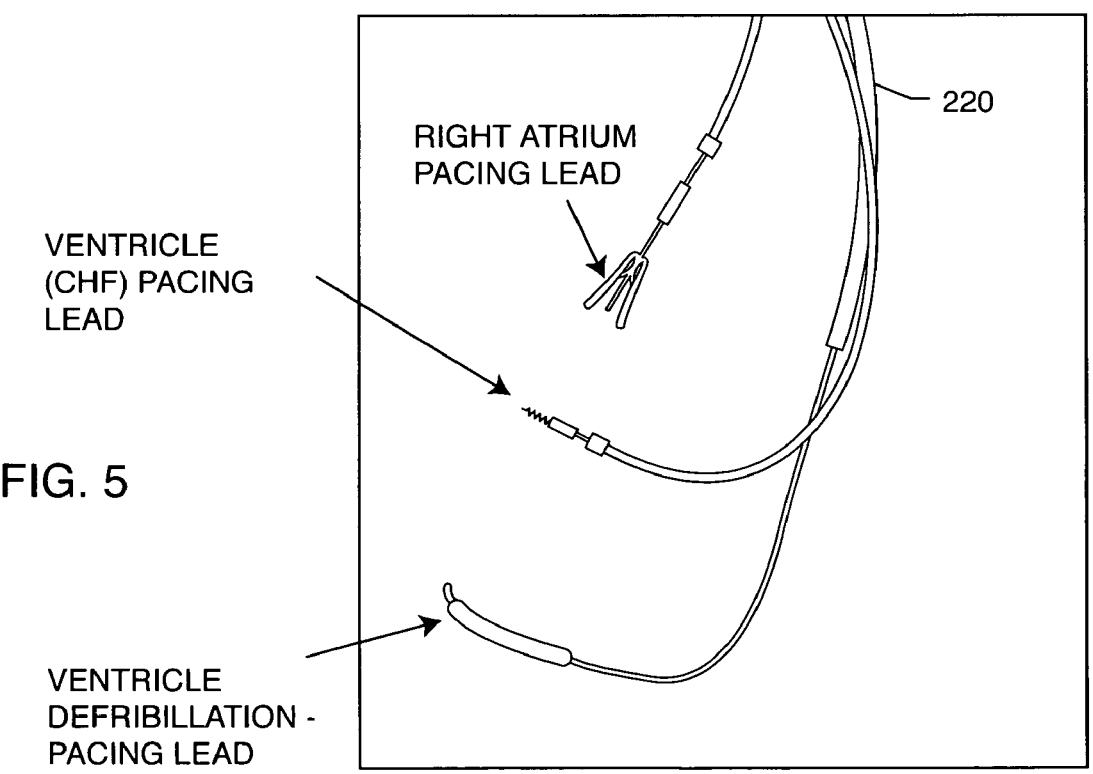
FIG. 5 is a line drawing of an X-ray of a bi-ventricular leadwire system implanted to treat congestive heart failure (CHF)

FIG. 5 is a line drawing of an actual patient cardiac X-ray of one of the newer bi-ventricular leadwire systems. The new bi-ventricular systems are being used to treat congestive heart failure. This represents the first time that it has been possible to implant leads outside of the left ventricle. This makes for a very efficient pacing system; however, the leadwire system 220 is quite complex. When a leadwire system 220, such as those described in FIGS. 2, 3, 4 and 5 are exposed to a time varying electric or magnetic field, electric currents can be induced into the leadwire systems.

Figure 6:
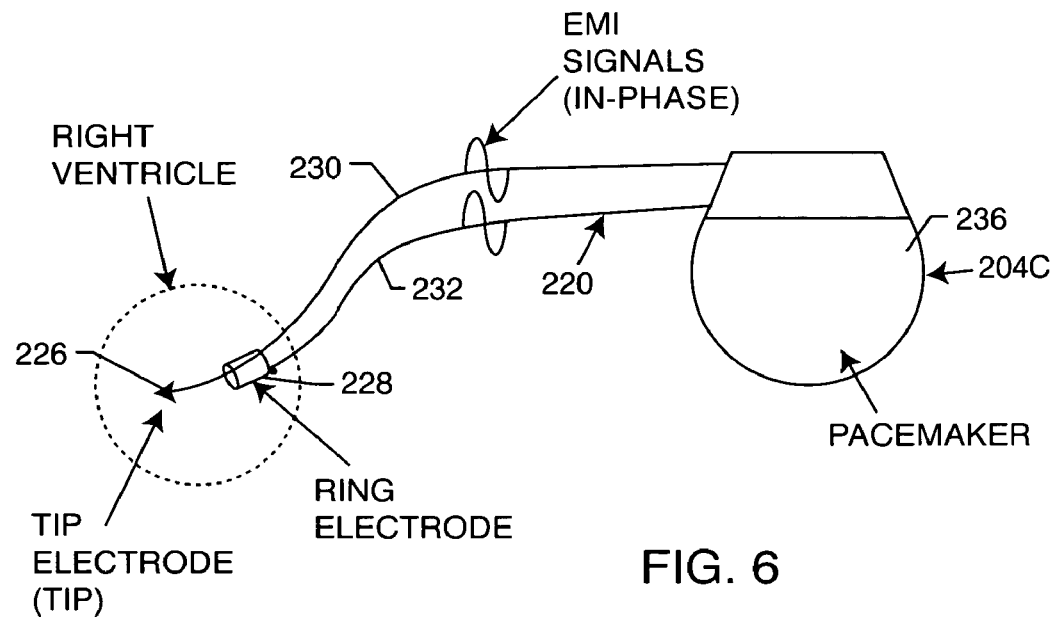
FIG. 6 illustrates a single chamber bipolar pacemaker leadwire system.

FIG. 6 illustrates the leadwire system 220 of a single chamber bipolar pacemaker 204C. In this case, the pacemaker housing or can 236 is neutral. Two leadwires are routed in very close proximity to each other down into the right ventricle as shown in FIG. 6. The TIP electrode 226 is implanted into myocardial tissue. Generally speaking, the RING electrode 228 floats in the ventricle blood pool and represents the return path. One can think of the TIP 226 as being positive and the RING 228 as being negative for a particular point in the pulse. When this leadwire system 220 is exposed to an external electric or magnetic field, EMI signals can be induced into the leadwire system. However, due to the close spacing of the two leadwires 230, 232, the induced EMI signals tend to be of the same phase and also the same amplitude. In this situation, an MRI can induce high currents into the leadwire system 220. As will be explained later, it would be desirable to raise the impedance of the leadwire system 220 and thereby minimize the induced current.

Figure 7:
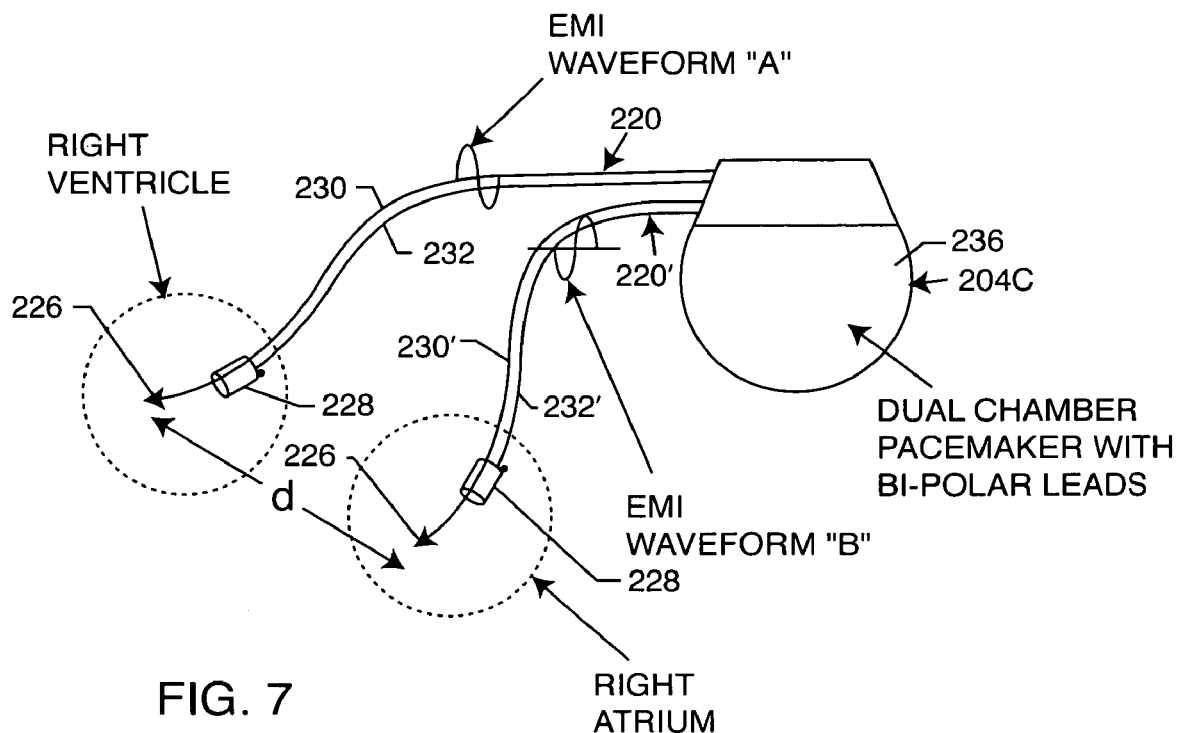
FIG. 7 is an illustration to similar to FIG. 6, illustrating a dual chamber leadwire system.

FIG. 7 illustrates a dual chamber leadwire system 220 and 220' using the same type of bipolar leadwires 230, 232 and 230', 232' as described in FIG. 6. In this case, one of the leads is implanted into the right ventricle and the other lead is implanted into the right atrium. As previously described for FIG. 6, the voltages induced into the right ventricle (RV) leads would tend to be of similar amplitude and phase. When one now examines the two leadwires (230', 232') that go to the right atrium, the same thing is true. The EMI signal induced on each lead will tend to be of similar amplitude and phase. However, when one compares the right ventricle EMI signal to the right atrium EMI signal, there can be a substantial difference in phase and amplitude. This is because of the variable separation distance, d, as shown in FIG. 7. As the incident electric or magnetic field passes through as a wave front, there is a time difference due to the spacing or separation distance, d. This has the effect of inducing voltages and currents in the leadwire systems 220 and 220' that are no longer in phase. Referring once again to FIG. 7, one can see that EMI waveform A is going through a maximum amplitude positive portion of the sine wave while at the same time, the waveform B is going through a correspondingly negative portion of its sine wave. This, of course, represents an extreme and unlikely situation where the two EMI signals would actually cancel each other at the input to the dual chamber pacemaker.

Figure 8:
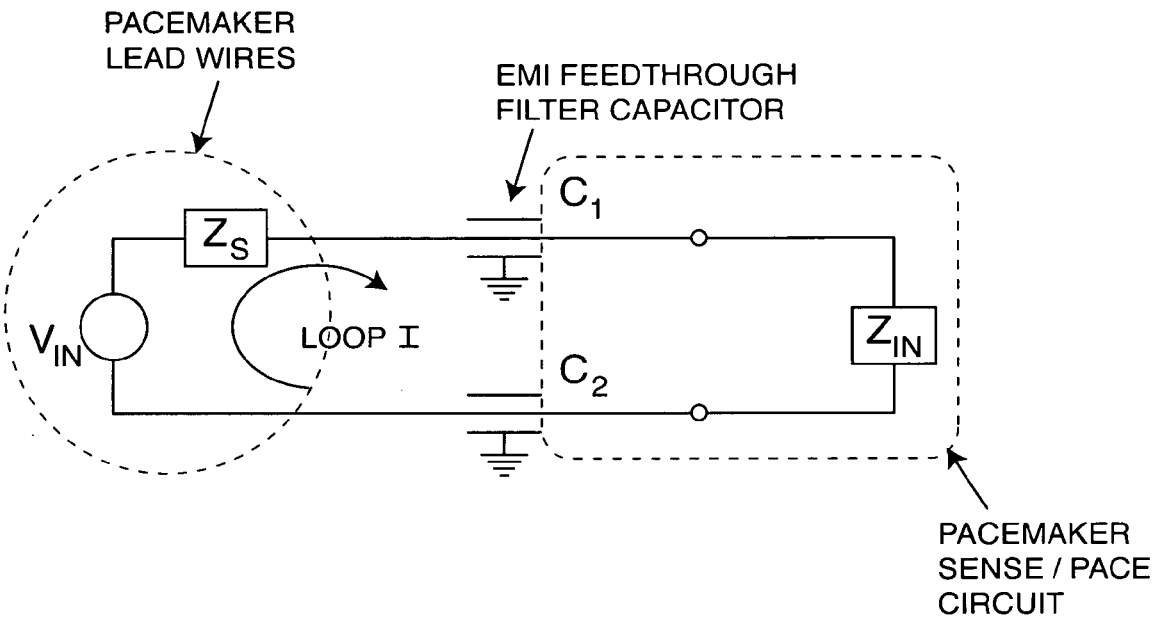
FIG. 8 is a schematic drawing illustrating an input impedance and coupling model for a single chamber pacemaker with bipolar leads.

FIG. 8 is a schematic diagram representing the input impedance and coupling model for a single chamber pacemaker with a bipolar leads. $V_{in}$ is the induced MRI or EMI noise voltage, which can be induced by electric or magnetic field coupling into the pacemaker leadwire system. The pacemaker lead system source impedance is shown as $Z_s$. $Z_{in}$ represents the pacemaker circuit input impedance. $C_1$ and $C_2$ are prior art feedthrough capacitor EMI filters.

Figure 9:
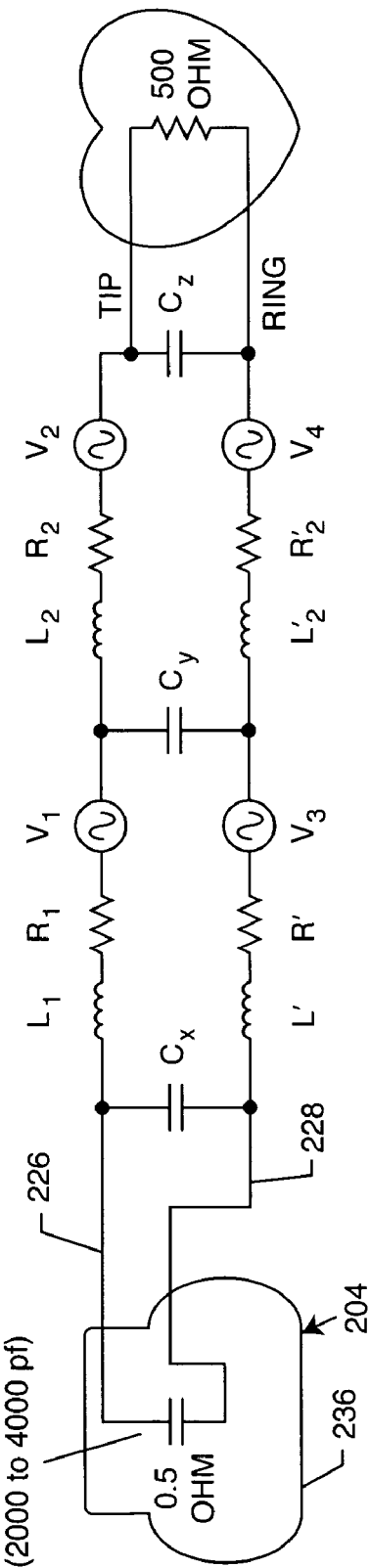
FIG. 9 is an electrical schematic illustration of a distributed element model for a typical bipolar leadwire system for a cardiac pacemaker.
Figure 10:
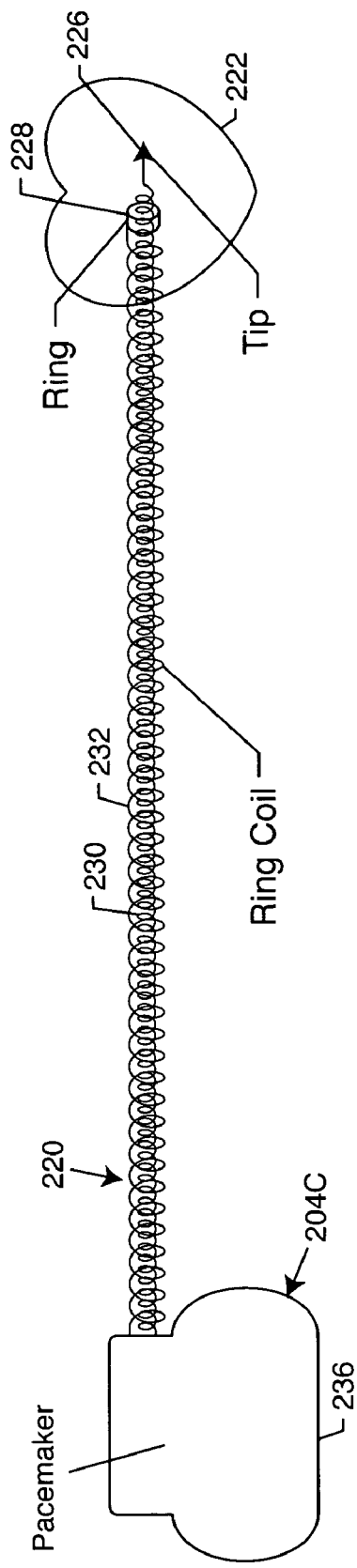
FIG. 10 is a mechanical schematic illustration of the bipolar leadwire system of FIG. 9.

FIG. 9 is the schematic of a distributed element model for a typical bipolar leadwire system for a cardiac pacemaker such as that shown in FIG. 10. The distributed capacitance $C_x$, $C_y$ and $C_z$ ( ... $C_n$) tend to be quite low in value (just a few picofarads), accordingly, the pacemaker input impedance ($X_c$ of the feedthrough) becomes an important current conduction path at MRI RF field frequencies. In FIG. 9, 236 is the titanium housing of the cardiac pacemaker 204C. The 0.5 ohms represents the capacitive reactance of a typical EMI filter feedthrough capacitor at a 64 MHz MRI pulse field frequency (ref. U.S. Pat. No. 5,333,095 and others). The heart, shown to the right, presents an approximate 500 ohms impedance at RF frequencies. This does vary from individual to individual, but 500 ohms is a good average value. The inductance elements $L_1$ and $L_2$ shown in series with the TIP leadwire are representative of the fact that this inductance is distributed along the entire length of the lead. In other words, this would be more accurate if this were broken up into $L_1, L_2, L_3, L_4 \ldots, L_N$. The same is true of the typically coiled RING connection wire consisting of $L_1'$ and $L_2'$. A better representation would be $L_1'$, $L_2'$, $L_3'$ ... $L_N'$. In a like manner, $R_1$ and $R_2$ are really distributed along the entire length of the TIP lead 230 and as well, $R_1'$ and $R_2'$ are distributed along the entire length of the RING lead 232. For the TIP wire, the total resistance value is about 70 ohms. Referring now to the RING lead, the total resistance is typically about 140 ohms. This is because the RING connection wire 232 is typically coiled about the TIP wire 230 and is thereby longer. Also shown in parallel between the TIP and RING leadwires are $C_x$, $C_y$ and $C_z$ which represents the distributed capacitance along the length of the bipolar leadwire. As before, a more accurate distribution is $C_x, C_y, \ldots C_n$. Also shown are a number of voltage sources $V_1$, $V_2$, $V_3$ and $V_4$. These represent distributed EMFs in the leadwire that arise when the MRI field(s) couples with the implanted leadwire system. There is a current that flows in this loop that results from the EMFs and loop impedance. Raising the value of the pacemaker input impedance from 0.5 ohms to a higher value would tend to reduce the loop current. Accordingly, using novel techniques as described herein, additional resistance and inductive reactance at the point of pacemaker leadwire(s) ingress and egress is a desirable feature.

FIG. 10 mechanically illustrates the bipolar leadwire system 220 of FIG. 9 that connects an implanted cardiac pacemaker 204C to cardiac tissue 222. The pacer is typically implanted into either the right or the left pectoral muscle area. The surgeon first constructs a tissue pocket. A special guide wire is then inserted which pierces the subclavian vein. The bipolar leadwire is then routed through the subclavian vein down through the aortic arch conveniently into one of the chambers of the heart. Typically, a conventional bipolar lead will be implanted in either the right ventricle, the right atrium, or both. The bipolar leadwire has been designed to withstand millions and millions of mechanical motions as the heart beats. Typically, the bipolar leadwire consists of an inner coil 230 which connects to the TIP electrode 226 at the distal end and an outer coil 232 which is wound around the inner coil and connects to the RING electrode 228. The TIP 226 is typically implanted directly into myocardial tissue, for example, the tissue in the bottom of the right ventricle. The RING 228 is placed at some distance from the TIP 226 and is insulated from it. The RING 228 typically floats in the blood pool in the ventricle. Biological electrical signals are sensed between TIP and RING. In addition, electrical pulses from the pacemaker 204 are delivered by the bipolar leads and are imposed across the TIP 226 and RING 228 which stimulates myocardial tissue 222 (beat pulse). In the configuration shown in FIG. 10, this would be typical of a pacemaker lead as opposed to an implantable defibrillator lead. The system shown in FIG. 10 is typically programmable wherein the lead can act as a unipolar system wherein the RING becomes inactive and the pacing and/or sensing are between TIP 226 and the pacemaker metal housing 236.

Referring to FIG. 10, one can see the outer coil 232 and the inner coil 230. As one develops electrical models of the leadwire system 220 it should be noted that because of its larger diameter, the outer coil 232, if it were stretched out in a straight line, would be longer than the inner coil 230. This means that typically the resistance and inductance due to the leadwire of the outer coil 232 will be higher of that of the inner coil 230. The distributed capacitances that forms between the outer coil 232 and the inner coil 230 is through a dielectric insulation which keeps the inner coil and the outer coil in electrical isolation.

Figure 11:
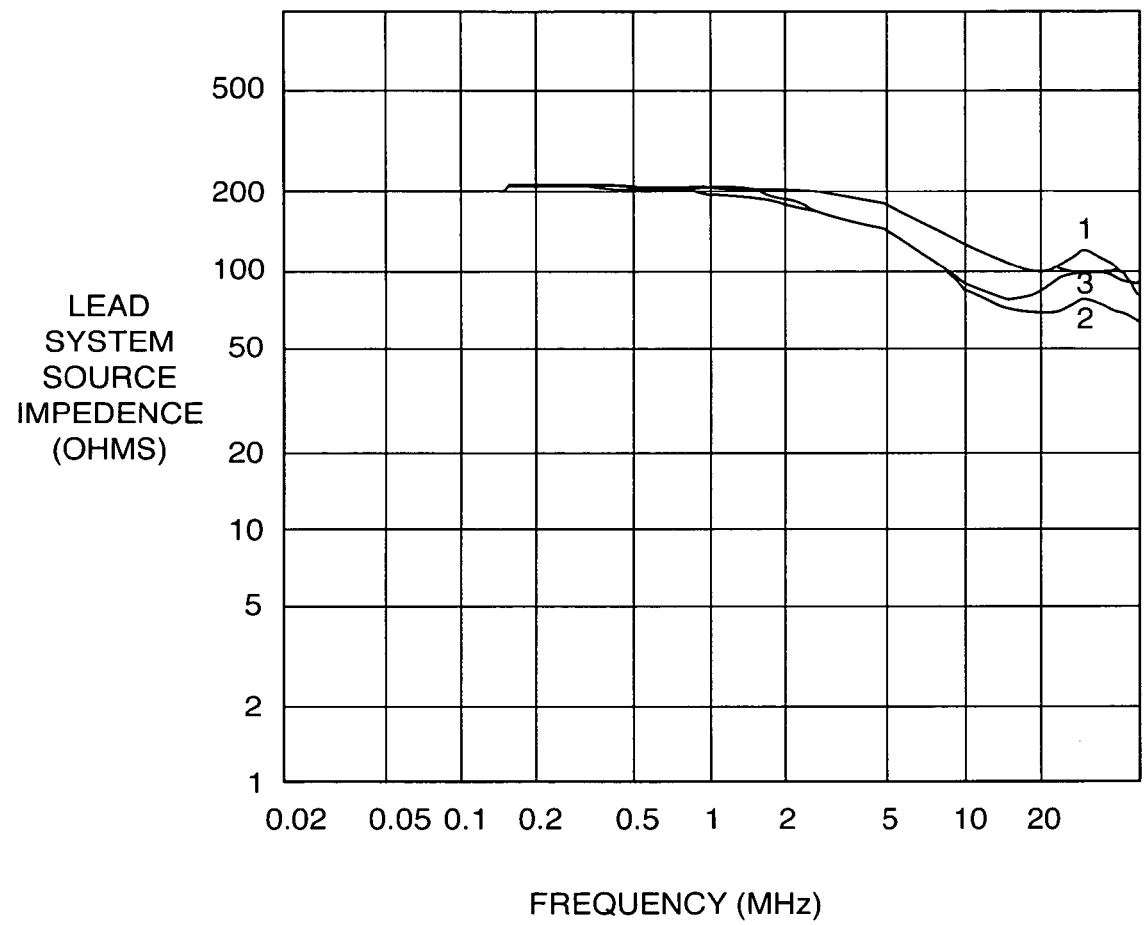
FIG. 11 is an illustration of a family of curves relating to the absolute source impedance of various implanted unipolar leads.

Referring now to FIG. 11, one can see a family of curves from a researcher named Dr. Tobias Bossert in Germany. Dr. Bossert studied the absolute impedance of various implanted unipolar leads in 1987. At low frequency the leadwire impedance tends to be about 200 ohms and then drops into the area of around 80 ohms (on average) above 20 MHz.

Figure 12:
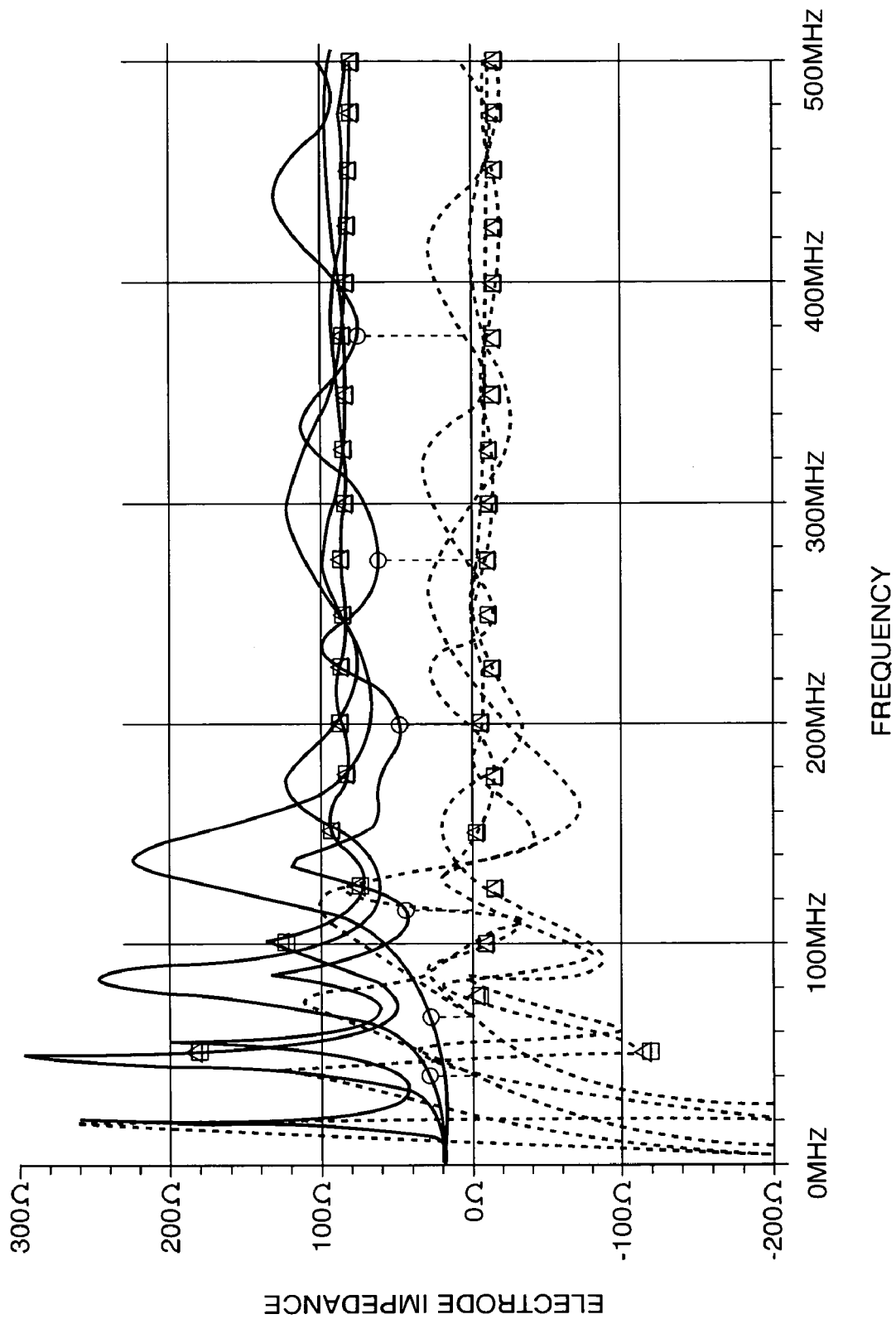
FIG. 12 is a graph showing complex impedance of various implanted leads (calculated)

FIG. 12 is the work from a researcher named Landsterfer in 1999. Dr. Landsterfer did this work at the University of Stuttgart in Germany. Dr. Landsterfer's work indicates that at low frequency the implanted leadwire impedance can vary significantly. At high frequency (above 200 MHz), the leadwire system tends to stabilize around 80 ohms.

Figure 13:
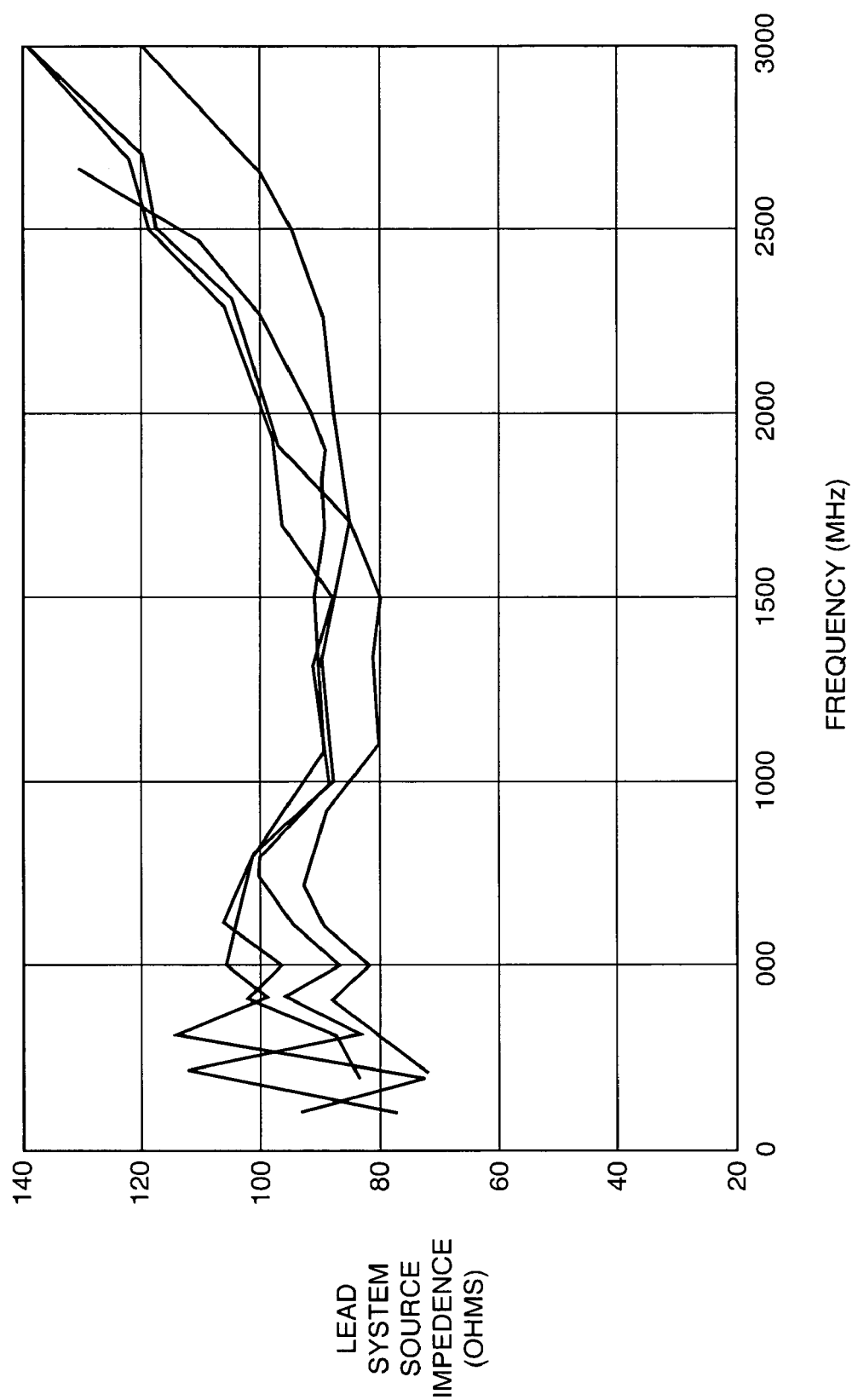
FIG. 13 is a graph showing absolute impedance of various implanted leads (calculated)

FIG. 13 is from work done by Hansen et al. in 1996. These researchers indicate that implanted leadwire systems vary from 80 ohms to about 120 ohms at low frequency and then start to increase in impedance at very high frequency. Referring now back to FIG. 8, as one can see from this simplified model, the current that would be induced in the loop due to exposure to a medical diagnostic procedure, such as MRI, would be the input voltage $V_{in}$ divided by the sum of the leadwire impedance $Z_s$, and the input impedance of the cardiac pacemaker $Z_{in}$. If $V_{in}$ is excessively high and/or the sum of $Z_s+Z_{in}$ is too low, then excessive loop current I can lead to excessive heating and tissue damage to the patient. Additionally, excessive loop current at high frequency can interfere with the proper operation of the cardiac pacemaker or implantable defibrillator due to electromagnetic interference effects. Accordingly, raising the pacemaker input impedance at selective frequencies is highly desirable, as that will tend to reduce the loop current and all of the aforementioned effects. One of the problems with raising the leadwire impedance is that it is highly undesirable to raise leadwire impedance at the biologic sensing frequencies or biological pacing frequencies. At these frequencies, pacemaker input impedance is kept relatively high. In general, cardiac biologic signals fall between the ranges of 20 to around 1000 Hertz. The most important part of this frequency range is from 20 to about 400 Hertz. If one were to significantly raise the impedance of the cardiac pacemaker leadwire system at these frequencies, this would make the pacemaker very inefficient. Pacing pulses would be degraded. In addition, sensing of biological signals would be attenuated. Accordingly, what is needed is a frequency selective device that will raise the input impedance of the cardiac pacemaker leadwire system or other active implantable medical device at selective frequencies while allowing biological frequencies to freely pass.

A way to accomplish this is with a ferrite bead 238 as shown in FIG. 14. The suppression performance of ferrite beads can be traced to their frequency dependent complex impedance. At lower frequencies, the impedance of the bead is primarily dominated by its inductive properties. At high frequencies, ferrite materials are dominated by their loss or resistive properties. A major disadvantage however, of the ferrite bead 238 as shown in FIG. 14, however, is twofold. That is, it has a relatively small diameter as shown in view 14A. When exposed to large time varying fields, such as those as produced in magnetic MRI, the bead material can saturate. When there is a magnetizing force H applied to ferrite materials, magnetic domains are lined up. Secondly, due to its small size and inefficient form factor, there is simply not enough material in the ferrite bead 238 to keep lining up magnetic domains indefinitely.

FIG. 15 illustrates the ferrite core saturation curve for the ferrite bead 238 of FIG. 14. As one increases the applied magnetizing force H to above the operating region, one reaches an area called core saturation. This is where the magnetic flux density B no longer increases. At this point, the ferrite material is doing no more good than the permeability of free space which is one. The performance of any magnetic material would be degraded if it is operated under a large DC or low frequency AC bias. Under small bias conditions, increasing the applied magnetomotive force H applied to a magnetic core device induces a corresponding increase in magnetic flux B in the core. However, at some value of H, the magnetic flux B stops increasing. Increasing H beyond this value results in a rapid decrease in the permeability of the device. For this condition, magnetic theory terms the device's core to be saturated, as it is unable to support further increases in magnetic flux with increasing magnetomotive force input.

This is a major problem with the extremely large fields induced during MRI procedures. A ferrite bead 238 of the type shown in FIG. 14 would saturate and become ineffective. Accordingly, the ferrite bead 238 would fail to do its job of raising the input impedance of the implantable medical device. For these reasons, the ferrite bead 238 of FIG. 14 is not a preferred embodiment of the present invention. As will be described, novel lossy ferrite slabs with a diameter to height ratio greater than 1.0 are the novel and preferred embodiment.

Figure 16:
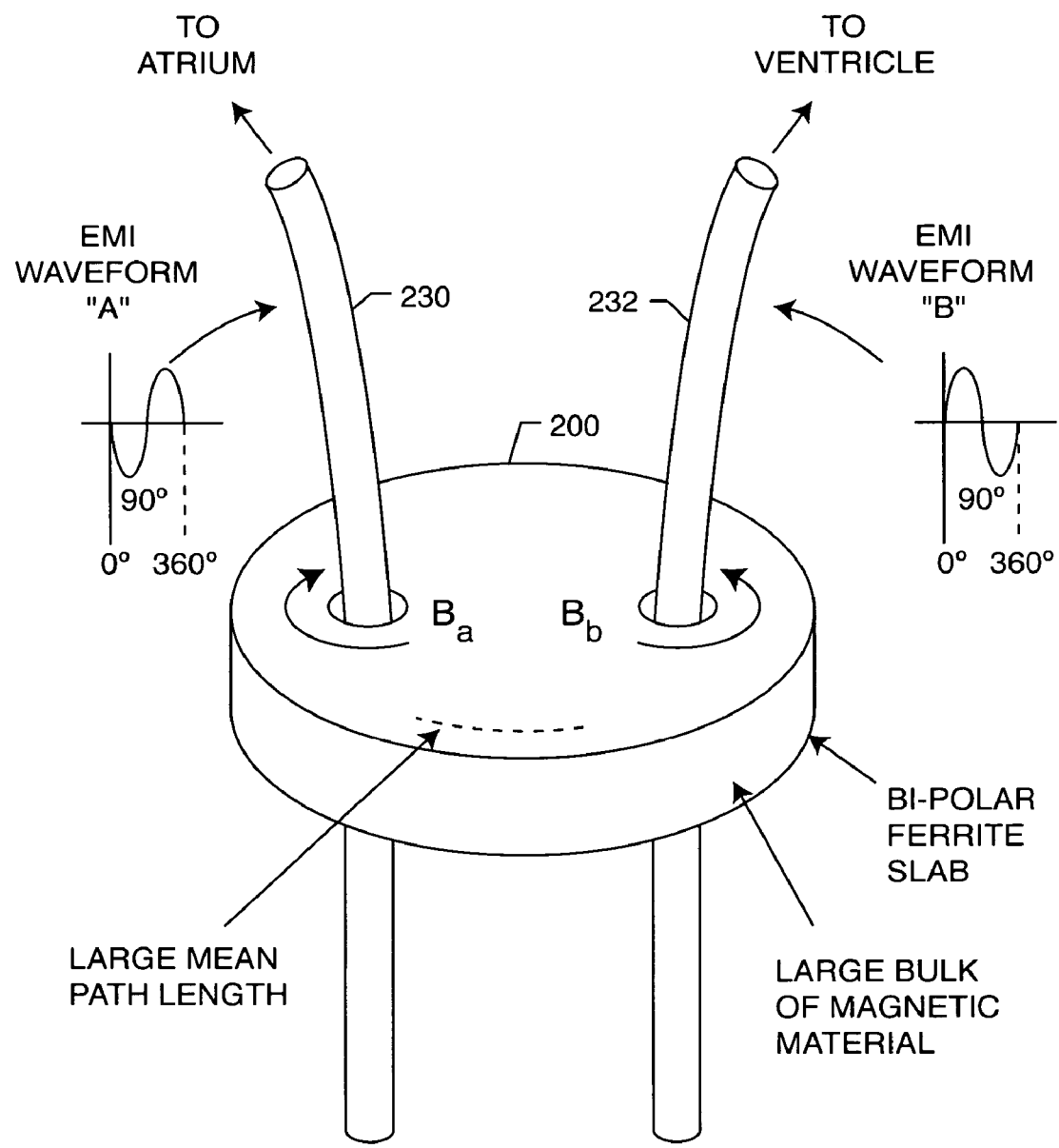
FIG. 16 illustrates a novel bipolar lossy ferrite slab inductor of the present invention, wherein out-of-phase signals create magnetic flux density cancellation.

FIG. 16 illustrates a novel bipolar lossy ferrite inductor 200 of the present invention. This is shown bipolar for illustrative reasons only. One skilled in the art will realize this could be quadpolar, hexpolar, octapolar or any other number of leadwires 230, 232. The important point is that by placing these leadwires 230, 232 that run to and from body tissue through a common lossy ferrite inductor 200, one can obtain field cancellation. One can see that the EMI waveform that is induced in leadwire 230 reaches a relative minimum at 90 electrical degrees. Referring now to leadwire 232, one can see that the EMI waveform goes through a relative maximum at 90 electrical degrees. These waveforms produce corresponding magnetizing forces $B_a$ and $B_b$ in the lossy ferrite inductor 200 as shown. However, these two applied magnetizing forces are induced in opposite directions thereby providing some degree of cancellation. If the waveforms as illustrated in FIG. 16 are of equal amplitude and out of phase as illustrated, complete cancellation will occur which would be highly desirable. However, in an actual application, this is unlikely to be the case. When one considers the complicated leadwire systems 220 of FIGS. 4 and 5, one can see that substantial cancellation will occur in the lossy ferrite inductor 200. This is a key feature of the present invention. Not only does the use of the lossy ferrite inductor 200 raise the input impedance of the implantable medical device due to the sheer bulk and increased path length of the ferrite material, but field cancellation can also occur when there are multiple leadwires. In summary, the lossy ferrite inductor 200 of FIG. 16 has four primary advantages over the discrete ferrite bead previously described in FIG. 14. The inductor 200 has a more efficient form factor, more magnetic material, a longer mean magnetic path length, and allows for magnetic flux cancellation so that it can operate in high field such as MRI.

Figure 17:
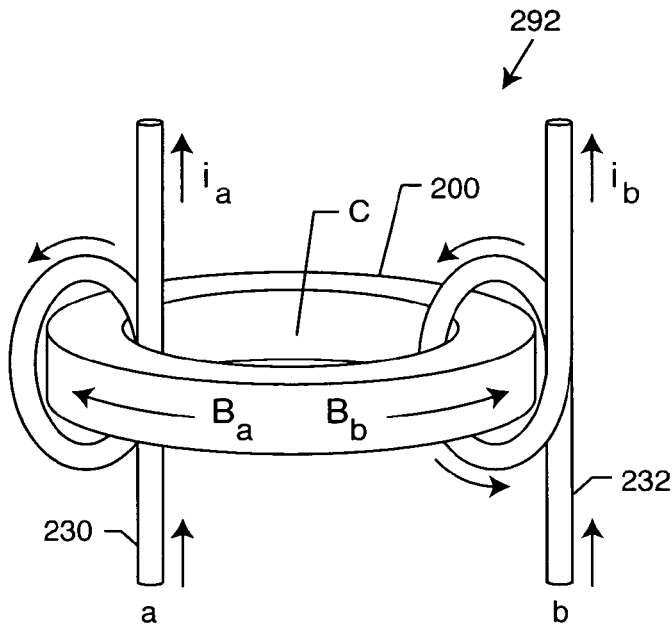
FIG. 17 is a perspective schematic illustration of a novel toroidal lossy ferrite inductor utilizing a high permeability ferrite core, and two leadwires wound in opposite directions.

FIG. 17 illustrates a novel toroidal lossy ferrite inductor 200 using a high permeability ferrite core. Other cores could be used, however, a high permeability lossy core is desired for an MRI application where the currents are very high and high frequency resistive/lossy dissipative elements are desired. The coil assembly 292 shown in FIG. 16 has two different leadwires a and b (230, 232), commensurate with those shown in the bipolar leadwire system in FIG. 9. In a medical implant application, FIG. 17 is novel in that as the leadwires 230, 232 come through the coil 200 they are wound in opposite directions. Assuming that the induced currents $i_a$ and $i_b$ shown in the leadwires a and b are in phase and are in the same vector direction, the opposite turn directions will cause 180 electrical degree out of phase flux density $B_a$ and $B_b$ in the core C.

Figure 18:
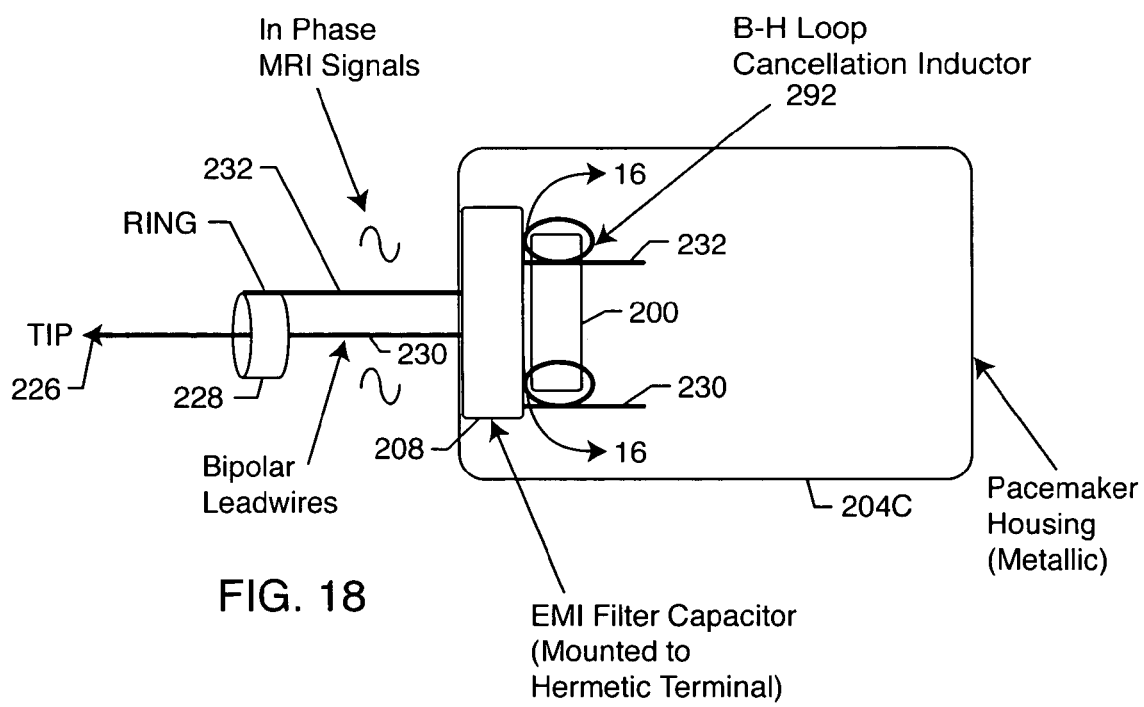
FIG. 18 is a schematic representation illustrating the toroidal inductor of FIG. 17 installed with the typical EMI filter capacitor of a cardiac pacemaker.

Referring now to FIG. 18, one can see the novel lossy ferrite coil assembly 292 of FIG. 17 shown installed in conjunction with the typical EMI filter capacitor of a cardiac pacemaker 204C. EMI filter capacitors 208 for cardiac pacemakers are well known in the art and are described by a number of existing patents, including U.S. Pat. No. 5,333,095. Referring once again to FIG. 17 the B-H loop cancellation lossy ferrite coil assembly 292 can be co-bonded to the EMI filter capacitor 208 as shown.

Figure 19:
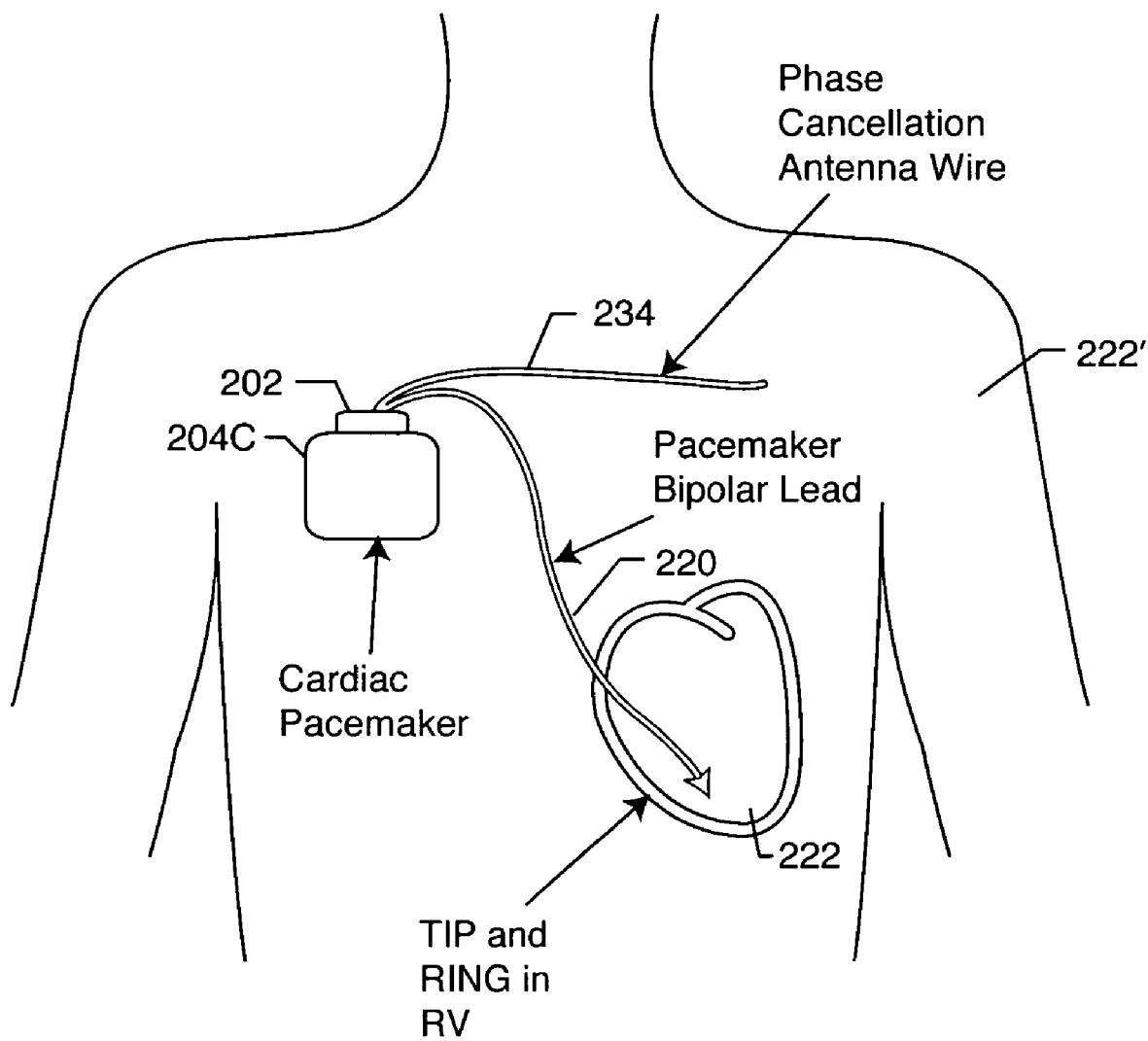
FIG. 19 is an outline drawing of the front view of a human torso showing a cardiac pacemaker having a novel phase cancellation antenna, that has been implanted in the right pectoral muscle area.

FIG. 19 is an outline drawing of the front view of a human torso showing a cardiac pacemaker 204C that has been implanted in the right pectoral muscle area. As is common in the art, a bipolar pacemaker leadwire system 220 has been threaded through the subclavian vein and down into the cardiac right ventricle. Shown is a novel phase cancellation antenna wire 234. This is an additional wire that egresses through the EMI filtered hermetic terminal 202 and the lossy ferrite inductor 200 of the cardiac pacemaker. This insulated unipolar leadwire 234 does not have a TIP or RING electrode and is not designed to connect to body tissue or fluid at all. It simply floats in the blood stream. The purpose of the phase cancellation antenna 234 is so that when an MRI field, such as that produced at 64 MHz, induces currents on both the right ventricle bipolar lead and the phase cancellation leadwires, those currents will be subject to additional phase shift. This is because of the velocity of propagation of the MRI electromagnetic wave through myocardial 222 and other body tissue 222' and the fact that the cancellation leadwire 234 is spaced further apart from the bipolar leadwire 220 that provides pacing and sensing to cardiac tissue. By having a wide and variable spacing between the cardiac leadwires 220 and the phase cancellation lead (antenna) 234, MRI currents that enter the pacemaker 204C will not be in phase. This is another novel way to use phase cancellation to avoid core saturation in the lossy ferrite inductor 200. This technique can be used as a stand alone feature or in combination with the other phase cancellation methods described herein (such as winding ferrite slab turns in opposite directions). It will be obvious to those skilled in the art that the phase cancellation antenna lead 234 can be placed in a variety of directions and locations in the venous system or even in body tissue 222. It will also be obvious that phase cancellation lead(s) can also be used in combination with atrium, left ventricle, cochlear, neurostimulator and a wide variety of other implanted leadwire systems.

Figure 20:
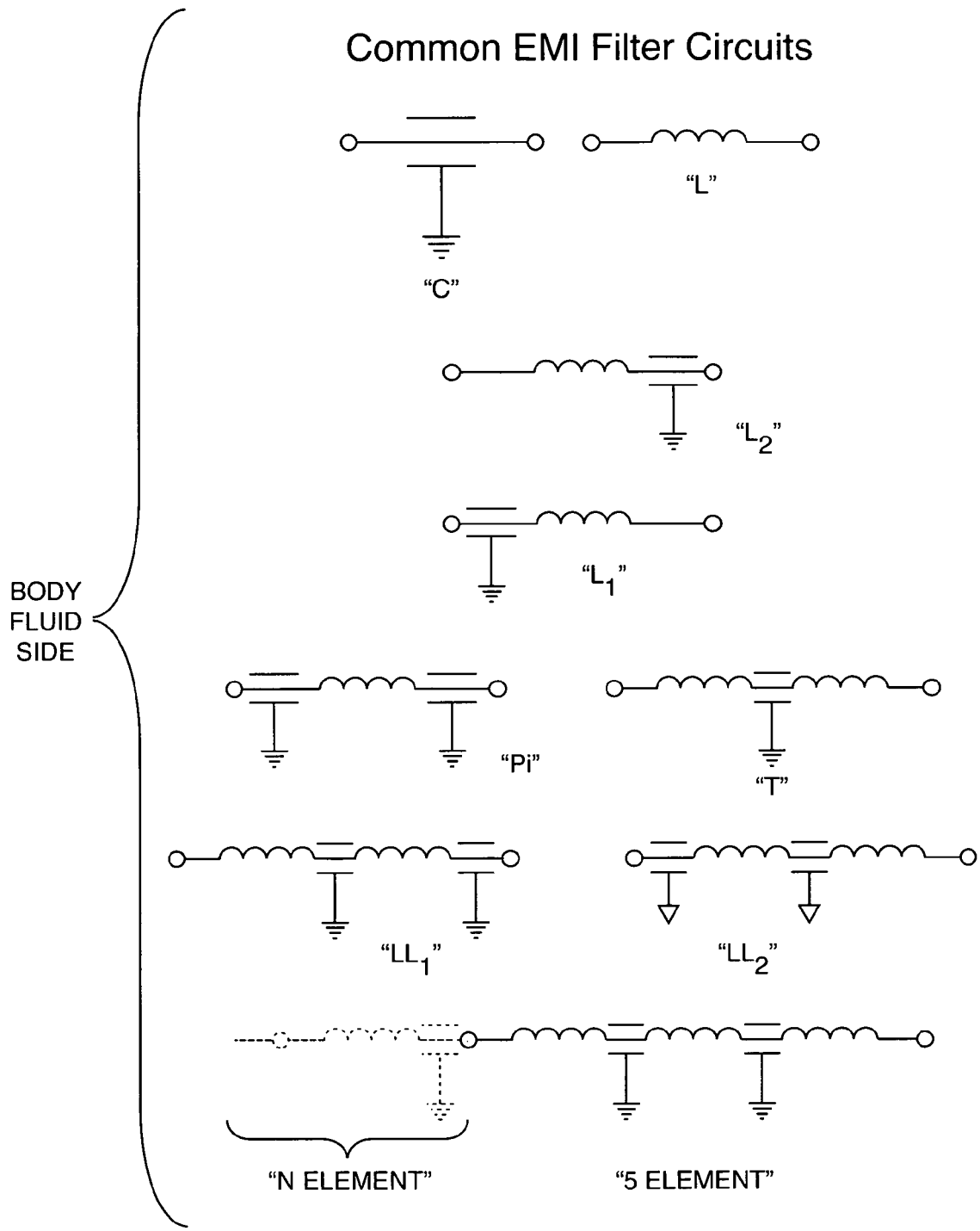
FIG. 20 illustrates electrical schematics for several low pass filter EMI filter circuits.

FIG. 20 shows common EMI filter circuits such as C, L, PI, etc. It is only the C circuit that has been in common use in cardiac pacemakers to date (U.S. Pat. No. 5,333,095 et. al.). The $L_1$, $L_2$, Pi, T, LL and 5 Element circuits are desirable low pass circuit configurations for use with either the novel lossy ferrite inductor or cancellation winding technology described herein.

FIG. 21 illustrates attenuation slope curves for various low pass filter circuits as previously described in U.S. patent application Ser. No. 10/825,900. Shown are the attenuation slopes for C, L, Pi, T, LL and 5 element EMI filters. As one increases the number of filter elements, the attenuation slope increases. That is, for a given capacitance value, one can achieve a much higher level of EMI attenuation. For MRI applications, particularly desirable configurations include the T or LL. The reason for this is that the added inductance and high frequency resistance also raises the cardiac lead system impedance. As illustrated in FIG. 9, increasing the lead system impedance reduces the MRI currents that circulate in the implanted leadwires. This will substantially reduce undesirable leadwire heating effects.

Figure 22:
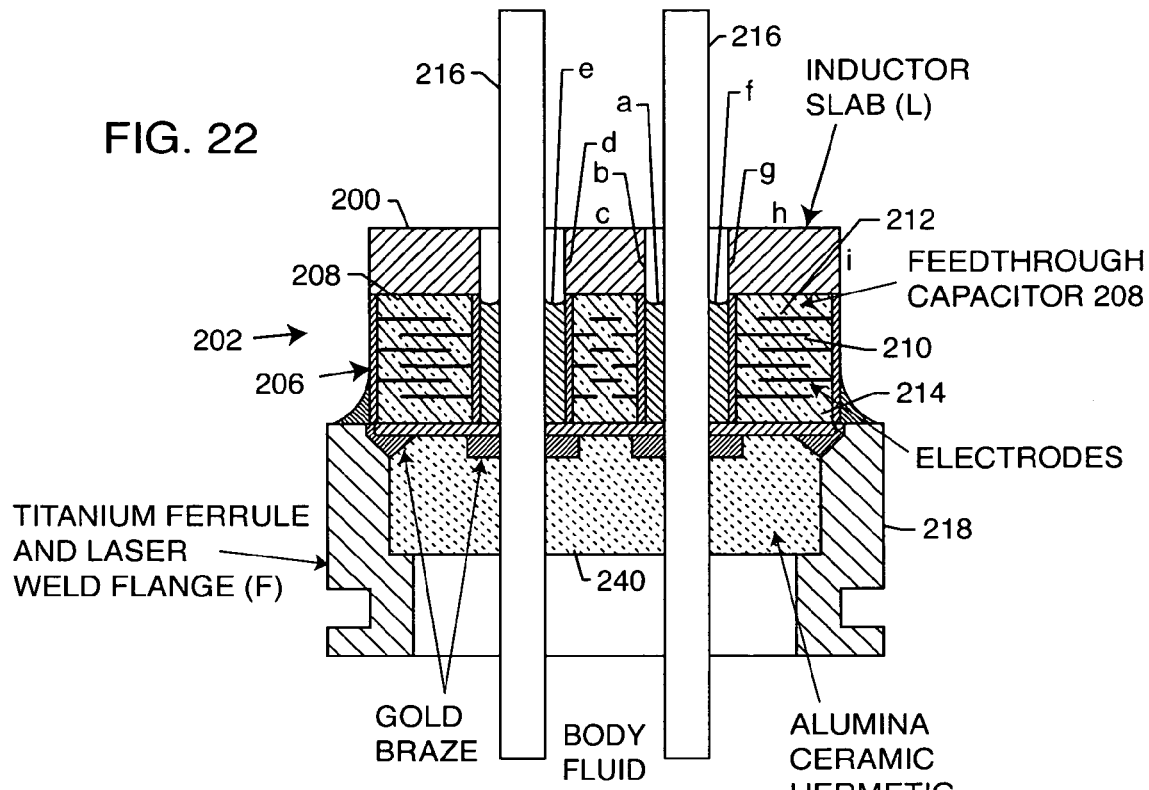
FIG. 22 is a cross-sectional view of a quad-polar hermetically sealed terminal with a feedthrough capacitor and a co-bonded lossy ferrite inductor forming an "$L_1$" circuit of the present invention.

FIG. 22 is a cross-sectional view of a quadpolar hermetically sealed terminal 202 with a co-bonded quadpolar feedthrough capacitor 208 and a quadpolar lossy ferrite inductor 200 of the present invention. Feedthrough capacitors 208 are well known in the art. However, feedthrough capacitors generally do not do much to improve the EMI immunity of cardiac pacemakers and implantable defibrillators to high power level hospital procedures, such as MRI. In fact, a large value feedthrough capacitor can actually act to make the MRI situation worse. Feedthrough capacitors work by making the input impedance of the cardiac pacemaker very low at EMI frequencies. However, as previously described, a low input impedance at MRI frequencies is exactly the wrong thing to have. The reason is that this would cause increased loop currents in the cardiac leadwires. A feedthrough capacitor of large value when exposed to MRI frequencies would look like a very low input impedance and tend to short out the input of the cardiac pacemaker or other active implantable medical device. This would indeed protect the internal electronics of the cardiac pacemaker, but it would also result in large loop currents in an implanted leadwire system. It has been shown in the literature that high loop currents can cause excessive heating either in the leadwires or at the TIP to RING electrode interface which can lead to patient tissue damage. These effects are described by Roger Christoph Luchinger, reference attachment DISS.ETH14665. Doctor Luchinger points out that if a cardiac pacemaker wearer is exposed to MRI, in certain cases the pacemaker capture level can increase after the MRI procedure. What this means is that the pacemaker may have to produce a much higher voltage in order to properly pace the myocardial tissue. Post mortem analysis has indicated that this increase in capture level was caused by tissue damage at the TIP to RING interface of the cardiac leadwire system.

Referring once again to FIG. 22, as one can see, it is the lossy ferrite inductor 200 that is the primary component of importance when attempting to raise the input impedance of the cardiac pacemaker at selected frequencies (such as 64 MHz).

Figure 23:
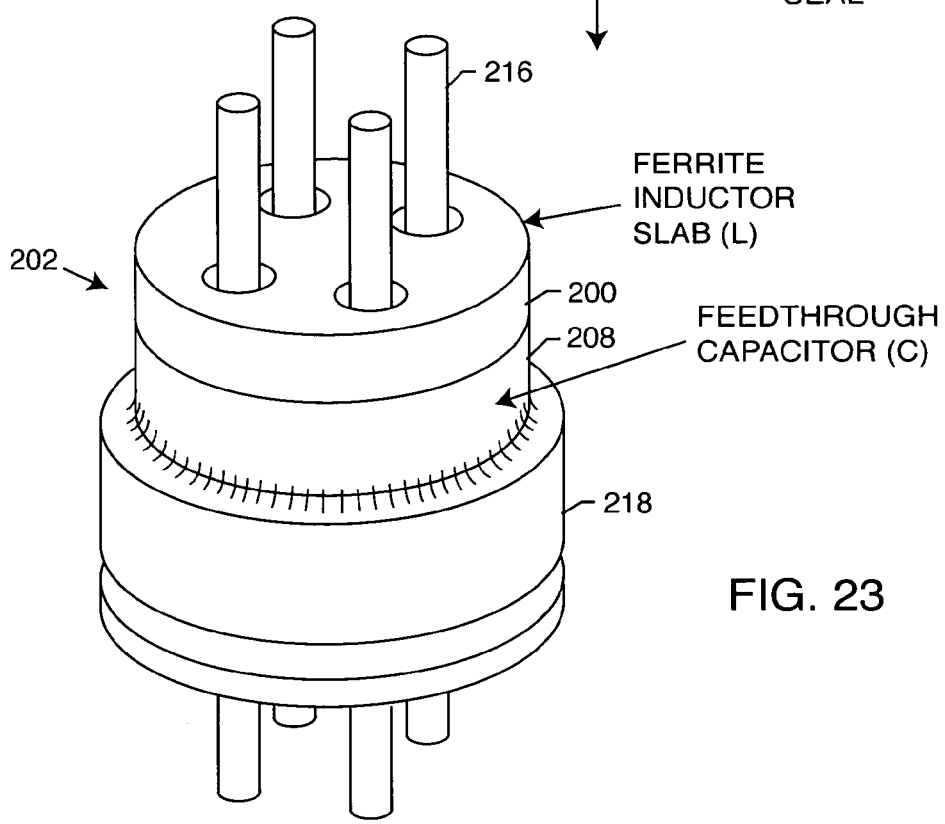
FIG. 23 is a top and side perspective view of the lossy ferrite inductor and feedthrough filter capacitor assembly of FIG. 22.

FIG. 23 is a perspective view of the quadpolar lossy ferrite inductor 200 and capacitor 208 of FIG. 22.

Figure 24:
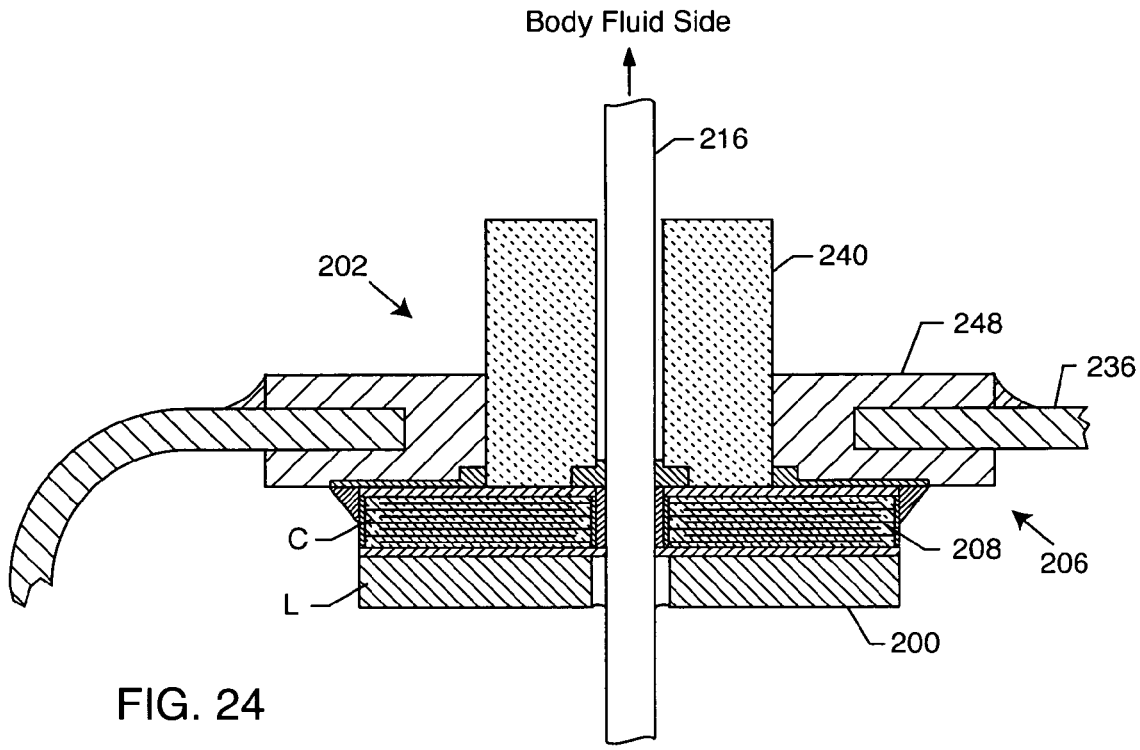
FIG. 24 is a cross-sectional view of a unipolar hermetic seal with attached feedthrough capacitor and lossy ferrite inductor.

FIG. 24 is a cross-sectional view of a unipolar hermetic terminal 202 with attached feedthrough capacitor assembly 206 including a lossy ferrite inductor 200.

Figure 25:
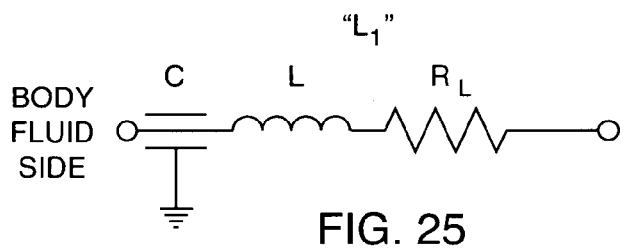
FIG. 25 is an electrical schematic diagram of the lossy "$L_1$" section ferrite slab EMI filter of FIG. 24.

FIG. 25 is the schematic diagram of the LC EMI filter of FIG. 24. The resistive element $R_L$ represents the lossy element of the lossy ferrite inductor which converts unwanted RF energy to harmless heat.

Figure 26:
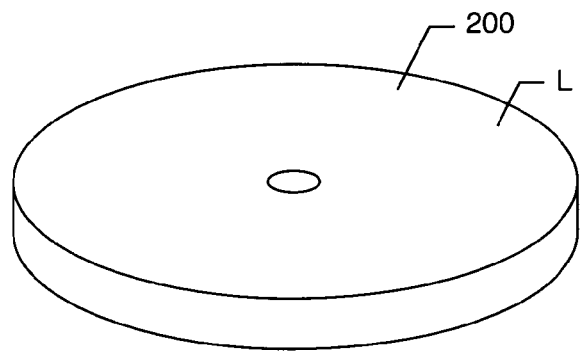
FIG. 26 is an isometric view of the lossy ferrite inductor of FIG. 24.

FIG. 26 is an isometric view of the lossy ferrite inductor 200 of FIG. 24.

Figure 27:
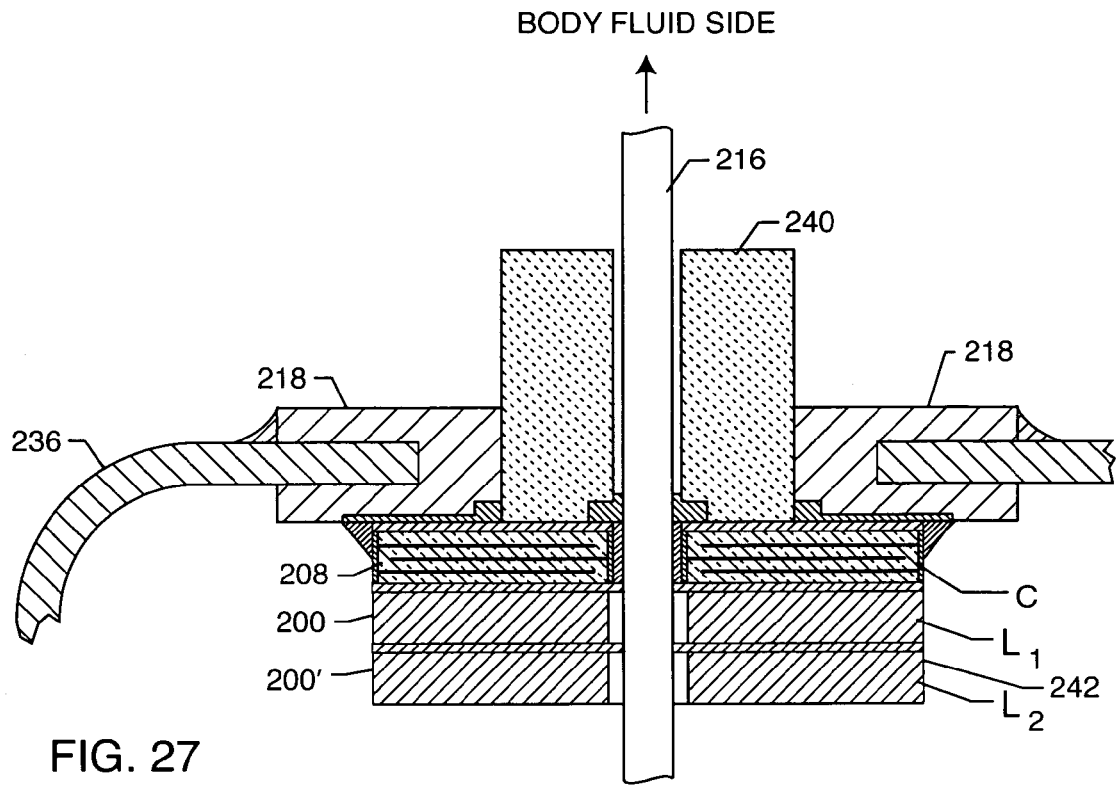
FIG. 27 is a fragmented sectional view similar to FIG. 24, showing a second lossy ferrite inductor added to the primary lossy ferrite inductor.

FIG. 27 illustrates the LC filter of FIG. 24 with a second lossy ferrite inductor 200' added to the primary lossy ferrite inductor 200. This illustrates the advantage of having a very thick lossy ferrite inductor 200 which increases the overall magnetic material and reduces its tendency to saturate in the presence of high applied magnetizing force H. As previously described in U.S. patent application Ser. No. 10/825,900, it is not necessary that ferrite material 200 be the same as ferrite material 200'. By using two different material compositions, one could optimize the impedance at MRI frequencies.

Figure 28:
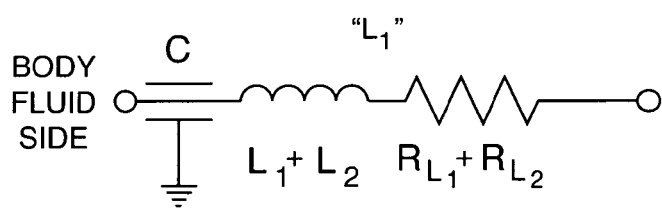
FIG. 28 is an electrical schematic diagram of the "$L_1$" filter shown in FIG. 27.

FIG. 28 is an electrical schematic diagram of the filter shown in FIG. 27.

Figure 29:
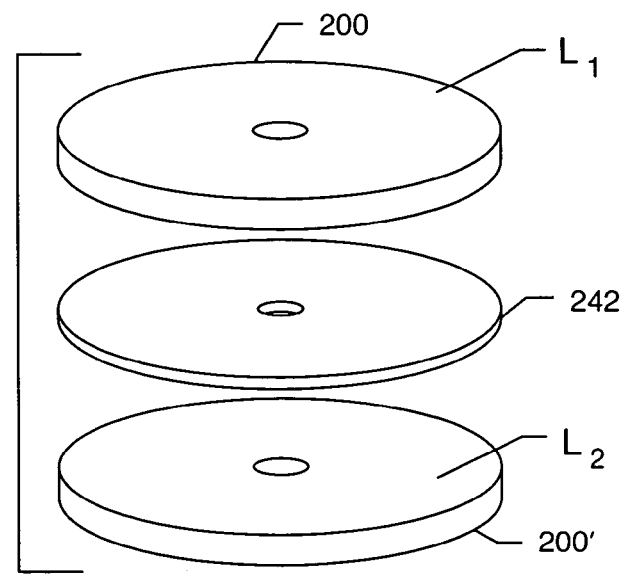
FIG. 29 is a perspective view showing the co-bonding of two lossy ferrite inductors of FIG. 27 with an intermediate washer.

FIG. 29 is a view showing the co-bonding of two lossy ferrite inductors L (200) and L' (200') utilizing a bonding washer 242. It will be obvious to one skilled in the art that these lossy ferrite inductors could be stacked up in 3, 4 or more layers.

Figure 30:
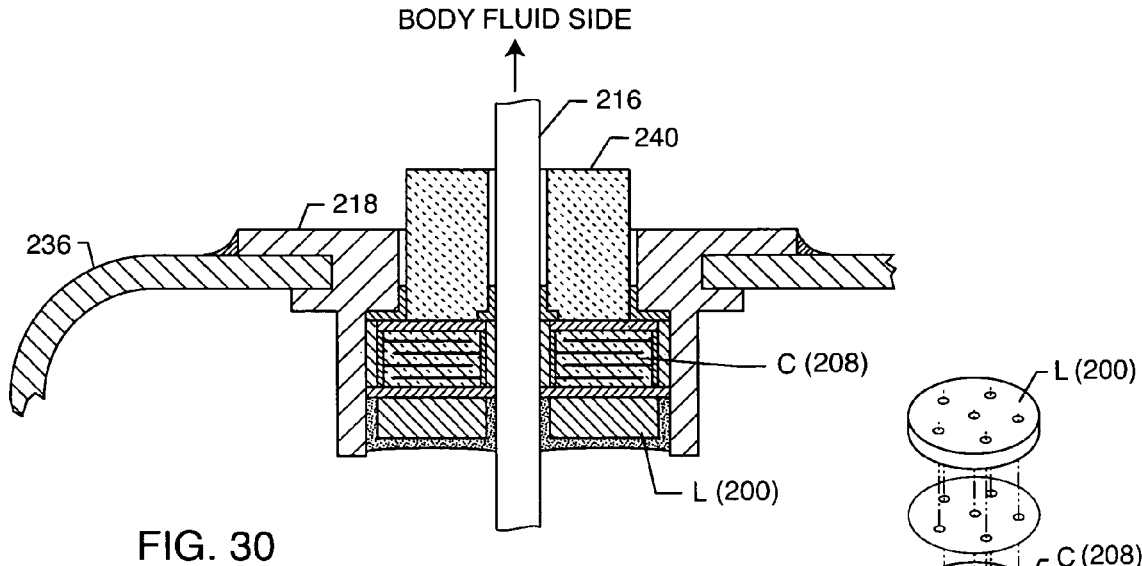
FIG. 30 is a fragmented sectional view similar to FIG. 24, illustrating an imbedded feedthrough capacitor with a co-bonded lossy ferrite inductor.

FIG. 30 illustrates an embedded feedthrough capacitor C with a lossy ferrite inductor L (200) shown co-bonded to it.

Figure 31:
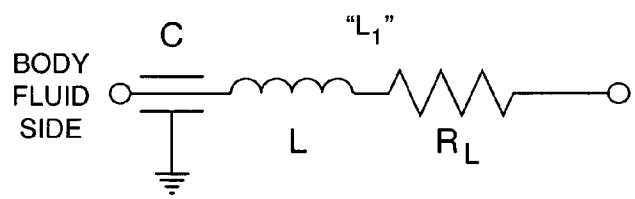
FIG. 31 is an electrical schematic diagram of the "$L_1$" assembly of FIG. 30.

FIG. 31 is the electrical schematic diagram of FIG. 30.

Figure 32:
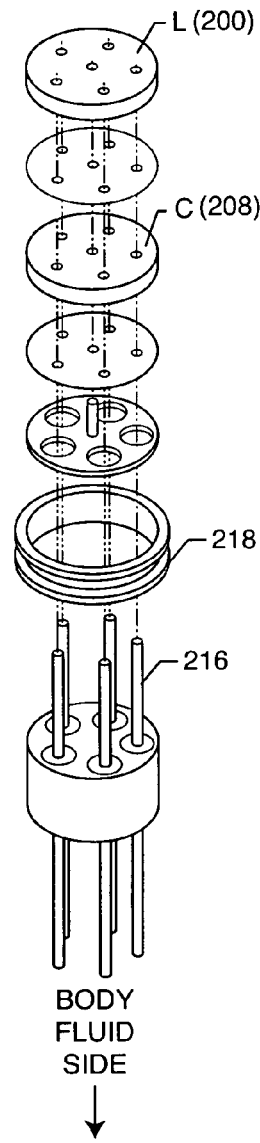
FIG. 32 is an exploded perspective view showing an internally grounded capacitor with five feedthrough wires and a co-bonded lossy ferrite inductor.

FIG. 32 is an exploded view showing an internally grounded capacitor C with five feedthrough wires 216 designed to go to cardiac tissue. Internally grounded feedthrough capacitors are well know in the art as described by U.S. Pat. Nos. 5,905,627 and 6,529,103. The lossy ferrite inductor L (200) is shown in position to be co-bonded to the feedthrough capacitor C. As previously described, the various signals induced on these five leadwires would tend to produce magnetic flux density (B) cancellation inside of the lossy ferrite inductor. This would allow the lossy ferrite inductor to continue to operate in the presence of very large fields, thereby effectively increasing the input impedance of the implantable medical device.

Figure 33:
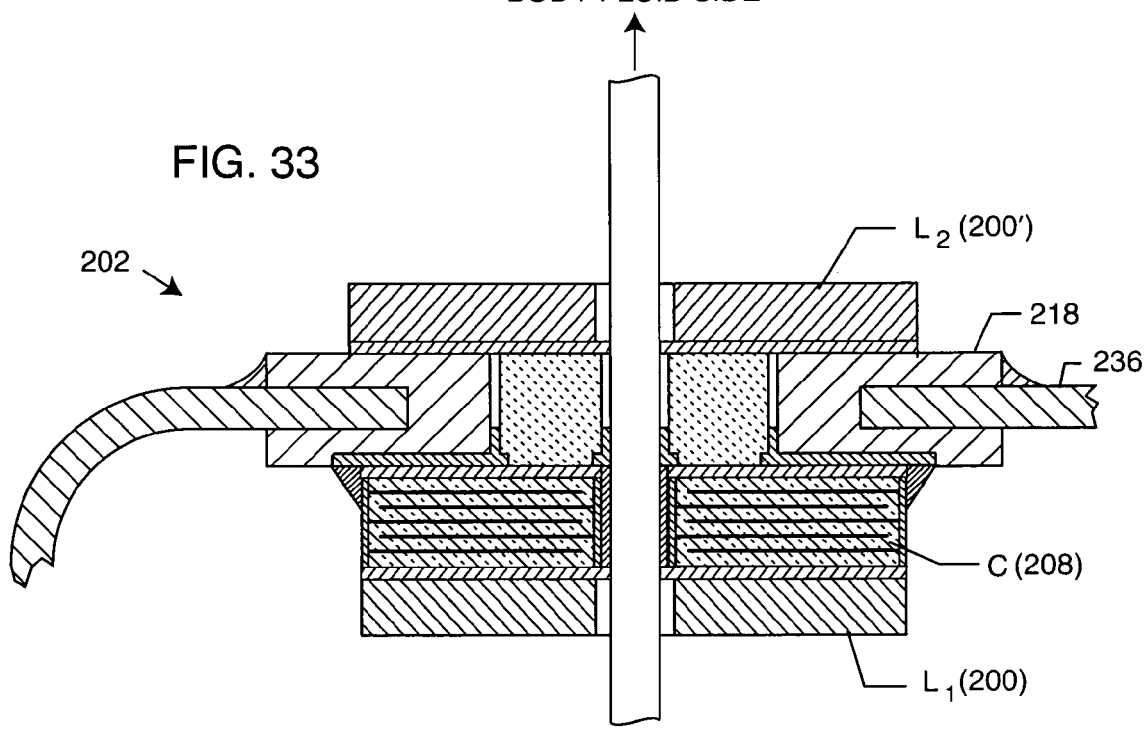
FIG. 33 is a fragmented sectional view similar to FIG. 24, illustrating a ferrite slab placed on the body fluid side of the hermetic terminal.

FIG. 33 illustrates a lossy ferrite inductor $L_2$ (200') placed on the body fluid side of the hermetic terminal 202. In addition, there is a second ferrite slab $L_1$ (200) placed on the opposite side of the feedthrough capacitor C (208) towards the internal electronics. This makes for what is known in the art as a T-section filter.

Figure 34:
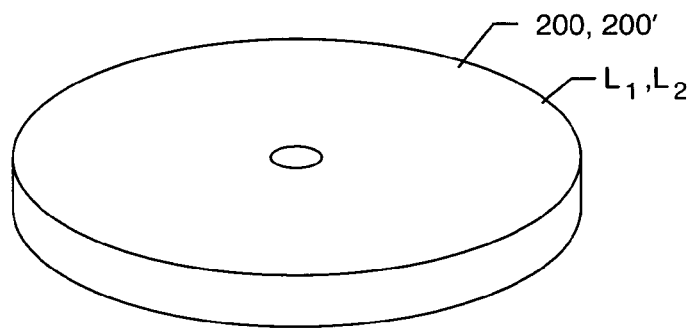
FIG. 34 is an isometric view of the lossy ferrite inductor of FIG. 33.

FIG. 34 is an isometric view of the lossy ferrite inductors 200, 200'.

Figure 35:
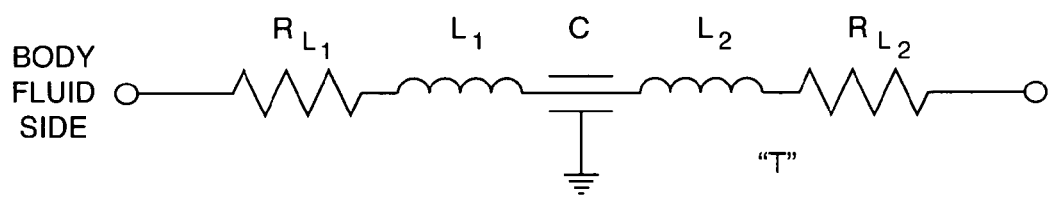
FIG. 35 is an electrical schematic diagram of the "T" circuit assembly of FIG. 33.

FIG. 35 is the schematic diagram of the T filter shown in FIG. 33.

Figure 36:
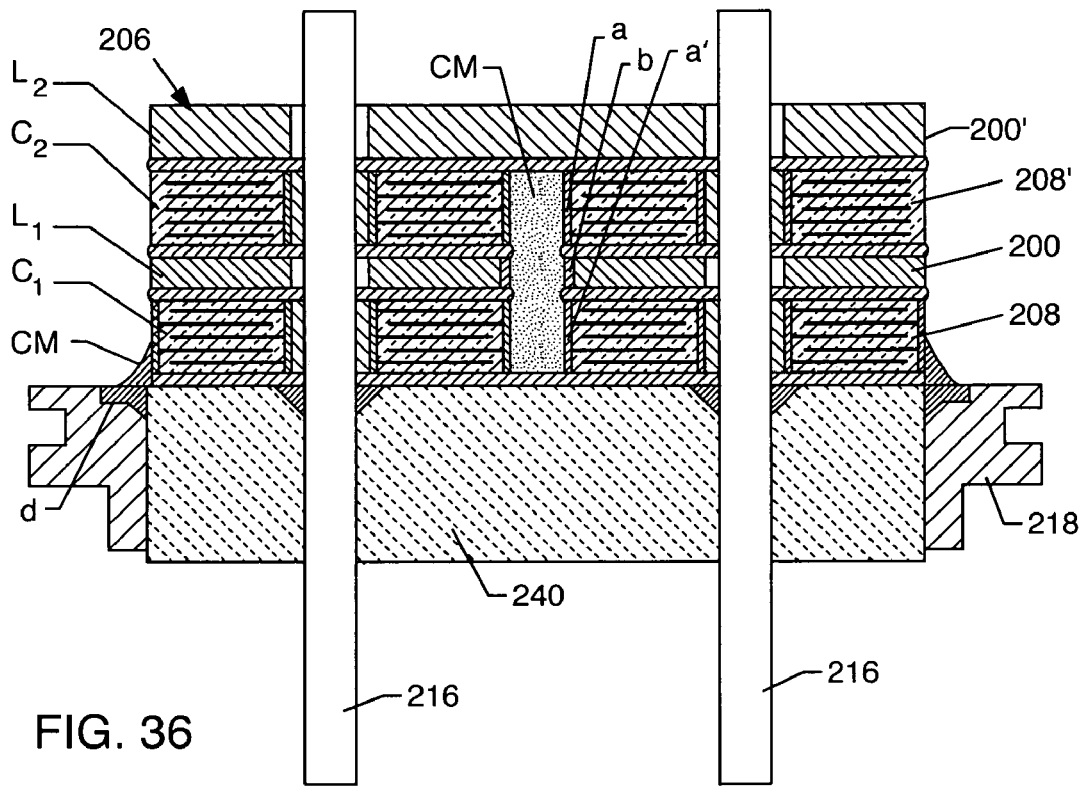
FIG. 36 is a sectional view similar to FIG. 24 illustrating a novel "double L" "$LL_2$" circuit configuration, wherein two inductors are stacked with two capacitors.

FIG. 36 illustrates a novel double L (LL) circuit configuration. In this case, the first capacitor 208 is oriented toward the body fluid side. There are two lossy ferrite inductors 200, 200' sandwiched between the two capacitors 208, 208' as shown. Inductor 200' is towards the pacemaker electronic circuits. The lower capacitor $C_1$ is a hybrid capacitor in that it has both an external and internal ground. The internal ground communicates through a conductive via hole. This via hole can contain a ground pin or be filled with a conductive material such as a thermal setting conductive adhesive, a solder or the like. The important thing is that the ground hole of the novel hybrid capacitor $C_1$ communicates with the ground plates of the upper capacitor $C_2$. It is in this way that the ground electrodes of capacitor $C_2$ are connected to a RNF ground point. In the case where the via hole is filled with a conductive medium CM, it is preferable to have additional insulation on the inside diameter of the inductor slab $L_1$ as shown. This is shown as material b and can be of the group of any insulating material including non-conductive polymers, non-conductive epoxies, insulating sleeves, insulating tubing and the like. The upper and lower feedthrough capacitors both have internal metallization a and a' in order to conduct their respect ground electrode plates in parallel. The conductive fill medium that connects the two capacitors together makes contact to this metallization a and a'. The outside diameter metallization of the lower feedthrough capacitor $C_1$ is connected with material M which in a preferred embodiment is a thermally conductive thermal setting material. M makes contact to the gold braze area d to provide a reliable oxide free electrical connection to the ferrule 218. The ferrule 218 is connected to the overall housing which is the electromagnetic shield of the implantable medical device (not shown). In this way the ground electrode plates of both the lower and upper capacitors $C_1$ and $C_2$ become a part of the continuous overall electromagnetic shield of the active implantable medical device. Referring once again to the via hole fill material CM, this could also be a solid pin such as a copper pin or a nickel pin wherein this would be soldered or installed by using a thermal setting conductive adhesive to make contact with the capacitor respective ground electrode plate termination a and a'. The LL configuration is particularly effective in that it has a very high attenuation slope rate (see FIG. 21). However, it would be preferred in an MRI application to have the inductance point towards the body fluid side. The reason for this is that capacitor 208 tends to lower the input impedance of the cardiac pacemaker. This causes a corresponding increase in MRI currents in the cardiac leadwires. Accordingly, it would be preferable to have lossy ferrite inductor 200 swapped in place of capacitor 208 so that higher input impedance could be presented to the implanted leadwire system. Accordingly, FIG. 36 does not represent the best preferred embodiment.

Figure 37:
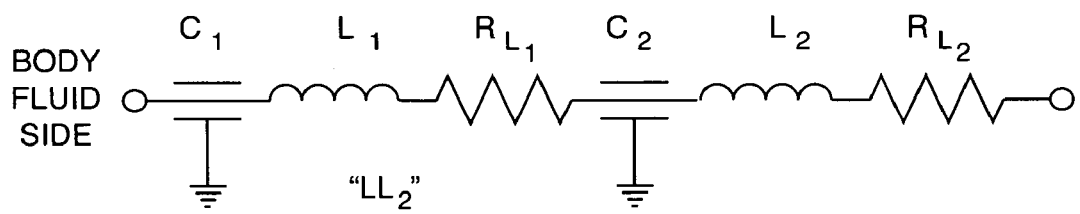
FIG. 37 is an electrical schematic diagram of the "$LL_2$" circuit assembly of FIG. 36.
Figure 38:
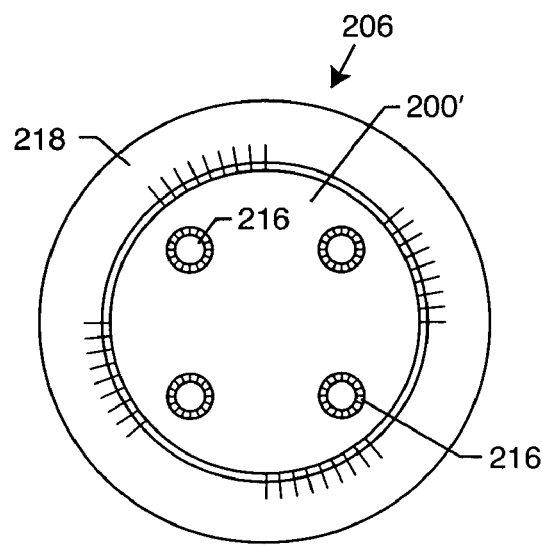
FIG. 38 is a top plan view of the assembly of FIG. 36.

FIG. 37 is a schematic diagram of the LL EMI filter assembly 206 shown in FIG. 36. FIG. 38 is one possible top view of the LL section quadpolar feedthrough capacitor described in FIG. 36. It will obvious to those skilled in the art that other configurations (square, rectangular, etc.) and lesser or more leadwires are possible.

Figure 39:
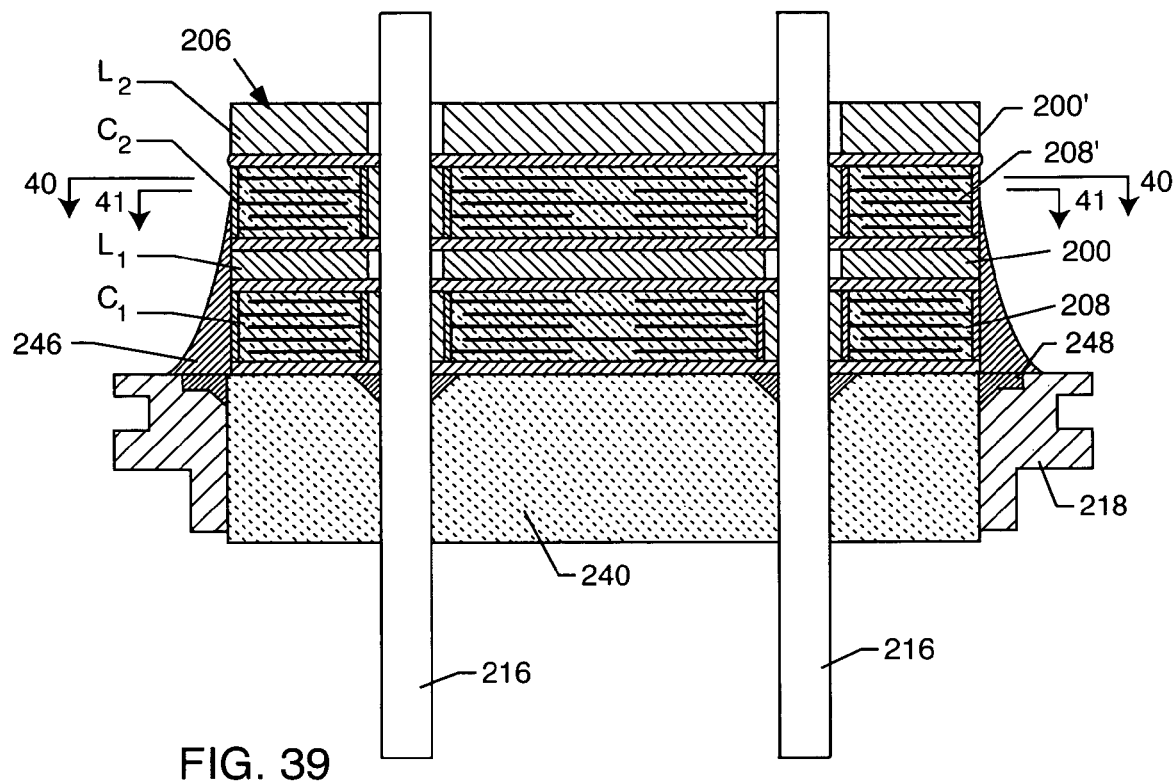
FIG. 39 is a sectional view similar to FIG. 36, illustrating another form of the "$LL_2$" circuit configuration wherein both capacitors are externally grounded.

FIG. 39 illustrates another form of the LL capacitor previously described in FIG. 36. The previously described LL capacitor in FIG. 36 has a combination of a hybrid capacitor incorporating both an external and internal ground 208 and a conventional internally grounded capacitor 208'.

Referring to the LL filter of FIG. 39, one will see the capacitors 208 and 208' are conventional feedthrough capacitors with an external metallized ground connection. The capacitor ground connections are made by the conductive thermal setting material 246 as shown. In the preferred embodiment 246 would be a silver filled conductive polyimide or the equivalent. As one can see the silver fill makes contact to gold braze 248 and is run up across the insulated ferrite slab 200 so that it also makes contact with the outside diameter metallization of feedthrough capacitor 208'. It will be obvious to those skilled in the art that other materials could be used for the conductive material 246 including solder, brazes, conductive epoxies and the like.

Figures 40, 41:
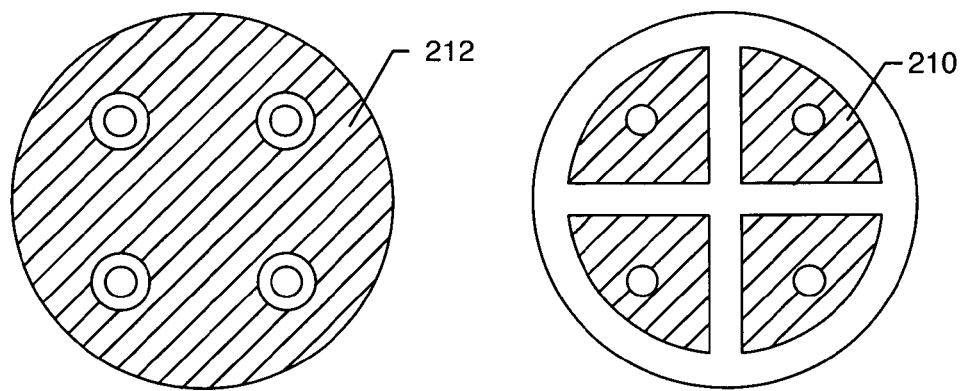
FIG. 40 is a sectional view taken generally along the line 40-40 of FIG. 39, illustrating a configuration of ground electrode plates in the upper capacitor.
FIG. 41 is a sectional view taken generally along the line 41-41 of FIG. 39, illustrating the configuration of active electrode plates in the upper capacitor.

FIG. 40 is a sectional view through the capacitor 208' illustrating the configuration of the ground electrode plates.

FIG. 41 is a sectional view taken generally along the line 41-41 of FIG. 39, illustrating the configuration of the active electrode plates within the capacitor 208'.

Figure 42:
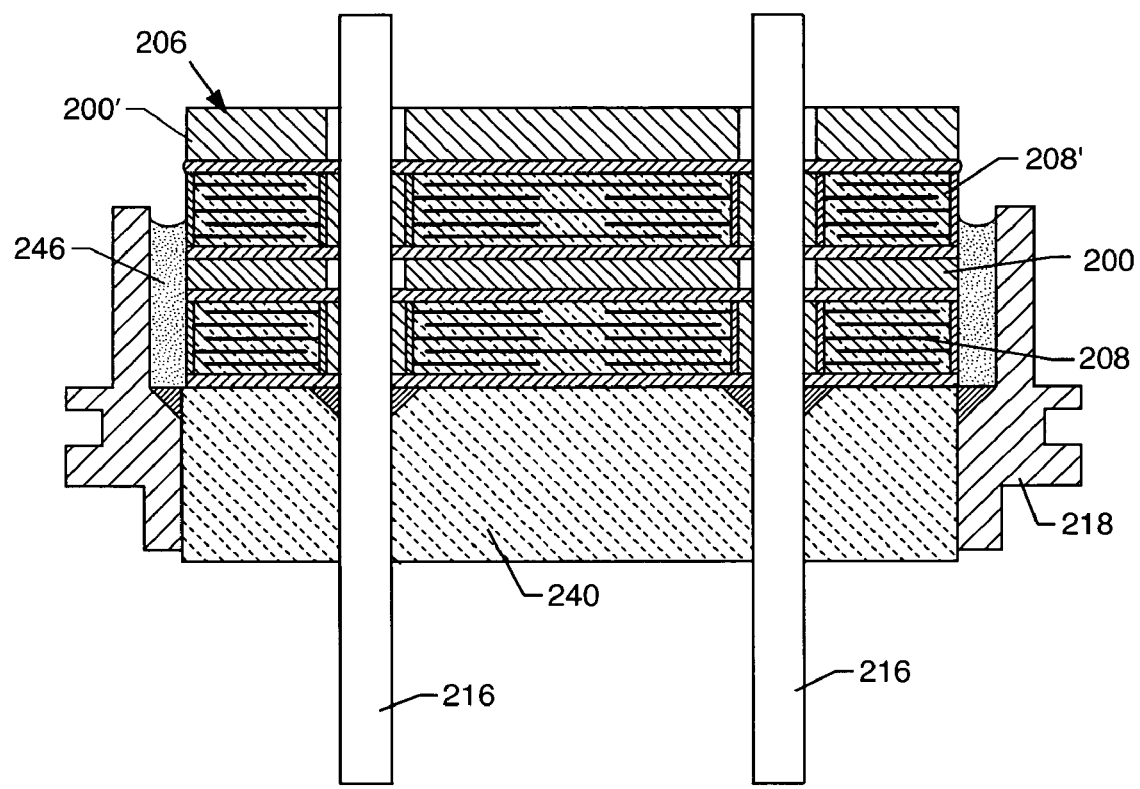
FIG. 42 is a sectional view similar to FIGS. 36 and 39, illustrating yet another embodiment of a "$LL_2$" circuit configuration wherein the ferrule of the hermetic terminal has been extended upwardly.

FIG. 42 illustrates yet another embodiment of a LL capacitor previously described in FIG. 36. In this case, the ferrule 218 of the hermetic terminal has been extended upward so as to provide an annular space that surrounds the feedthrough capacitors 208 and 208'. The conductive material 246 as previously described in FIG. 39 is placed to make an electrical contact to both of the capacitor outside diameter ground termination areas.

FIGS. 43, 44, 45 and 46 describe the hybrid feedthrough capacitor 208 previously described in FIG. 36. FIG. 43 is an isometric drawing of feedthrough capacitor 208. FIG. 44 is the cross-section of said capacitor 208. FIG. 45 represents the active electrode plates and FIG. 46 represents the ground electrode plates.

FIG. 47 is an isometric drawing of the sintered lossy ferrite inductors 200 and 200' that are shown in cross-section FIG. 36. FIG. 48 illustrates that said slab inductors have been conformally coated with insulative material 244. In a preferred embodiment, material 244 would be Paralene D. Paralene D is a vapor deposited high temperature tempered conformal coating material. It can withstand high temperature laser welding operations typical in cardiac pacemaker assembly. It can also withstand high voltage as is typical in ICD applications. Paralene D also has excellent wear and scratch resistance properties which makes it easy to handle during manufacturing.

FIG. 49 is an isometric drawing of the upper feedthrough capacitor 208' of the LL filter previously described in FIG. 36.

FIG. 50 is the cross-section of the upper quadpolar capacitor 208' of FIG. 49. This is an internally grounded feedthrough capacitor previously described in U.S. Pat. No. 5,905,627. FIGS. 51 and 52 illustrate the active and ground electrode plates 210, 212 of the internally grounded feedthrough capacitor shown in FIG. 49.

Figure 53:
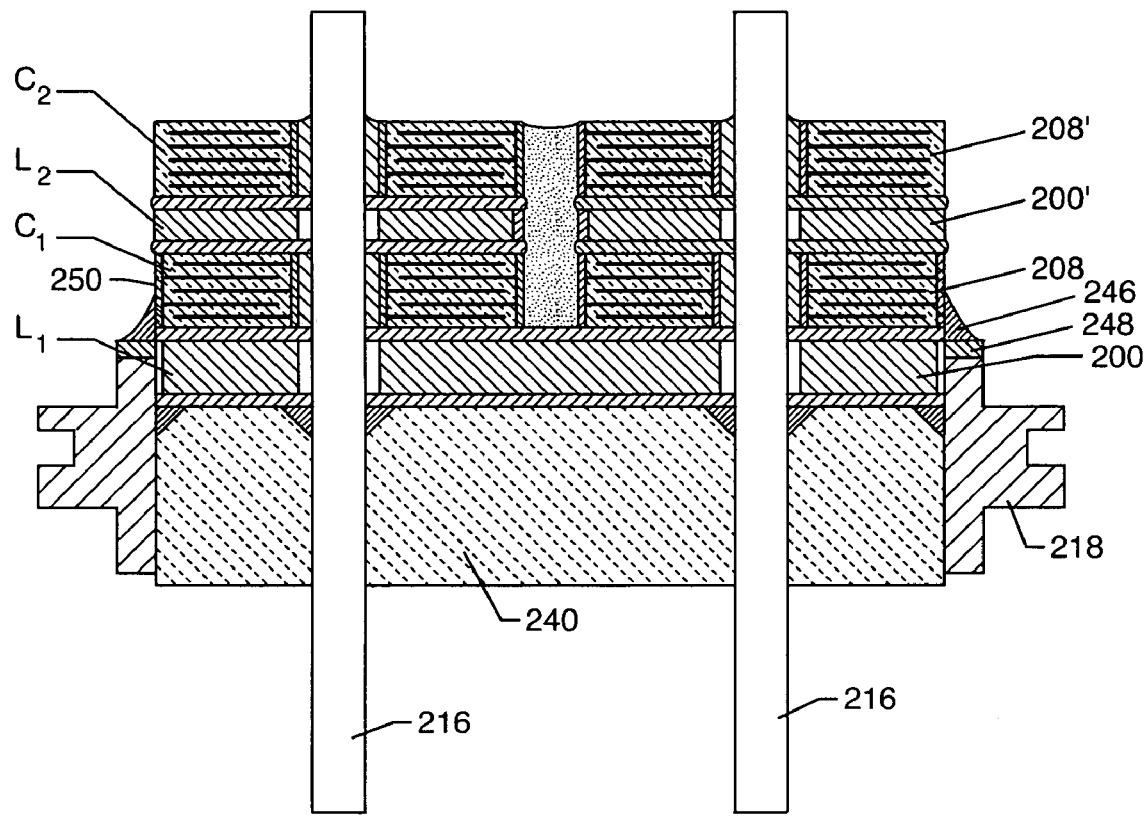
FIG. 53 is a sectional view similar to FIG. 36, illustrating an "$LL_1$" EMI filter wherein the first lossy ferrite inductor is oriented toward the body fluid side.

FIG. 53 illustrates the preferred embodiment of a LL EMI filter in that the lossy ferrite inductor 200 is now oriented toward the body fluid side. As one can see, the previously described hybrid capacitor 208 is attached to an elevated ferrule 218 flange with conductive bonding material 246. An additional gold sputter or braze or equivalent material 248 has been added to the top of the ferrule flange 218 so that a reliable oxide free electrical connection can be formed from the outside diameter metallization 250 (ground metallization) of feedthrough capacitor 208 to the ferrule 218 (see U.S. Pat. Nos. 6,765,779 and 6,765,780).

Figure 54:
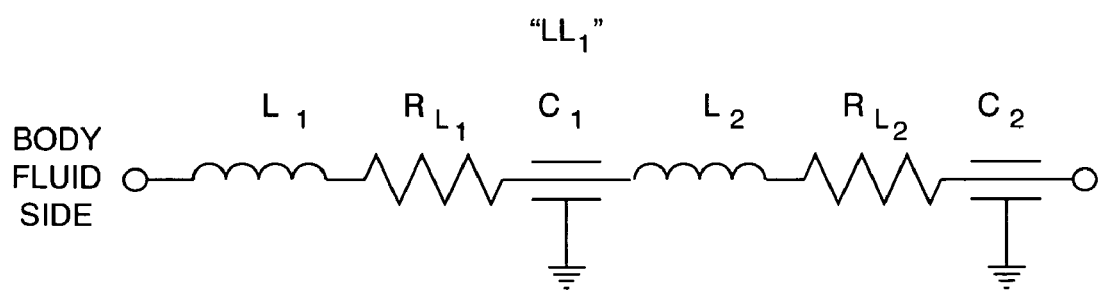
FIG. 54 is an electrical schematic diagram of the EMI filter illustrated in FIG. 53.

FIG. 54 is the schematic diagram of the LL EMI filter described in FIG. 53. As one can see, it is desirable to have lossy ferrite inductor $L_1$ (200) oriented towards the body fluid side. This has the effect of raising the implanted leadwire impedance and electrically isolating the feedthrough capacitors 208 and 208'. Also oriented toward the body fluid side is resistor $R_{L1}$. This is the high frequency lossy or ohmic electric characteristic of the novel lossy ferrite inductor 200. By orienting $L_1$ and $R_{L1}$ both towards the body fluid side, this serves to raise the impedance of the leadwire system. As previously mentioned, this is highly desirable to reduce the amount of MRI current flowing in the leadwire system. Less current means less heating and less tendency to cause venous or TIP/RING ablation (tissue damage). Such overheating has been noted in the reference literature and is highly undesirable.

Figure 55:
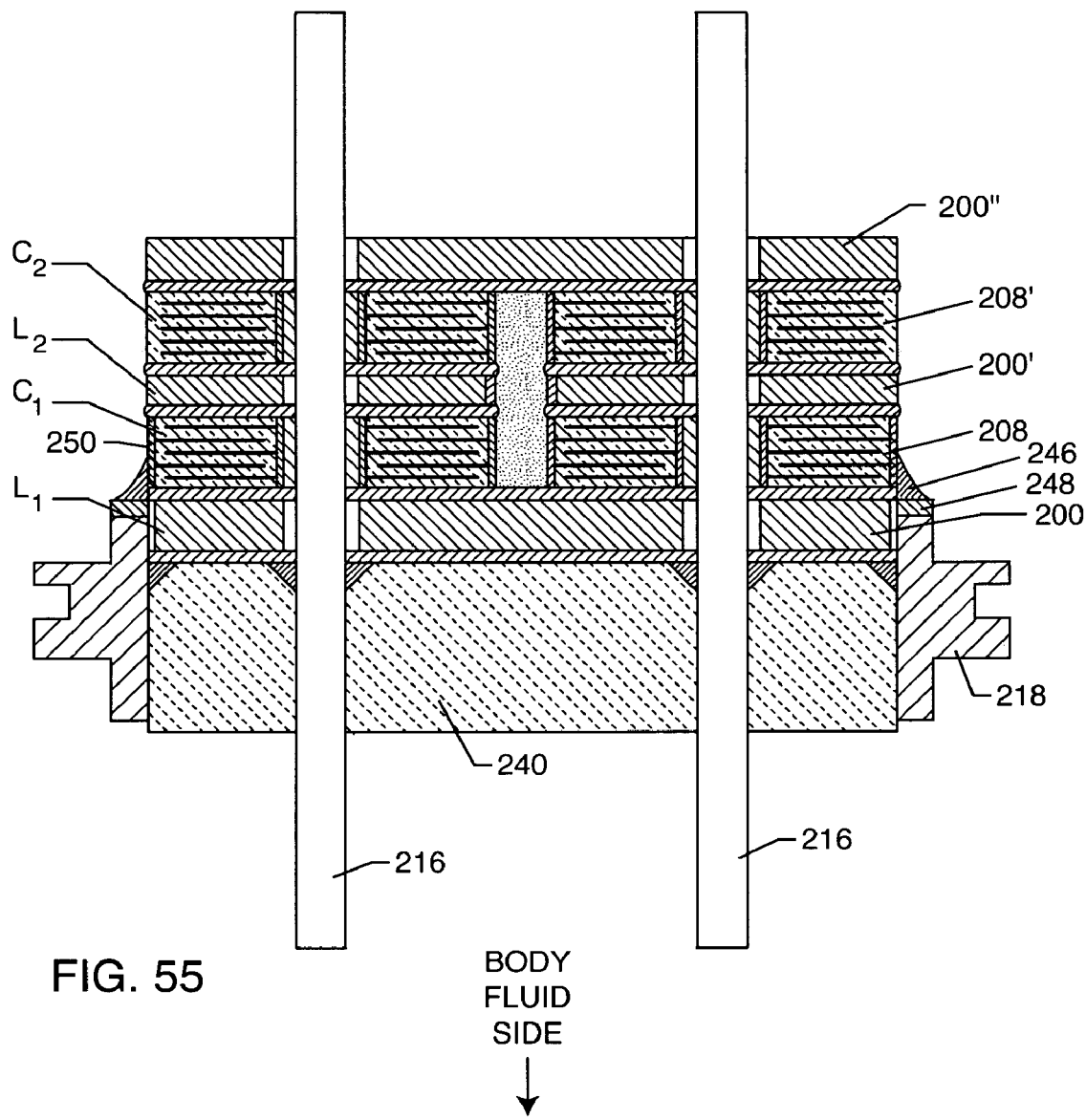
FIG. 55 is a sectional view similar to FIG. 53 wherein an additional inductive element has been added.

FIG. 55 is very similar to FIG. 53 except that an additional inductive element 200" has been added. This makes the feedthrough filter assembly into what is known as a five element filter.

Figure 56:
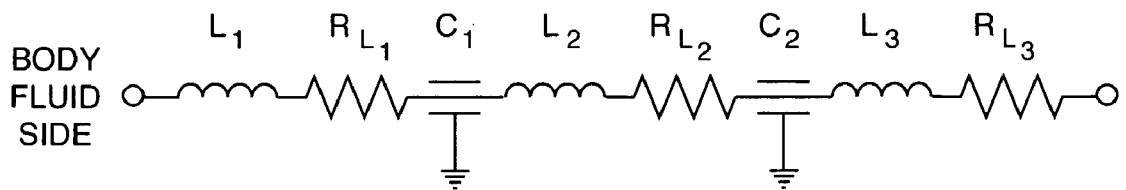
FIG. 56 is an electrical schematic diagram of the "5-Element" EMI filter illustrated in FIG. 55.

FIG. 56 is the schematic diagram of the five element filter. As illustrated in FIG. 21, the five element filter has a very high attenuation slope rate. As one increases the number of pulls n of the low pass filter network attenuation slope continues to increase. That is, 6, 7, 8 or even more elements would be desirable. Each time one leaves the lossy conductor slab with a corresponding capacitor, one adds additional pulls to the low pass filter circuit. However, due to the space limitations of an implantable medical device, it is not likely that five element filters will be used. In actual practice, the preferred embodiment is practically limited to a LL which is also known as a four element low pass filter.

Figure 57:
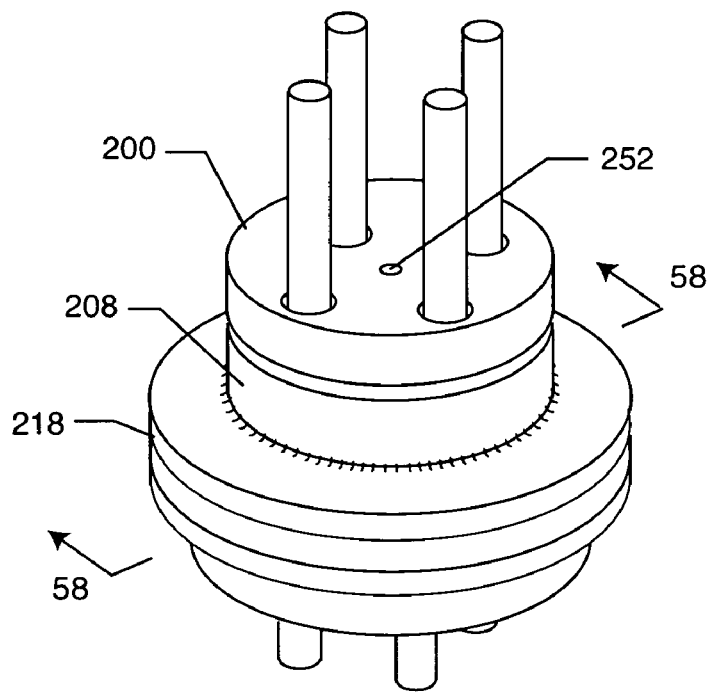
FIG. 57 is a perspective view of an "$L_1$" quadpolar inductor feedthrough terminal assembly having a lossy ferrite inductor co-bonded to the capacitor which incorporates a leak detection vent.
Figure 58:
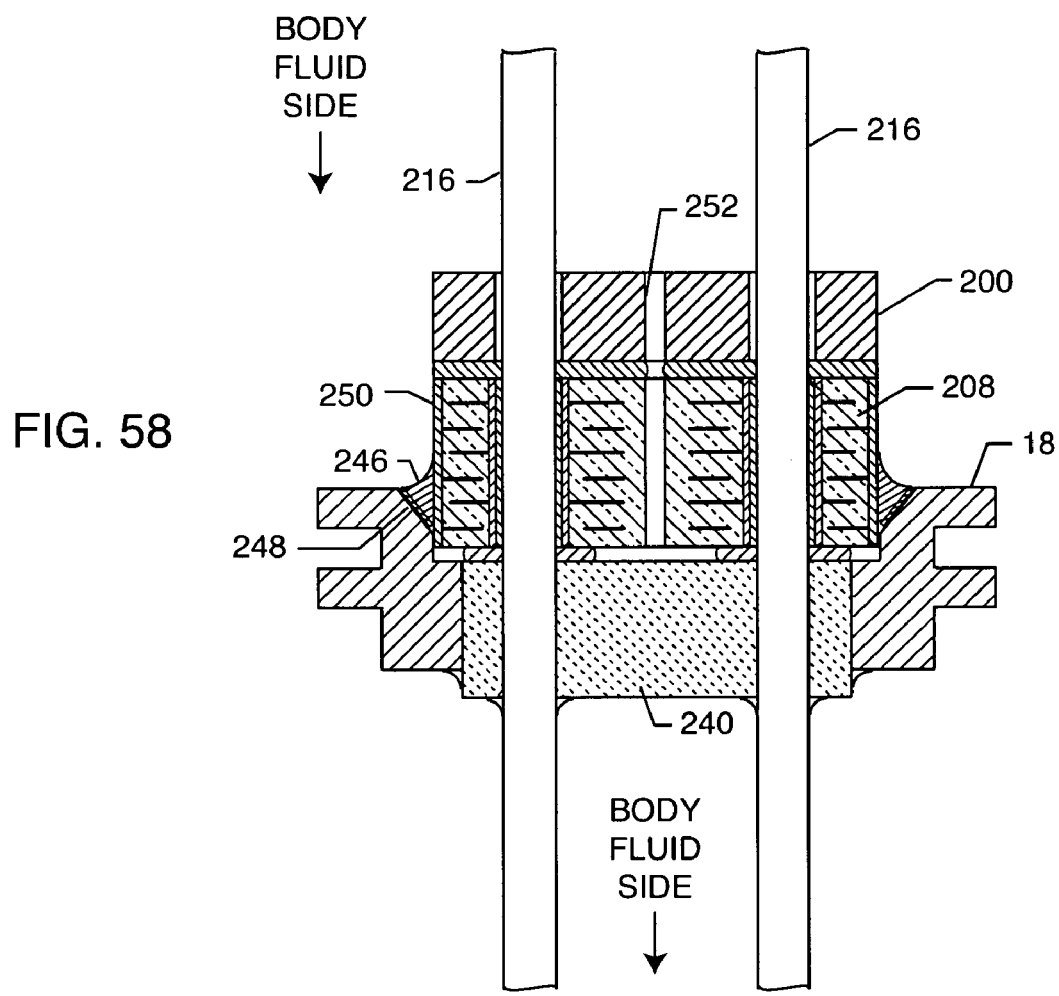
FIG. 58 is a sectional view taken along the line 58-58 of FIG. 57.

FIG. 57 illustrates a quadpolar lossy ferrite inductor 200 shown co-bonded to a quadpolar feedthrough capacitor 208. This is better shown in the cross-sectional view of FIG. 58. One can see that there is a leak detection vent 252 in accordance with U.S. Pat. No. 6,566,978 shown through the device into passage or air space. This facilitates ready passage of helium gas during a hermetic seal test.

FIG. 59 illustrates an inline quadpolar lossy ferrite inductor 200 with multiple turns of insulated leadwire 216. This is shown co-bonded to a inline quadpolar feedthrough capacitor 208. Adding multiple turns is very efficient since the inductance increases as the square of the turns. Accordingly, the lossy ferrite inductor 200 will have 4 times the inductance as if only one turn passed through it as shown in previous drawings. In accordance with the present invention, the lossy ferrite inductor 200 raises the input impedance of the device and also which helps to protect it from MRI. In addition, since the four leadwires 216 are placed in different areas of the heart, substantial magnetic flux density cancellation can occur. This helps to avoid saturation of the lossy ferrite inductor allowing it to properly operate in the presence of high fields.

FIG. 60 is the schematic diagram of the LC filter of FIG. 59.

FIG. 61 illustrates an improved inline lossy ferrite inductor 200 which facilitates passing multiple turns. This was previously described in pending U.S. patent application Ser. No. 10/825,900.

Figure 62:
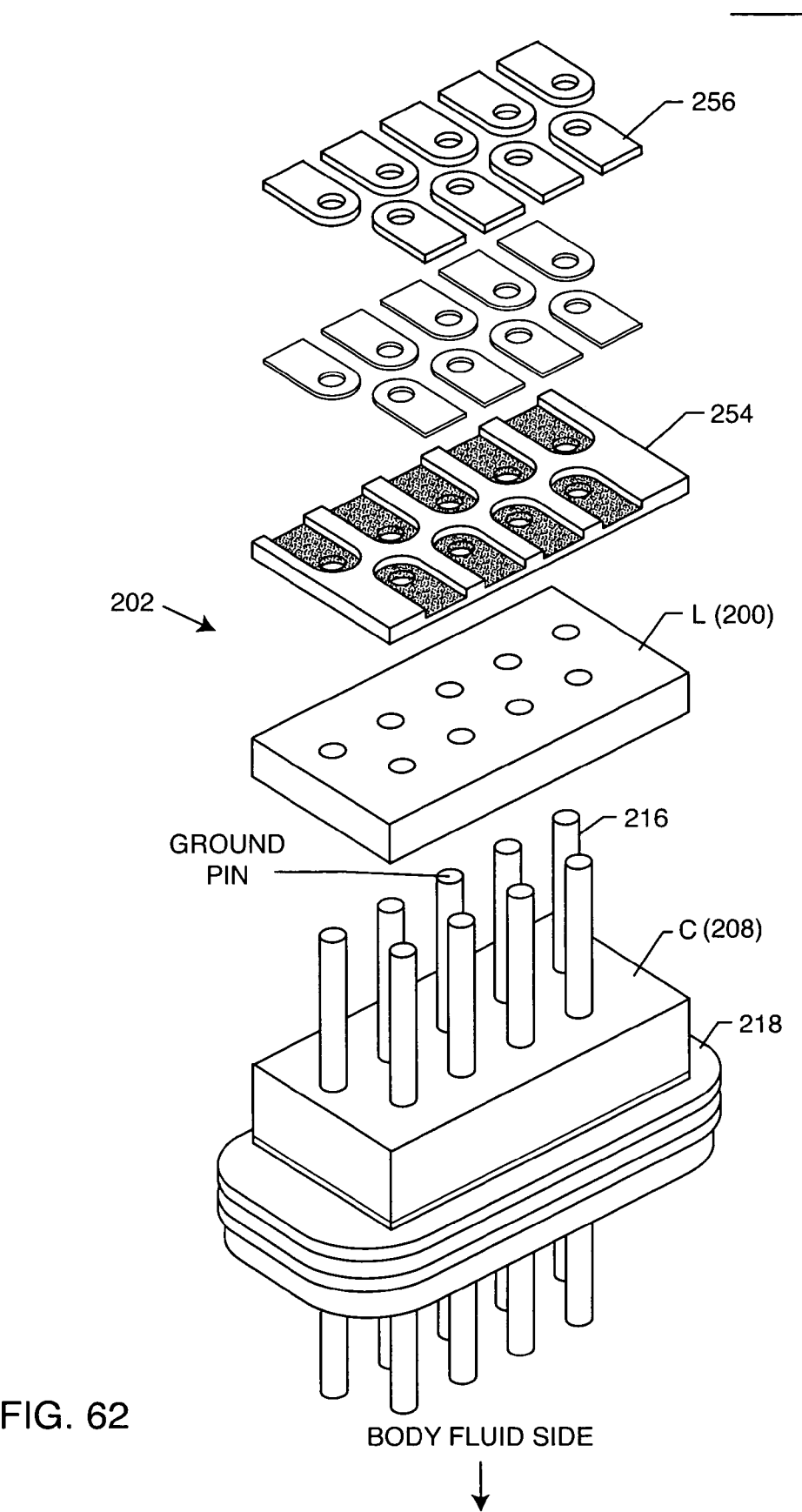
FIG. 62 is an exploded perspective view of a dual inline hermetic terminal with bonded feedthrough capacitor, and with a co-bonded "$L_1$" circuit lossy ferrite inductor.

FIG. 62 illustrates a dual inline hermetic terminal 202 with bonded feedthrough capacitor C (208). There are eight active pins 216 and one ground pin as illustrated. Accordingly, feedthrough capacitor C (208) is an internally grounded capacitor with its ground electrode plates connected to the grounded pin. Lossy ferrite inductor L (200) is shown ready for co-bonding to the ceramic capacitor C (208). By placing all of the leadwires 216 through the common lossy ferrite inductor L (200) substantial magnetic flux density cancellation due to out of phase signals is achieved. A novel alumina substrate 254 with wire bond pads 256 is also shown ready for co-bonding. This is also previously described in pending U.S. patent application Ser. No. 10/825,900.

Figure 63:
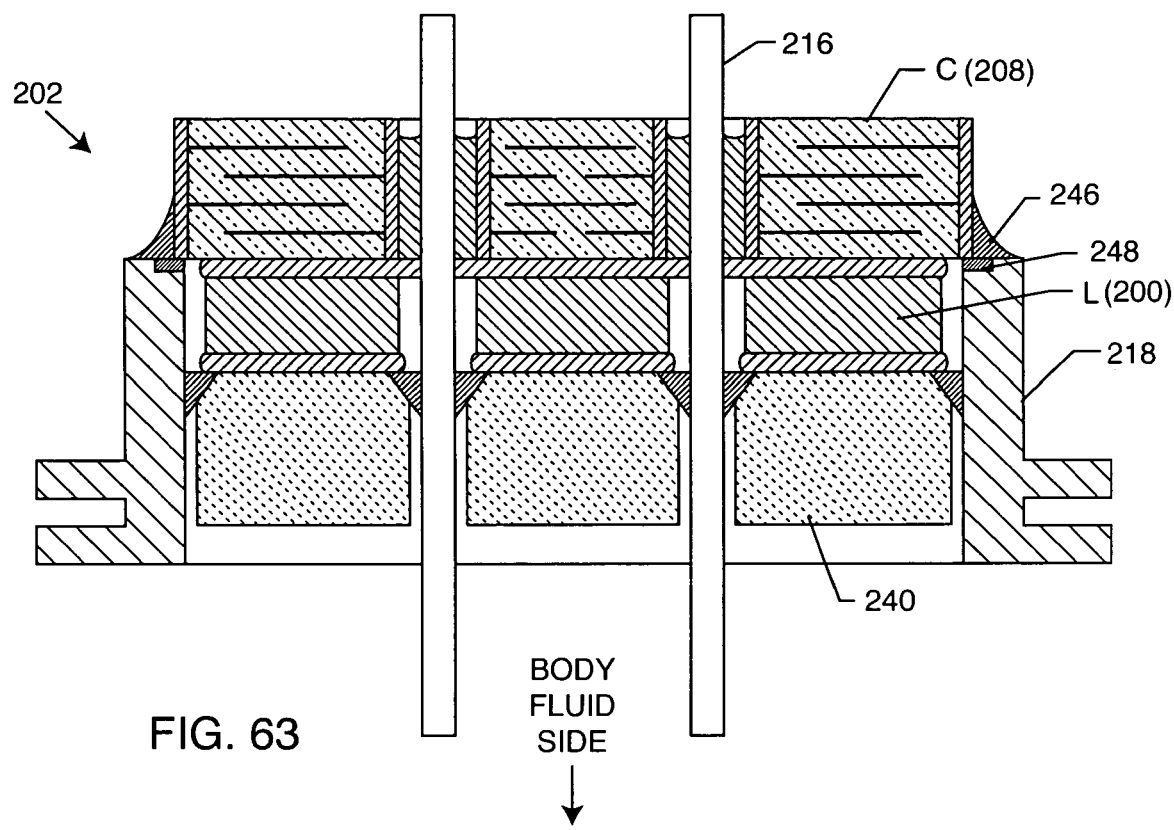
FIG. 63 is a sectional view of an "$L_2$" filtered terminal wherein the lossy ferrite inductor is positioned toward the body fluid side of the device.
Figure 64:
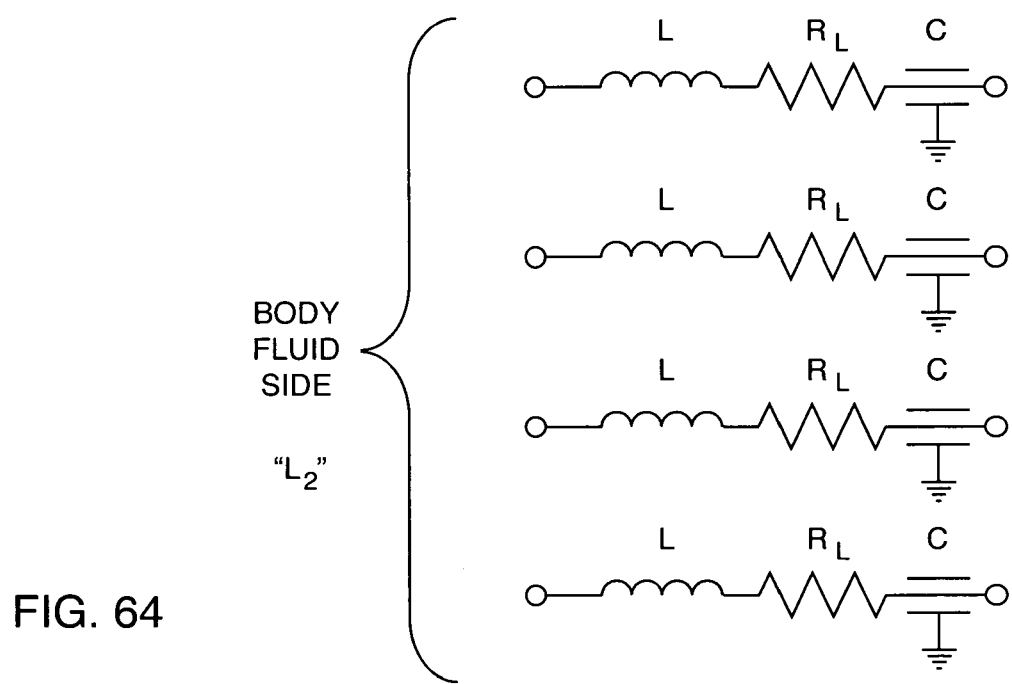
FIG. 64 is a sectional view of the terminal of FIG. 63.

FIG. 63 illustrates yet another improved embodiment wherein the lossy ferrite inductor L (200) is positioned toward the body fluid side of the device. Accordingly, the feedthrough capacitor C (208) is pointed towards the implantable electronics of the implantable medical device. This is a quadpolar L-section filter device as illustrated in the schematic diagram of FIG. 64. The top view could be rectangular, square or round as previously shown. This is a highly desirable or preferred embodiment in that the lossy ferrite inductor 200 acts to increase the impedance of the leadwire system. By positioning capacitor 208 on the other side of the lossy ferrite inductor 200, its relatively low impedance is then positioned to protect the internal electronics, but not unduly lower the impedance of the leadwire system itself.

Referring now back to FIG. 63, one can see that there is a conductive polyimide material 246 which is attached to a gold braze area 248 of the titanium ferrule 218 of the hermetic terminal 202.

Figure 65:
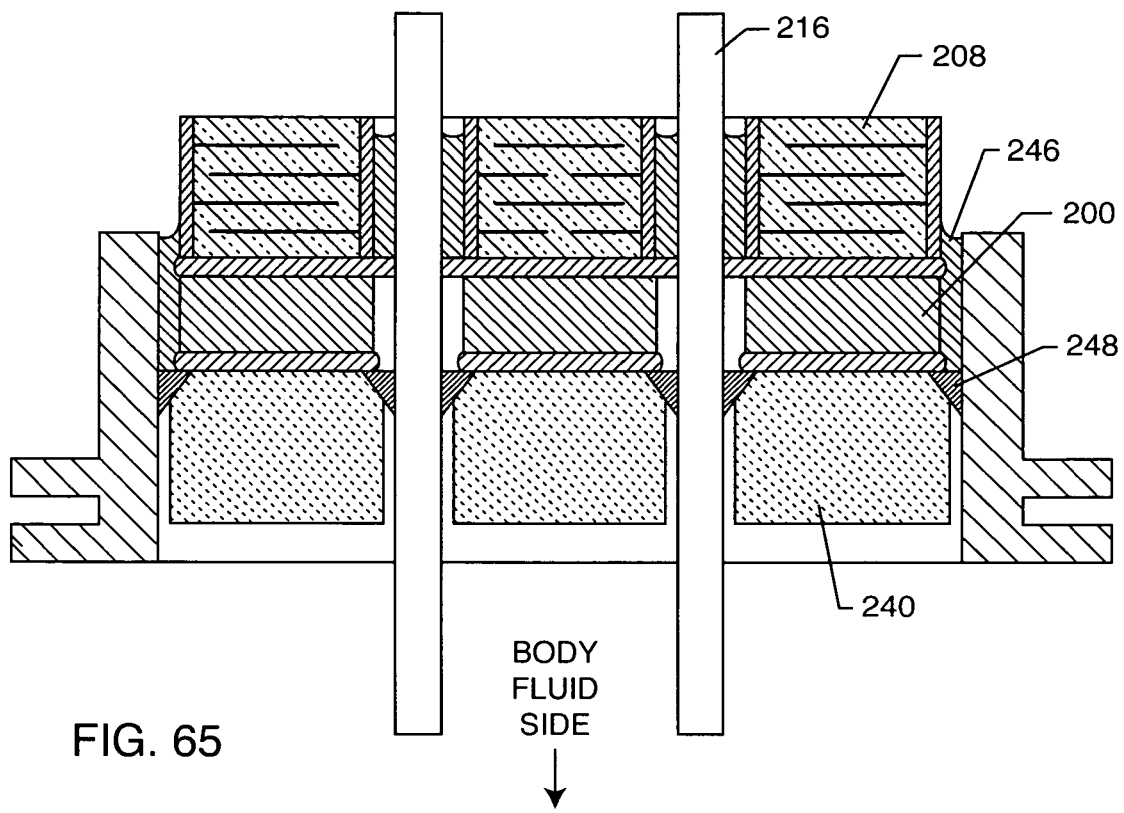
FIG. 65 is a sectional view similar to FIG. 63, wherein attachment material 246 is shown connected to the capacitor outside diameter to the inside diameter of the ferrule 218.

FIG. 65 is very similar to FIG. 63 except that the attachment material 246 is shown connected between the outside diameter of the capacitor 208 and the inside diameter of the ferrule 218. Attachment material 248 desirably contacts gold braze material 248 in accordance with U.S. Pat. No. 6,765,779.

Figure 66:
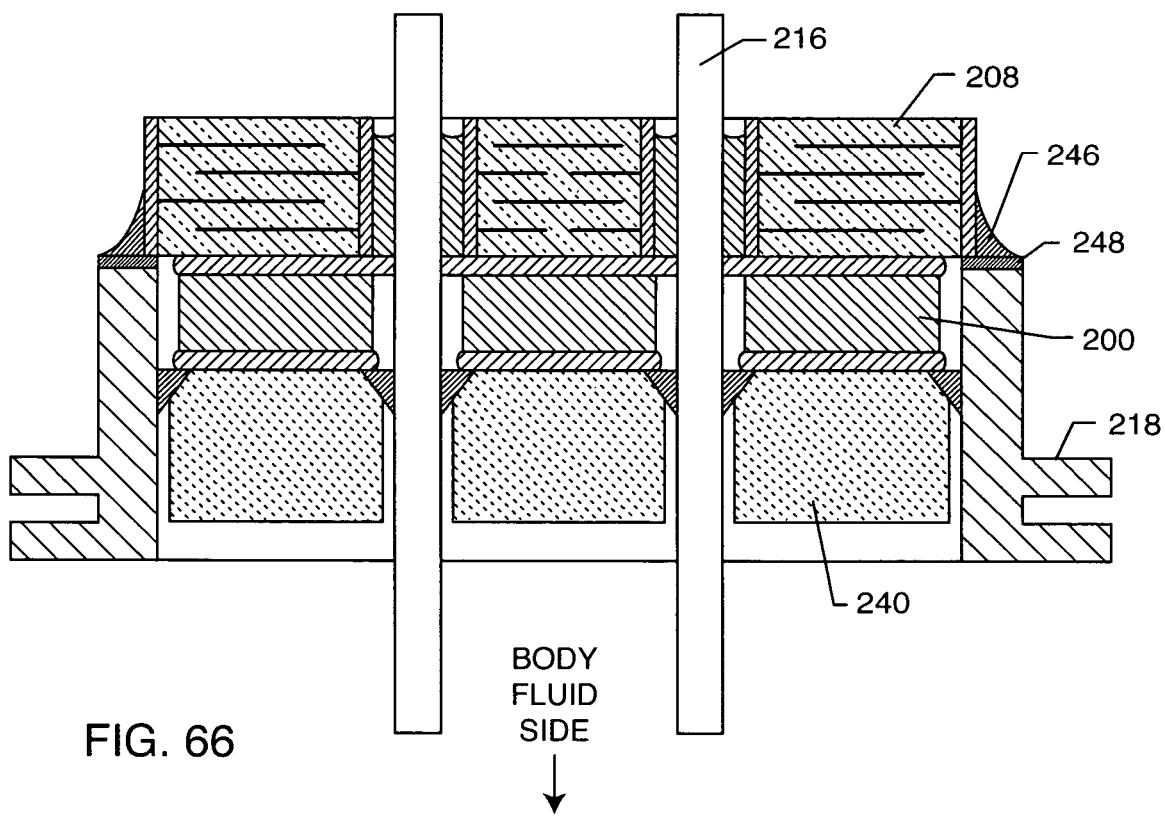
FIG. 66 is a sectional view similar to FIGS. 63 and 65, except that the conductive polyimide material 246 is connected to a gold braze 248.

FIG. 66 is also very similar except that the conductive polyimide material 246 is shown connected to a gold braze 248 which goes across the entire top of a flange portion of the ferrule 218.

Figure 67:
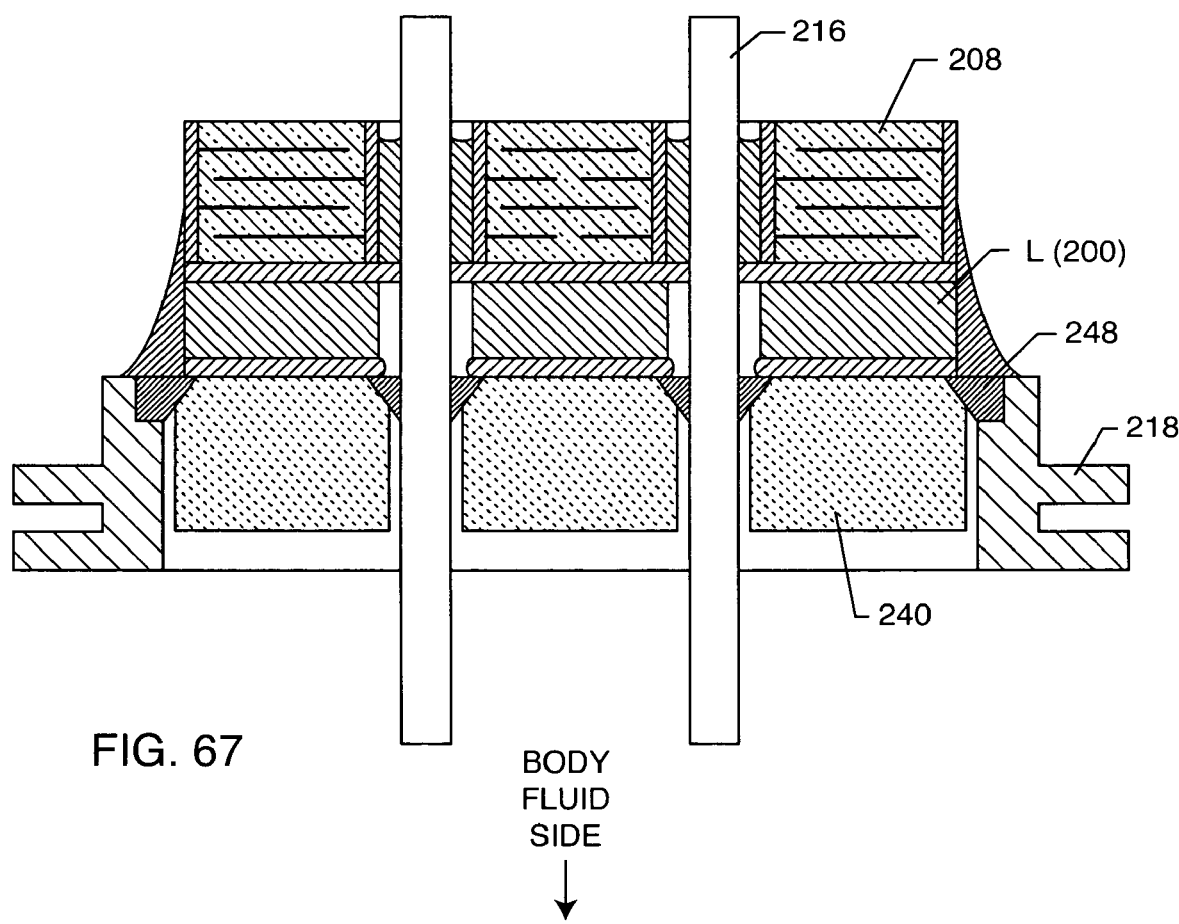
FIG. 67 is a sectional view similar to FIG. 63, except that the electrical connection material makes contact from the gold braze area non-conductively across the inductor slab to the outside diameter metallization of the feedthrough capacitor.

FIG. 67 is very similar to FIG. 63 except that the electrical connection material 246 makes contact from the gold braze area 248 of the hermetic terminal flange 218 across in a non-conductive relationship with the inductor 200 to the outside diameter metallization of the feedthrough capacitor 208.

Figure 68:
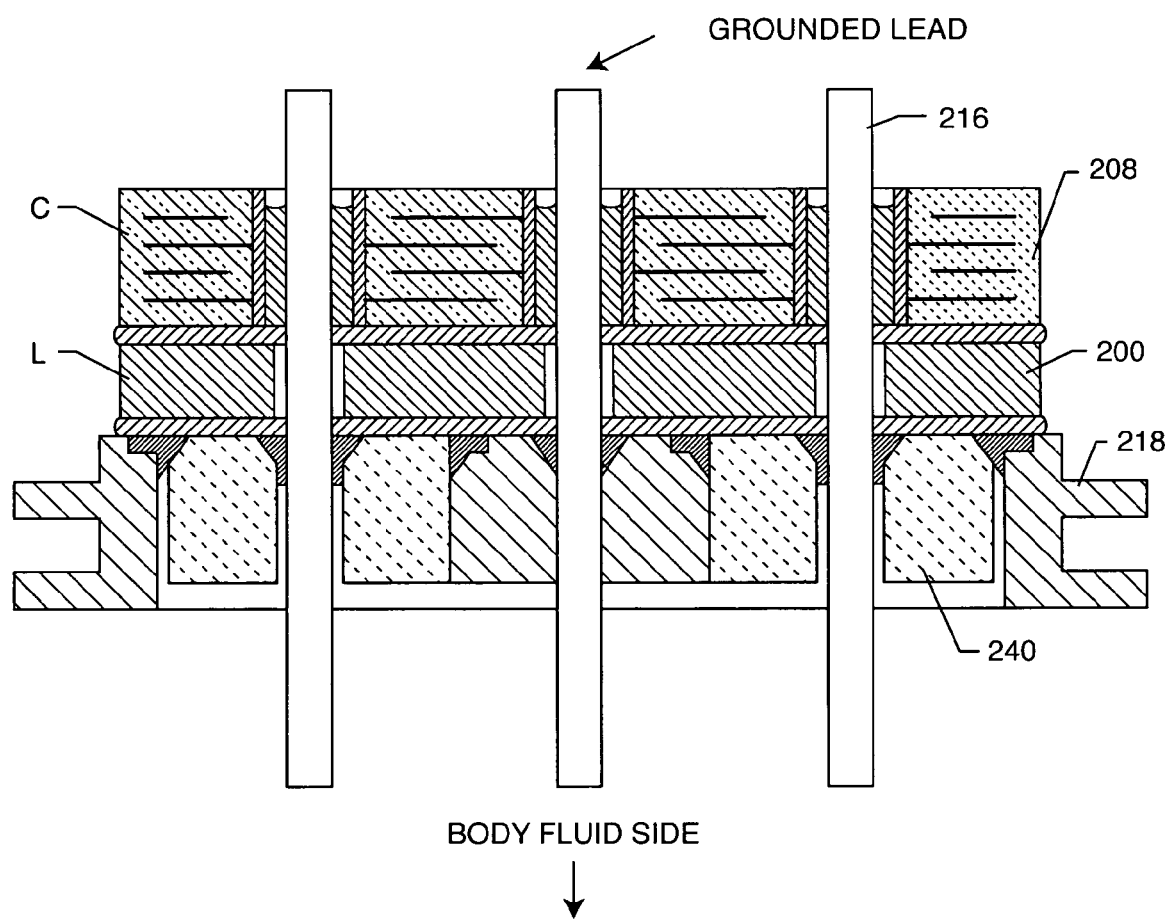
FIG. 68 is a sectional view similar to FIGS. 63, 65 and 66, of an internally grounded capacitor hermetic terminal including a surface mounted lossy ferrite inductor 200.

FIG. 68 is a cross-sectional view of an internally grounded capacitor 208 of the present invention showing the lossy ferrite inductor 200 oriented towards the body fluid side.

Figure 69:
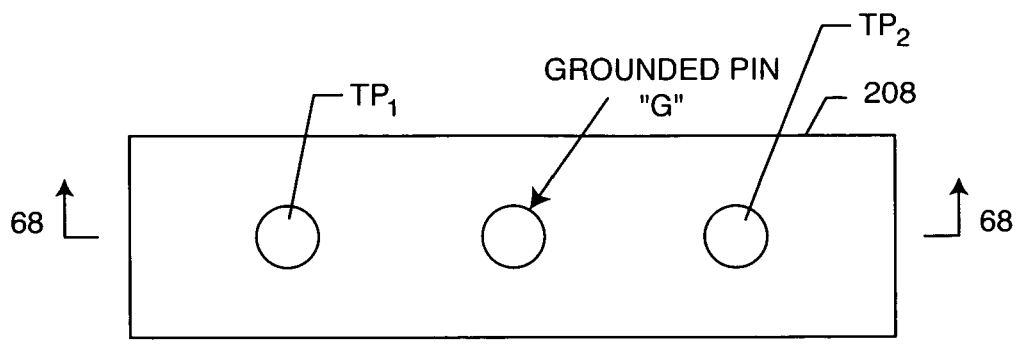
FIG. 69 is one possible top view corresponding to the structure of FIG. 68.
Figure 70:
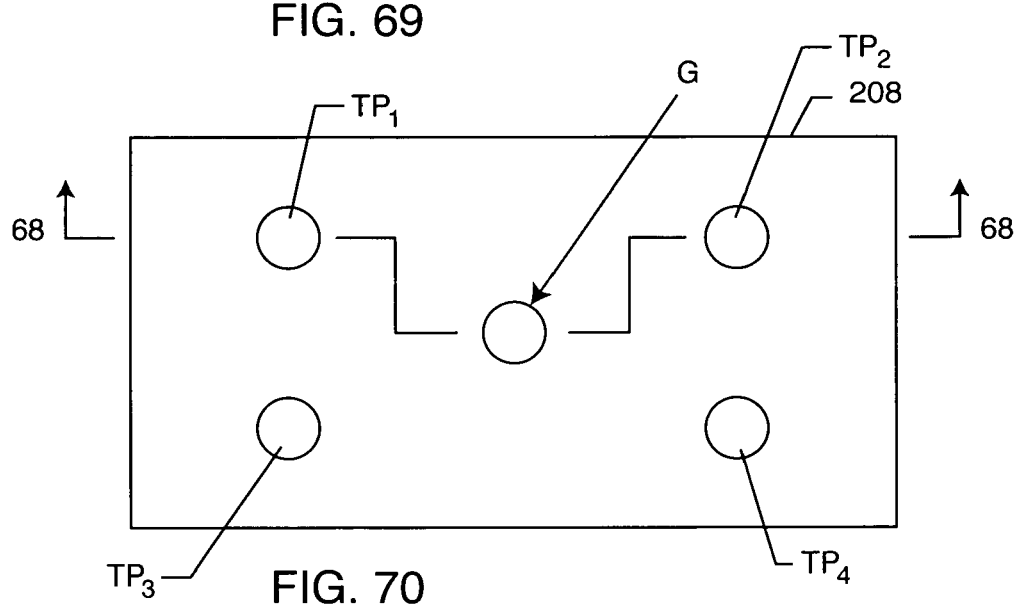
FIG. 70 is a first alternative top plan view corresponding to the structure shown in FIG. 68.
Figure 71:
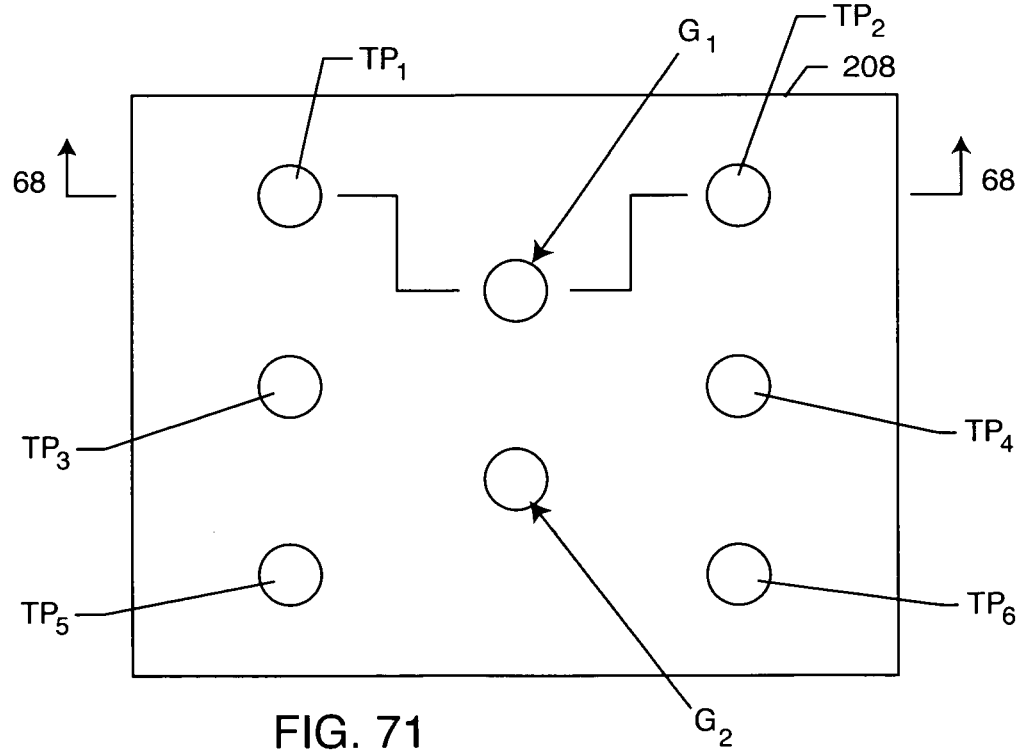
FIG. 71 is a second alternative top plan view of a structure corresponding to the structure of FIG. 68.
Figure 72:
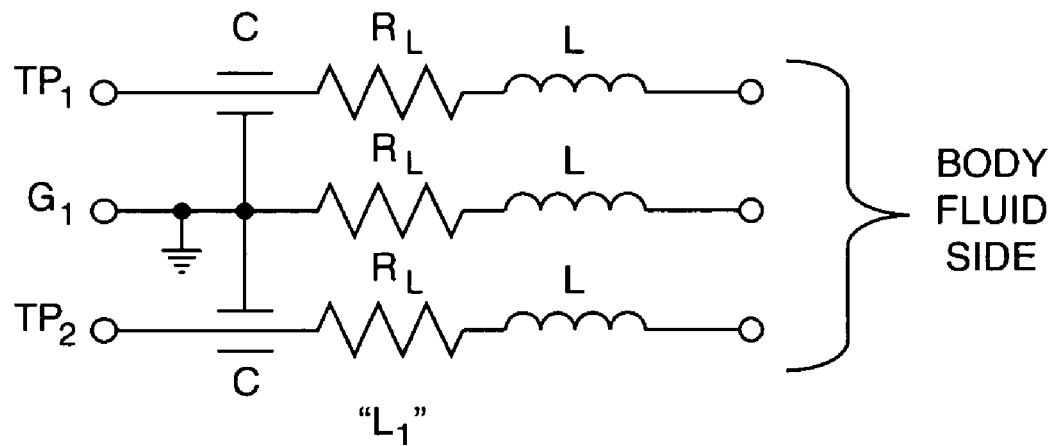
FIG. 72 is an electrical schematic diagram "$L_2$" corresponding to the structure of FIGS. 68 and 69.
Figure 73:
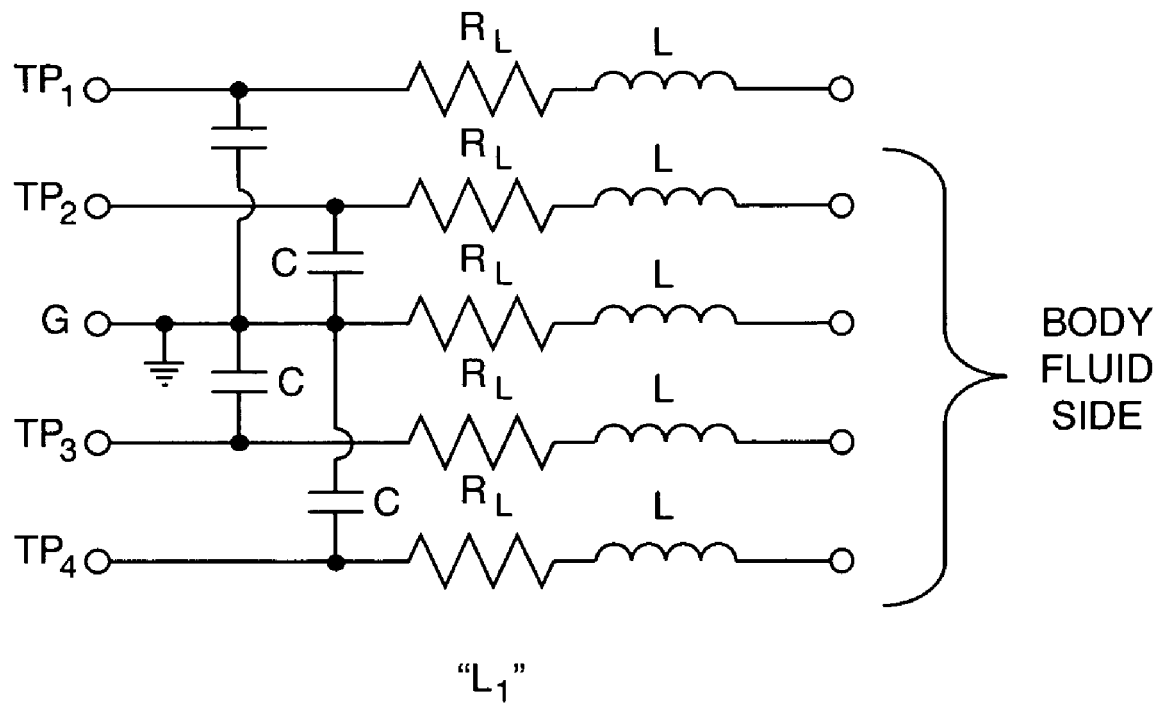
FIG. 73 is an electrical schematic diagram "$L_2$" corresponding to the structure of FIGS. 68 and 70.
Figure 74:
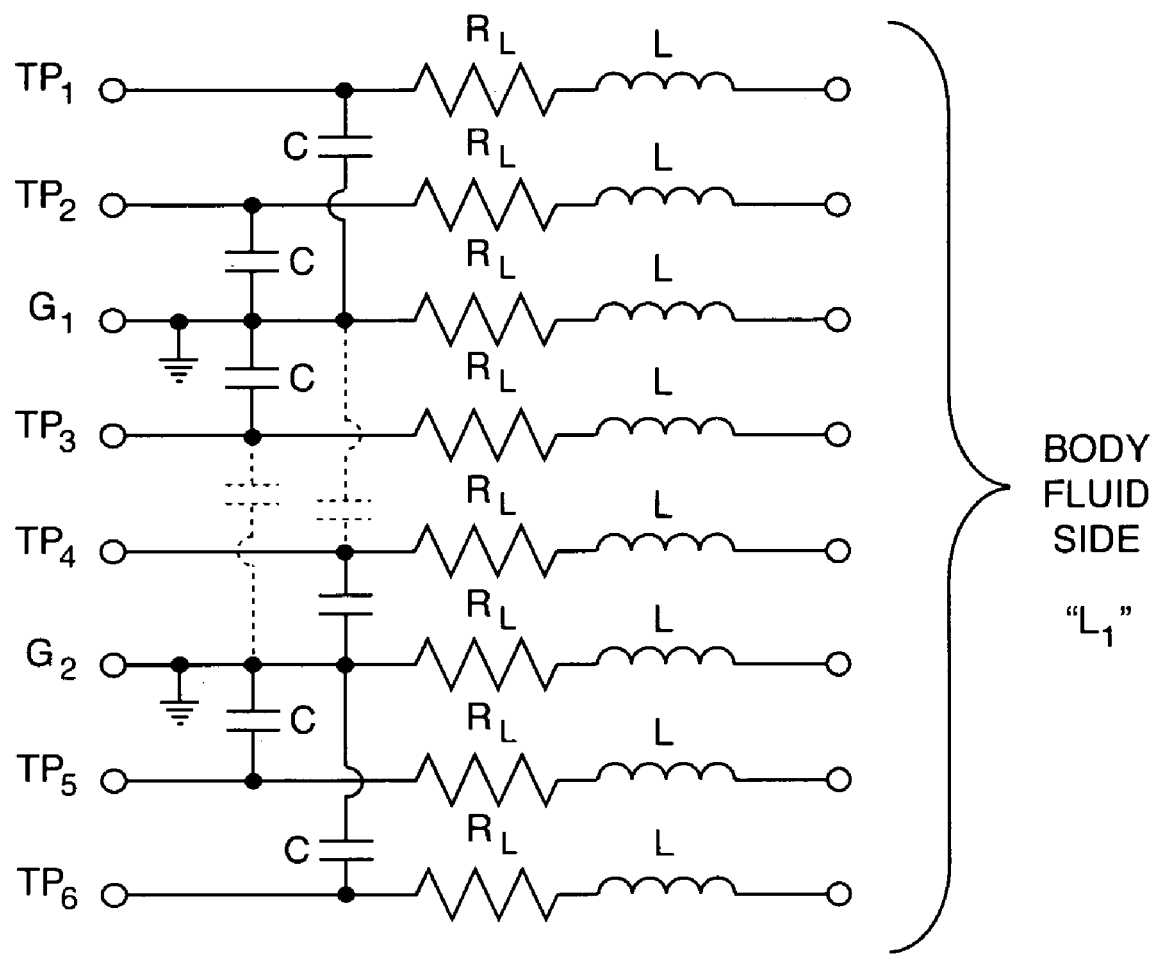
FIG. 74 is an electrical schematic diagram "$L_2$" corresponding to the structure of FIGS. 68 and 71.

FIGS. 69, 70 and 71 illustrate various possible top views that correspond with the internally grounded feedthrough capacitor 208 of FIG. 68. Accordingly, schematic diagrams 72, 73 and 74 illustrate various possible schematic diagrams that go with the internally grounded feedthrough capacitor 208 and lossy ferrite inductor 200 of FIG. 60.

Figure 75:
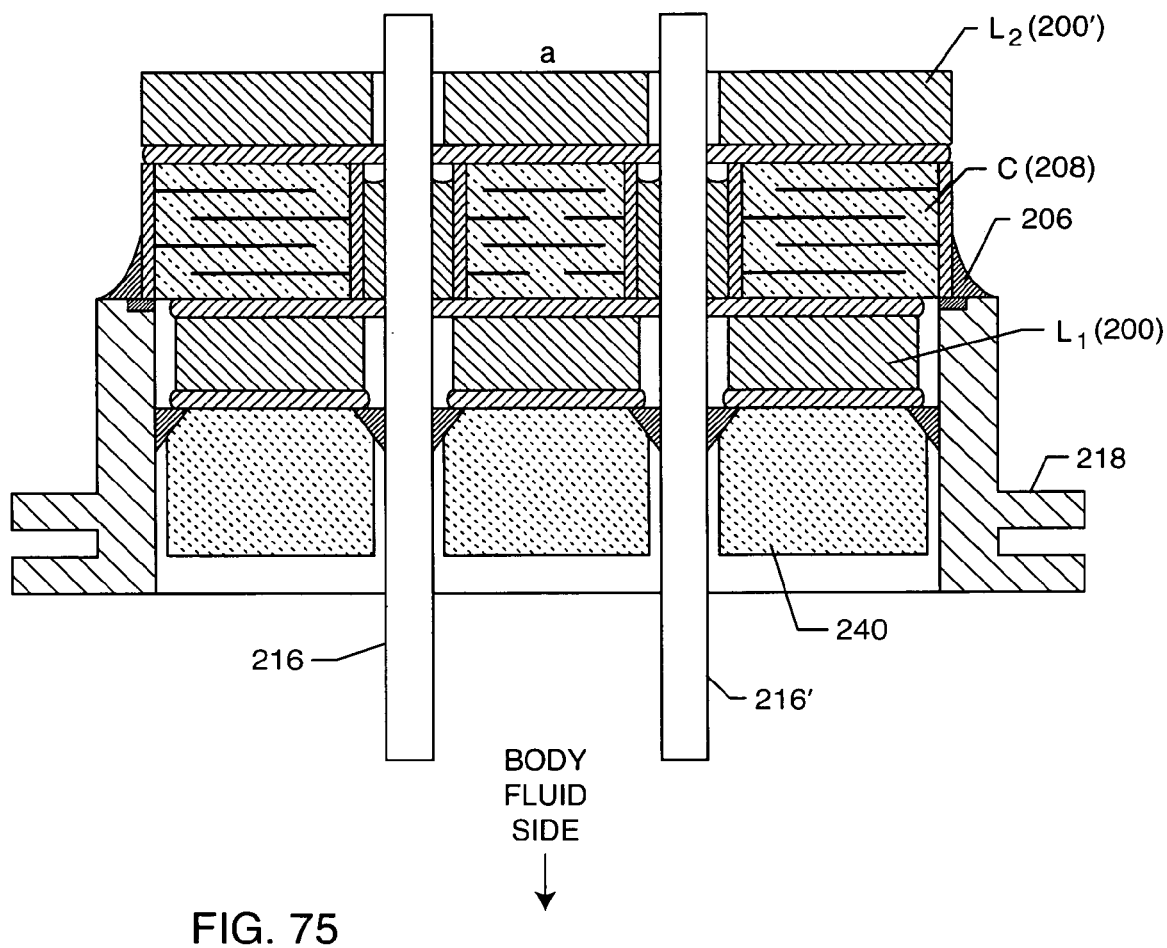
FIG. 75 is a sectional view similar to FIG. 65 illustrating a quadpolar "T" circuit filter configuration.

FIG. 75 is a cross-sectional drawing illustrating a "T" circuit filter configuration. A "T" circuit is also highly efficient in that lossy ferrite inductor $L_1$ (200) is oriented toward the body fluid side. Lossy ferrite inductor $L_2$ (200') points toward the electronics of the implantable medical device thereby tending to stabilize the device's input impedance. As previously shown in FIG. 21, the "T" is a very high performance EMI filter that will offer broad attenuation throughout the frequency range from 1 MHz to 100 MHz and above. As previously mentioned, EMI filters using only a capacitance C, generally are only effective from 100 MHz to about 3 GHz. The "T" section filter as shown in FIG. 75, has all the benefits of a feedthrough capacitor 208, but with the added benefits of inductances and high frequency dissipative losses placed on both sides of the feedthrough capacitor. The performance of the T filter is not quite as high as the performance of the LL circuit filter, however, it is outstanding compared to all prior art "C" circuit devices.

Figure 76:
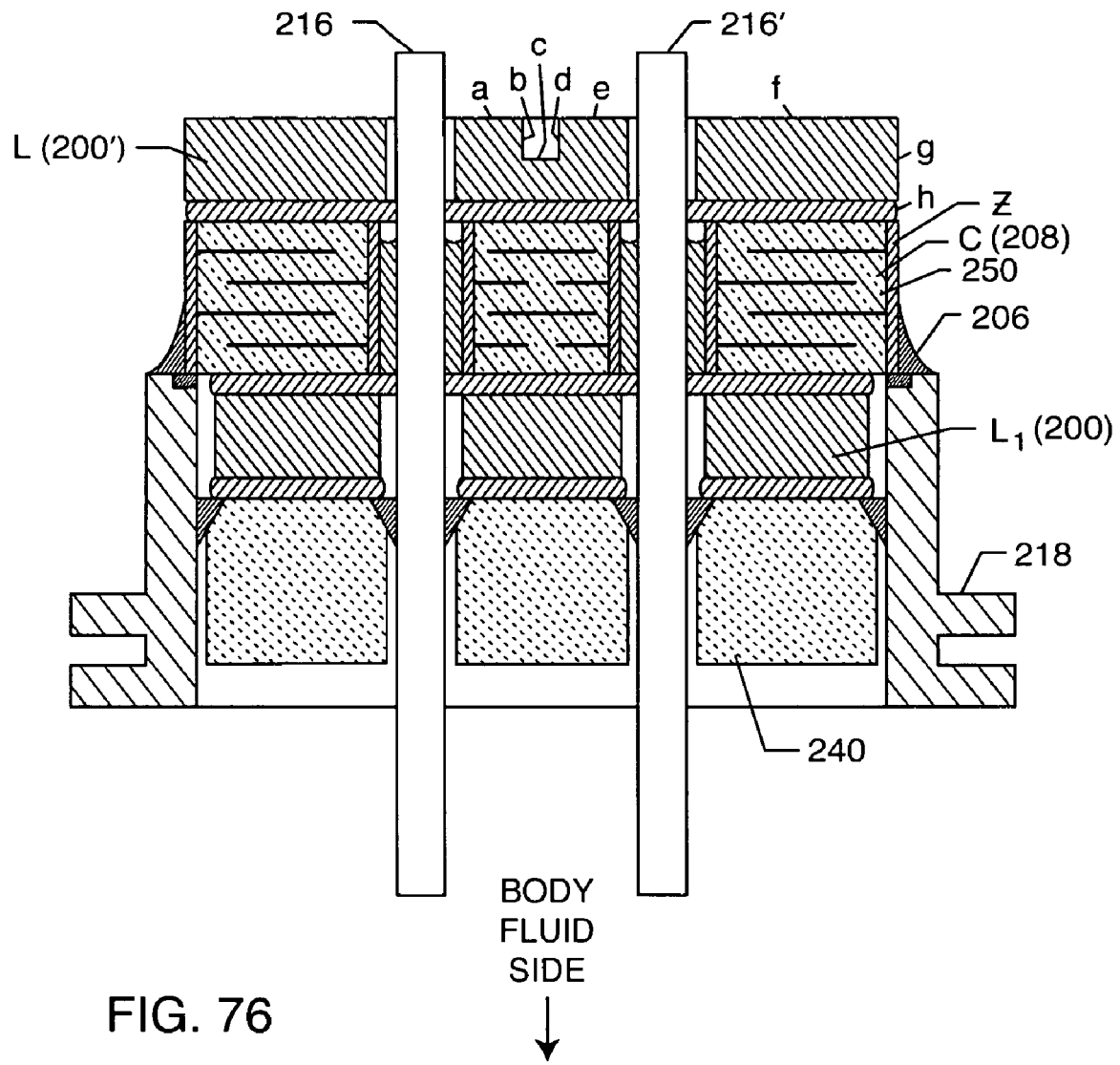
FIG. 76 is a sectional view similar to FIG. 75 which is smaller in diameter and wherein the lossy ferrite inductor includes a slot to create a tortuous path across the surface of the surface.
Figure 77:
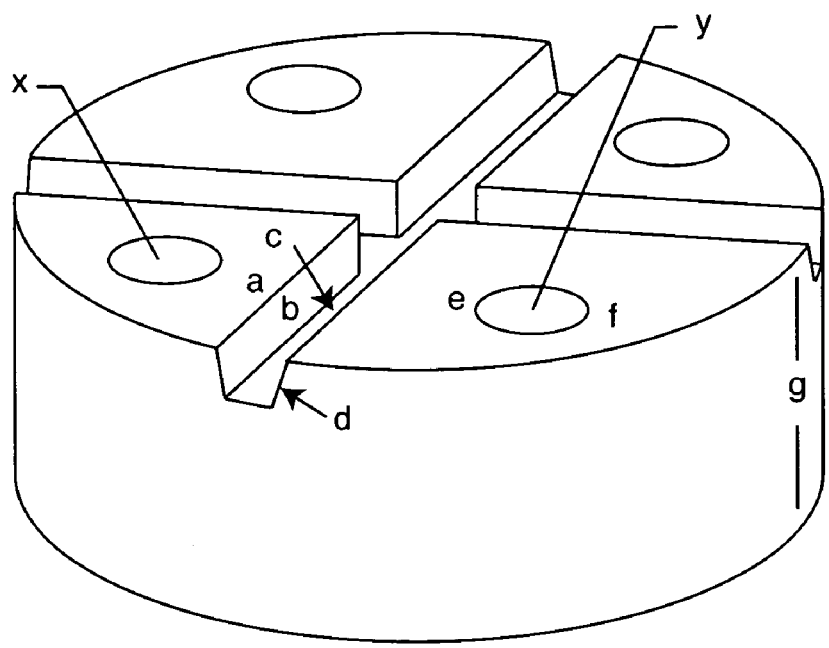
FIG. 77 is an enlarged top and side perspective view of the lossy ferrite inductor including the novel slot of FIG. 76.

FIG. 76 is very similar to the EMI filter assembly described in FIG. 75. One can see, however, that it is smaller in diameter. Referring back to FIG. 75, the relatively wide spacing between the two leadwires 216 and 216' is required in a high voltage implantable defibrillator application. This is because high voltage fields tend to arc across surfaces. In other words, it is very unlikely that a high voltage field would arc across the open air space as illustrated as letter a in FIG. 75. Referring once again to FIG. 76, one can see that a novel slot feature has been added to the novel lossy ferrite inductor 200' of the present invention. This greatly increases the surface path length between pins 216 and 216'. Starting from the right edge of pin 216, one can see that for an electric arc to follow the surface it would have to travel first along surface a then down along surface b across surface c, then up surface d, and across surface e to reach the point of opposite polarity on the left edge of pin 216'. In electrical engineering, this is called a tortuous path. In other words, the creepage distance from pin to pin has been significantly increased. This same feature can be added many of the ferrite slabs of the present invention including a ferrite slab on the body fluid side. For example, FIG. 33 illustrates a ferrite slab 200' that is shown on the body fluid side. This happens to be a unipolar device, but it will be obvious to one skilled in the art that if it were a multipin device that slots could be added to increase the creepage distance. This can be increasingly important to components exposed to body fluid in that tissue migration or even metal deposition can occur across such surfaces. The reason for this is that in a pacemaker there are electrical pulses present on the leads. There are also precious metal such as gold plating that could migrate or electroplate out in the presence of an electrolyte and voltage potential. Accordingly, an increased creepage path as illustrated in FIG. 76 is easily applicable to all body fluid embodiments illustrated in this patent. This is better illustrated by referring to the isometric view shown in FIG. 77. FIG. 77 is an isometric view of the upper inductor lossy slab 200' previously described in FIG. 76. This is a quad polar device with a crisscross slot providing the required tortuous path. One can follow surfaces a, b, c, d, and e which greatly increases the clearance between the pin location holes x and y.

Referring once again back to FIG. 76, there is another way that a surface flash or high voltage arc over can occur. Starting at the right side of pin 216' and tracing across surfaces f, g and h, one can see that if pin 216' was at a positive high voltage relative to the capacitor outside diameter termination z, then a voltage potential could occur across these surfaces. Referring to FIG. 76, the ferrule 218, which is designed to be welded to the titanium housing of a pacemaker or other implantable medical device, is at ground potential in this example. Electrical connection material 206 connects ferrule rule 218 to the capacitor outside diameter metallization 250. Accordingly, the outside diameter metallization 250 is at the same potential as the ferrule 218. In a preferred embodiment, a crosscut structure as shown in FIG. 77, would be preferred over a similar structure shown in FIG. 78. The reason for this is that the distance g (or height) is greater in FIG. 77 as compared with FIG. 78. This increases the voltage standoff or tortuous path tracing along surfaces f, g and h. In other words, by making g taller one increases the voltage standoff capability from either pin 216' or pin 216' to ground. Of course, in programmable implantable defibrillators, it is possible to have the can active. In other words, the ferrule 218 could be positive in reference to pin 216' which could then be negative and so on. However, in all cases it is desirable to have as much stand off distance as possible from pin to pin and from pin to ground.

Figure 78:
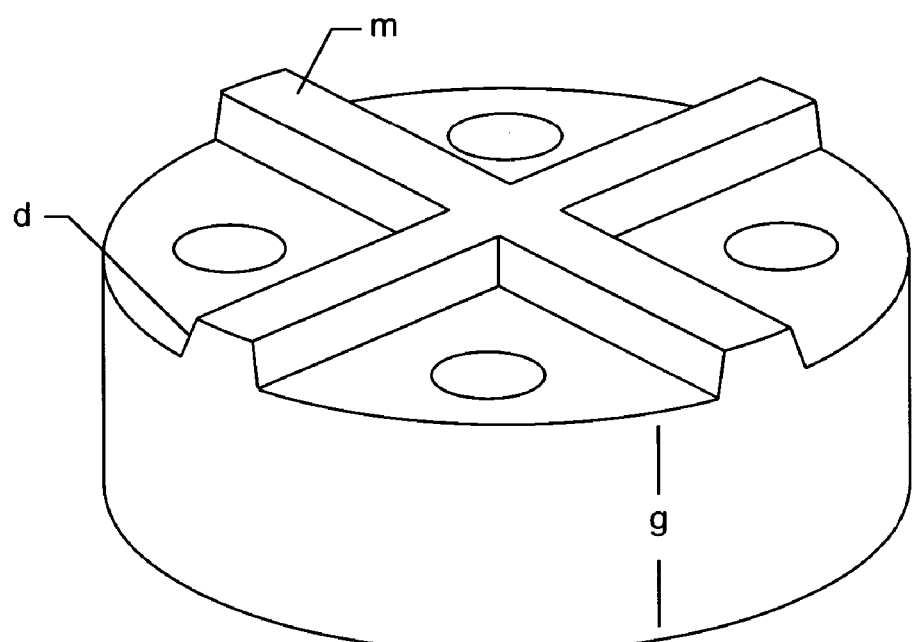
FIG. 78 is a perspective view similar to FIG. 77, illustrating an alternative configuration of the lossy ferrite inductor.

Comparing the outside diameter of the quad polar EMI filter shown in FIG. 75 to the outside diameter of the quad polar filter shown in FIG. 76, by using the novel slot technology as described in FIGS. 77 and 78, one is able to make the overall EMI filtered terminal smaller. It will be apparent to those skilled in the art that this novel slot or raised barrier technology in the ferrite inductor slab also applies to a wide variety of geometric shapes, including rectangles, dual inline filters and so on.

FIG. 78 performs a similar function in that it is a lossy ferrite inductor of the present invention. However, in this case the increased stand off distance from pin to pin has been accomplished by the raised protrusion areas as shown. It should be noted that for all of the ferrite inductor slabs as described herein, the lossy ferrite inductor has been coated with a suitable insulating material. In the preferred embodiment, this would be high temperature tempered Paralene D. Accordingly, the novel lossy ferrite inductors as described herein have excellent insulative properties and dielectric strength.

Referring back to FIG. 77, one can see the slope area d. This angular feature facilitates the manufacturing process. In a preferred embodiment, the novel lossy ferrite inductors as described herein are manufactured by powder formulations which are dispensed into carbon fixtures to create the desired shapes. They are then fired at very high temperature (sintered) to form a hard monolithic structure. It is after that that tumbling and Paralene coating is performed. However, after sintering, one must be able to remove the hard fired lossy ferrite inductor from the fixture. The angular feature d shown in FIGS. 77 and 78, simplifies this fixture release. This feature could be vertical, however, this would decrease manufacturing yields and also slow manufacturing time, as it would be very difficult to remove the fired ferrite lossy slab from the fixture. The fixtures used are typically of graphite or carbon and are somewhat fragile. By providing the angled tool feature d as shown in FIGS. 77 and 78, one also increases the lifetime and reduces the wear on the manufacturing fixtures.

Figure 79:
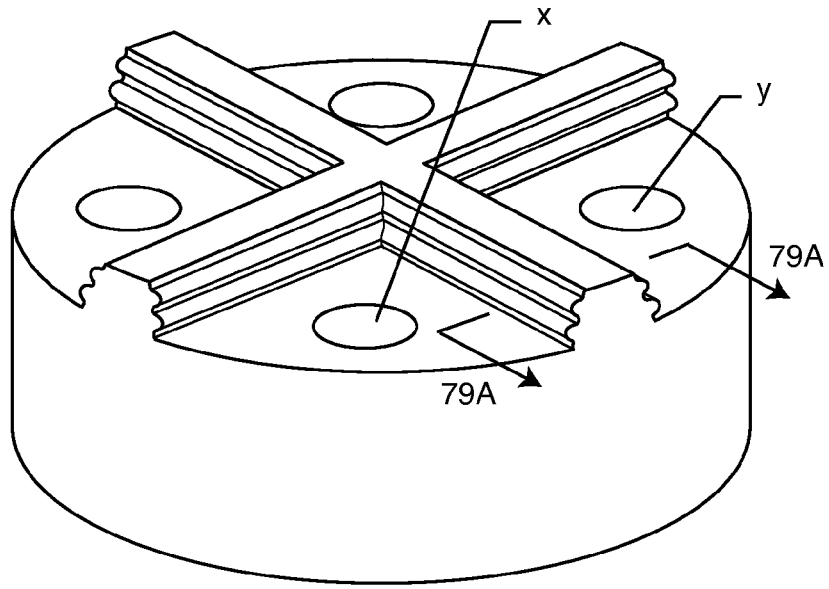
FIG. 79 is a perspective view similar to FIG. 78, illustrating an alternative embodiment thereof.
Figure 79A:
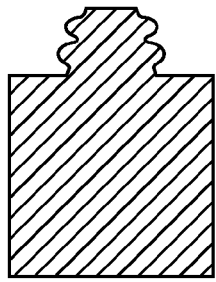
FIG. 79A-79C are sectional views taken generally along the line 79A-79A of FIG. 79, illustrating alternative cross-sectional configurations.
Figure 79B:
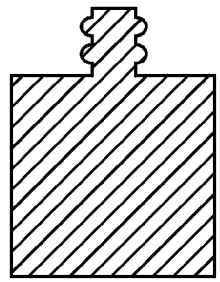
Figure 79C:
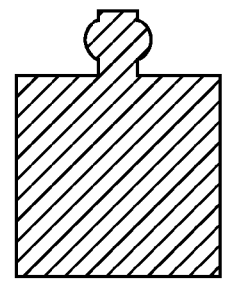

FIG. 79 illustrates alternative embodiments showing a convoluted structure similar to the insulator that would hang from a telephone pole. These convolutions greatly increase the creepage distance from pin to pin. Various cross-sections are shown in FIG. 79A, FIG. 79B and FIG. 79C. It will be obvious to one skilled in the art that any number of possible cross-sections are possible in order to increase the creepage path between the opposing pins, for example, between pins x and y of FIG. 79. The structure shown in FIG. 79 does present a significant fixturing issue during the sintering or firing of the lossy ferrite inductor. In this case, a multistage fixture would need to be manufactured which would be quite expensive to accomplish. For this reason, the structure shown in FIG. 79 is not a preferred option.

Figure 80:
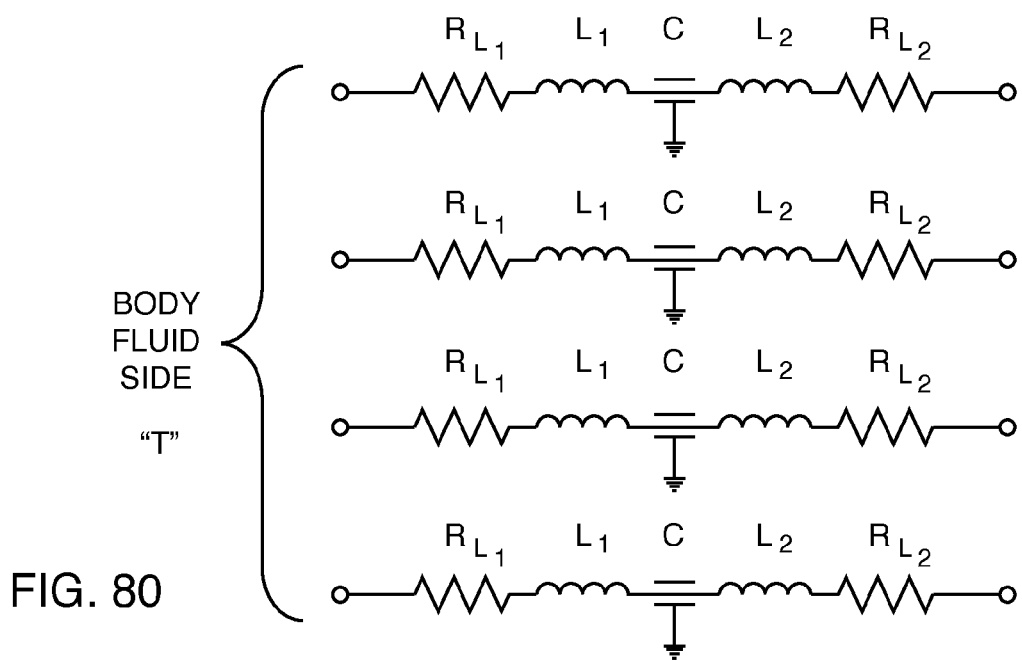
FIG. 80 is an electrical schematic diagram for the "T" circuit EMI filter shown in FIG. 75.

FIG. 80 is the schematic diagram of the quad polar EMI "T" filter shown in FIGS. 75 and 76. Referring once again to FIG. 80, the inductive and lossy elements $L_2$ and $RL_2$ come from the novel sintered ferrite slab shown in FIG. 77, 78 or 79.

Figure 81:
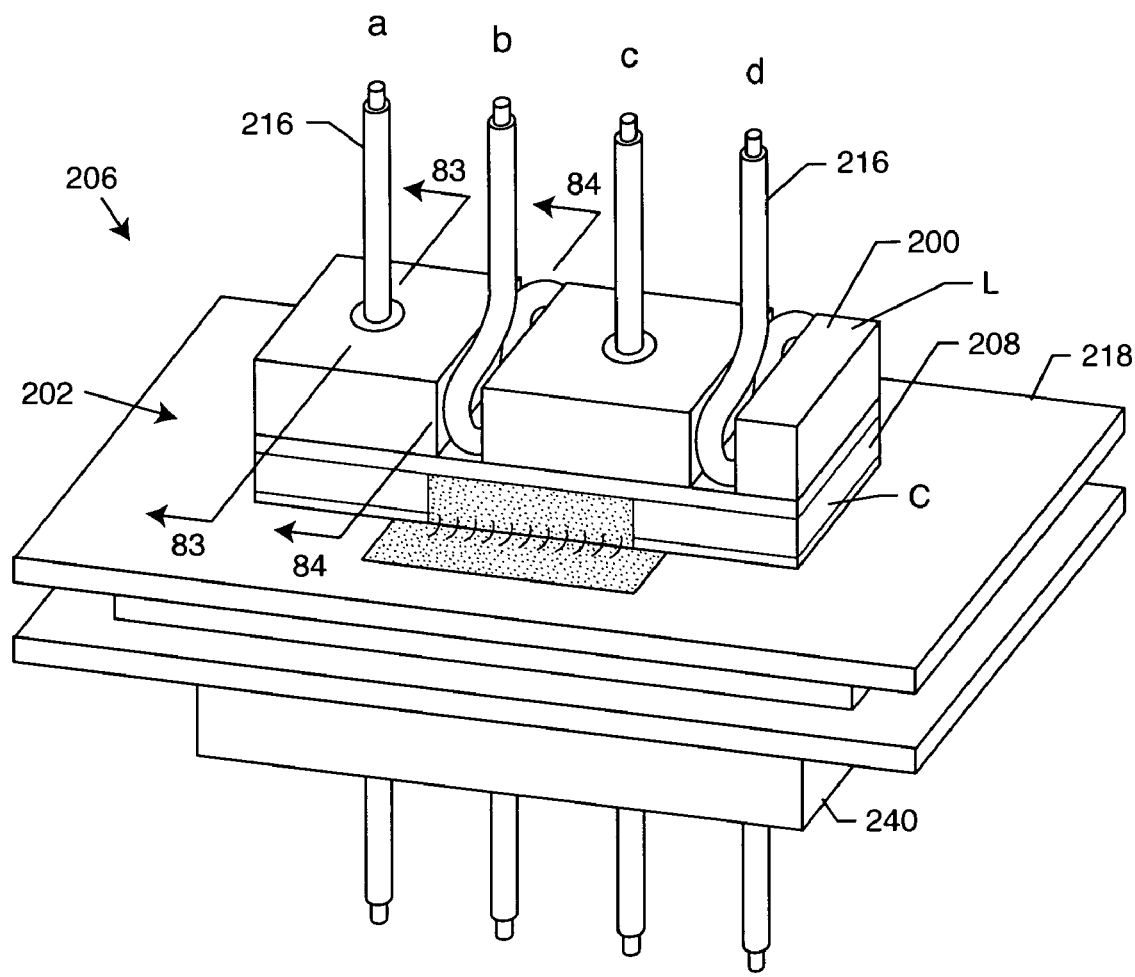
FIG. 81 is a perspective view of an inline quadpolar EMI "$L_1$" filter circuit with phase cancellation turns mounted to the terminal of an implantable medical device.

FIG. 81 is an isometric view of an inline quadpolar EMI filter 206 mounted to the terminal 218 of an implantable medical device. Feedthrough capacitor 208 is shown bonded in accordance with well-known prior art techniques to the hermetic terminal 202. Lossy ferrite inductor 200 has four (quadpolar) leadwires 216 that penetrate through it. The leadwires 216 that penetrate through the lossy ferrite inductor 200 that are labeled a and c, go straight through the lossy ferrite inductor 200 and perform very much the same as the lossy ferrite inductors as previously described herein. Leadwires a and b would typically be from one bipolar pair, for example, the bipolar TIP and RING leadwire system 220 implanted into the cardiac right ventricle. Leadwires c and d are from a different bipolar pair. The leadwires as illustrated at points b and d are designed to wrap around the lossy ferrite inductor 200 in the opposite direction. As previously discussed in FIG. 16, this produces cancellation vectors B within the lossy ferrite inductor 200 preventing it from saturating. This means that the permeability of the lossy ferrite inductor 200 is maintained even in the presence of high MRI fields. The leadwires b and d would typically be from a different bipolar lead, such as that implanted in the right atrium or outside the left ventricle. In a bipolar lead, such as the right ventricle lead pair, there is very little phase shift in the currents induced in the closely spaced TIP and RING wires from MRI. This is due to the wave velocity of propagation and the relatively close spacing of the TIP and RING leadwires. However, for a bipolar lead placed in the right ventricle (a and b) and a bipolar lead implanted in another physical location such as outside the left ventricle (c and d), there is enough spacing between the two bipolar lead pairs to create a substantial phase shift. Accordingly, the configuration shown in FIG. 81 is designed to take advantage of said phase shift and reduce ferrite slab saturation in the presence of MRI field gradients. This is in addition to the phase cancellation effect of wrapping the individual bipolar pairs in opposite directions through the ferrite slab (such as a and b if the right ventricle was connected to them). This gives the designer many options to handle phase cancellation.

Figure 82:
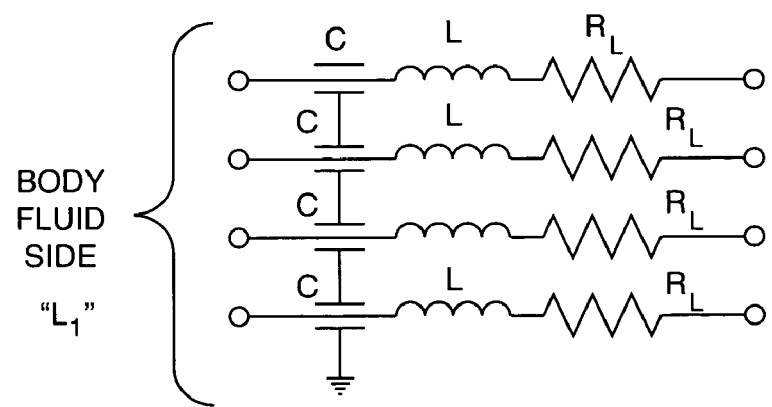
FIG. 82 is an electrical schematic diagram of the quadpolar "$L_1$" EMI filter shown in FIG. 81.

FIG. 82 is the schematic diagram of the "$L_1$" circuit quadpolar EMI filter described in FIG. 81.

Figure 83:
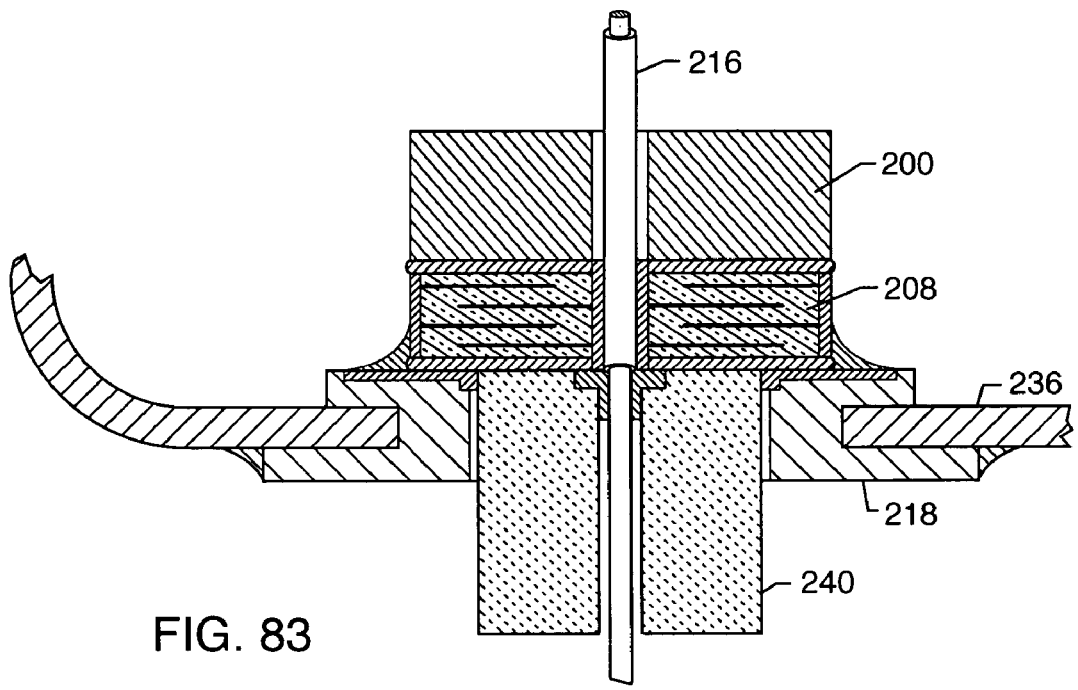
FIG. 83 is a sectional view taken generally along the line 83-83 of FIG. 81.

FIG. 83 is view 83-83 taken from FIG. 81 which shows the penetration of the leadwires a and c straight through the lossy ferrite inductor 200. As can be seen, leadwires a and c pass straight through both the feedthrough capacitor 208 and the lossy ferrite inductor 200.

Figure 84:
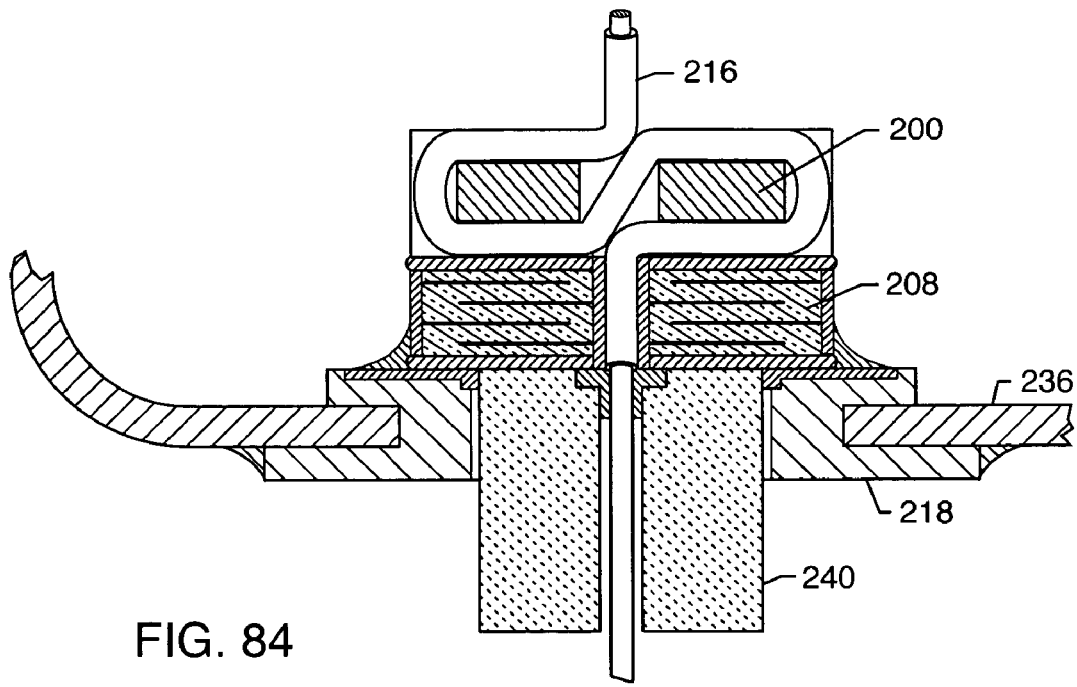
FIG. 84 is a sectional view taken generally along the line 84-84 of FIG. 81.

FIG. 84 is a cross-section from FIG. 81 taken from section 84-84. As one can see, the leads b and d are routed around lossy ferrite inductor 200 in such a way that they go through the center of inductor 200 in the opposite direction compared to leadwires a and c. This causes a phase shift for the induced EMI signals thereby producing additional cancellation vectors within the lossy ferrite inductor.

Figure 85:
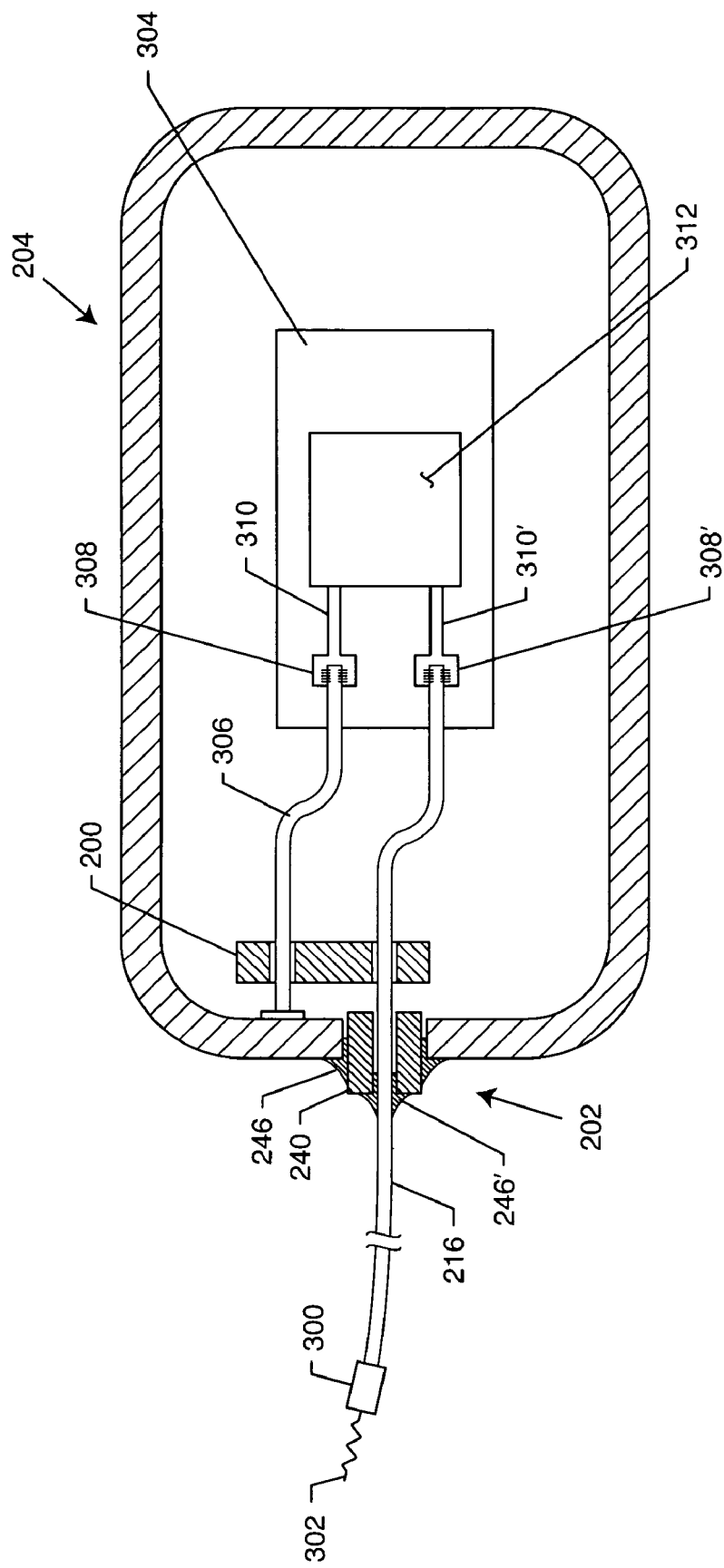
FIG. 85 is a sectional and schematic illustration of a unipolar active implantable medical device.

FIG. 85 is a typical active implantable medical device 204. This could typically be a unipolar cardiac pacemaker, a unipolar neurostimulator or the like. The device shown in FIG. 85 is a unipolar device in that, one leadwire 216 which can be of any length, extends from the implantable medical device 204 either through the venous system or through body tissue itself to a distal Tip location. The distal Tip 300 includes a probe 302 which is inserted into body tissue. The distal Tip can have a number of shapes which are common in the art. For example, in a neurostimulator, the distal Tip 300 would be placed in or around (as a coil) nerve tissue, for example, to block pain signals in the spinal cord. There is also a unipolar hermetic feedthrough 202 consisting of an alumina or glass insulator 240 which is then gold brazed 246 to the overall housing of the AMID 204. There is also a hermetic gold braze connection 246' made between the hermetic insulator 240 and the leadwire 216. Hermetic pin assemblies are well known in the art and can be combined with a ferrule as shown elsewhere herein. However, as shown in FIG. 85, a ferrule is not always necessary. In addition, the gold braze materials 246, 246', which are typically of gold, are also not always required. That is, glass copression seals can also be used to preclude the entrance of body fluids into the interior of the AIMD.

AIMDs typically employ a circuit board or substrate 304 as shown. This circuit board can be connected to an internal battery and various electronic devices in order to provide an output pulse to stimulate body tissue and/or sense biological signals. The output pulse can be directed to a number of leadwires, however, in FIG. 85, the simplest form is a unipolar device. In this case, the output pulse is stimulated to body tissue with reference to the AIMD can or housing and the distal lead Tip 302. In other words, the metal housing of the AIMD a forms one electrode and the other is the unipolar distal Tip electrode 302. As shown in other drawings herein, this is not always the case. In other words, it is not necessary that the AIMD housing (can) be a return electrode. For example, in a bipolar device the pulse could be solely between two or more implanted leadwires. In a cardiac pacemaker, this would typically be done using a bipolar lead, for example, in the right ventricle where there is both a distal TIP and a distal RING electrode.

Referring still to FIG. 85, one can see the novel lossy ferrite inductor 200 of the present invention which is positioned so that both the ground leadwire 306 and the active leadwire 216 pass through the ferrite inductor 200 in non-conductive relation. This is important so that the phase cancellation techniques as described in the present invention are utilized. That is, when this AIMD system is exposed to a powerful source of EMI such as that produced by MRI, signals will be induced both on the metallic AIMD can housing and on the distal lead system consisting of 216, 300 and 302. As these signals go through the ferrite inductor 200, they will produce a magnetomotive force which will result in magnetization forces within the lossy ferrite inductor 200 which will tend to be of different phases and partially or totally cancel one another. As described herein, this will help to prevent core saturation within the lossy ferrite inductor 200.

Referring once again to the circuit substrate 304, one can see that there are wire bond pads 308 and 308' which are connected to the leadwires 306 and 216. An attachment is made to the wire bond pad either by ultrasonic wire bonding, thermal sonic wire bonding, soldering or the like. Circuit traces 310 and 310' are then routed to the electronic circuit module(s) 312 of the AIMD.

The novel ferrite inductor 200 is shown in an intermediate location between the point of lead ingress into the implantable medical device housing and circuit substrate 304. As has been previously described in the present invention, one preferred embodiment would be to co-bond the novel lossy ferrite inductor 200 to the hermetic terminal assembly 202 a using a suitable co-bonding adhesive washer or polyimide washer. It would also be acceptable to co-bond the novel lossy ferrite inductor 200 directly to the circuit board 304 itself. What is important, is that the leadwires 306 and 216 pass through the novel ferrite inductor in non-conductive relation.

The novel ferrite inductor 200 provides two very important functions in the AIMD system. That is, the lossy inductor 200 raises the impedance of the leadwire system thereby reducing the levels of currents induced during MRI and other exposure to high intensity electromagnetic fields. Reduction of such currents reduces the amount of heating in the leadwire 216 and also the amount of heating at the distal Tip 302. Such heating can be damaging to body tissue, lead to tissue necrosis, or result in a higher pacing impedance for the AIMD thereby reducing its efficacy. Increased distal TIP impedance due to overheating means that the AIMD must stimulate at a higher output voltage. This is undesirable as this increases battery drain and leads to shortening the life of said device. The lossy ferrite inductor 200 also provides another very important function in that it acts as a one-pole low pass EMI filter thereby providing a degree of EMI protection to the sensitive electronic circuits of the AIMD. As described throughout the present invention, one can greatly improve the amount of EMI filtering by adding additional filter elements, such as feedthrough capacitors.

Referring once again to FIG. 85, the AIMD housing is typically of titanium, stainless steel or other metals that are biocompatible. However, it should be stated that the present invention is not limited to AIMDs that have a metallic housing. In fact, AIMDs can also have a ceramic housing or other insulative housing which protects the AIMD electronics from body fluid intrusion. Where the AIMD housing is insulative, a separate electrode is typically provided, for example, a platinum electrode located on the ceramic housing itself. There are certain AIMDs that incorporate a ceramic tube with a titanium end cap. The end cap forms the housing electrode. It will be obvious to one skilled in the art that the present invention, involving phase cancellation through a lossy ferrite inductor, could also include a ceramic housing with a separate co-attached electrode.

Figure 86:
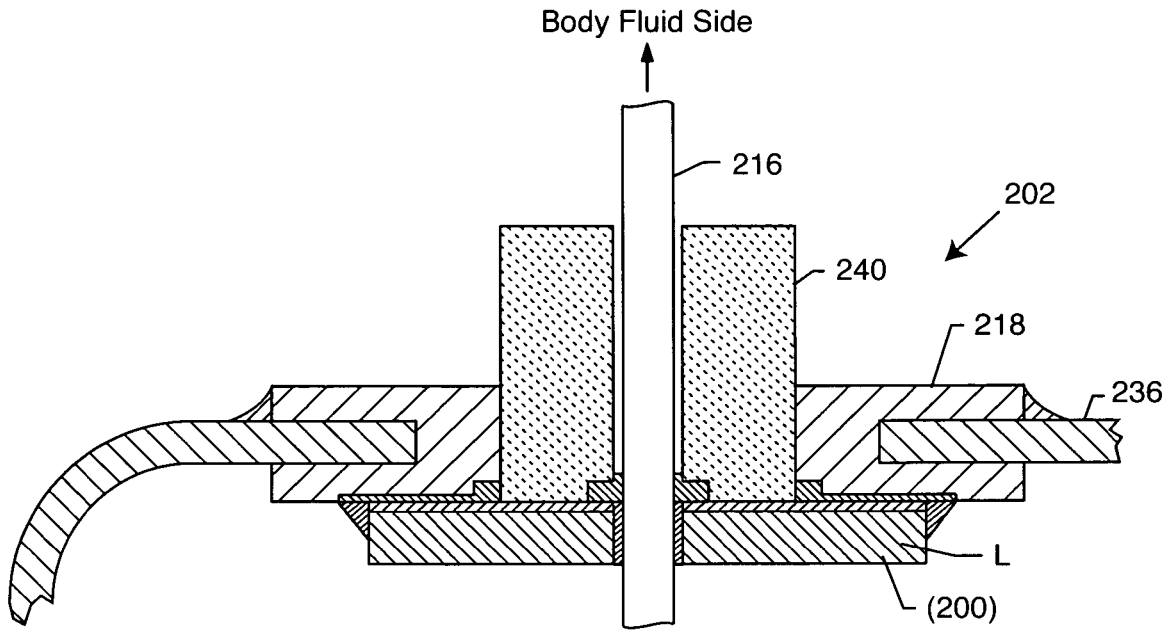
FIG. 86 is a sectional view of an unipolar lossy ferrite inductor mounted to the hermetic terminal of an implantable medical device.

FIG. 86 illustrates a unipolar lossy ferrite inductor 200 bonded to the hermetic terminal 202 of an implantable medical device. It is notable that there is no feedthrough capacitor in this particular application. Indeed, just the presence of a lossy ferrite inductor 200 by itself will greatly improve the immunity of the implantable medical device to high intensity EMI fields such as those created by MRI. However, the lack of a feedthrough capacitor would make the implantable medical device more sensitive to high frequency EMIs, such as that produced by cell phones and other emitters. Accordingly, FIG. 86 is not the preferred embodiment, but is a suitable embodiment if MRI is the primary concern.

Figure 87:
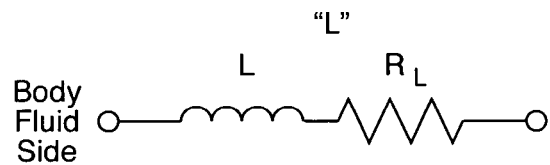
FIG. 87 is an electrical schematic diagram of the "L" circuit structure of FIG. 86.

FIG. 87 is a schematic diagram of the hermetic terminal 202 of FIG. 86.

Figure 88:
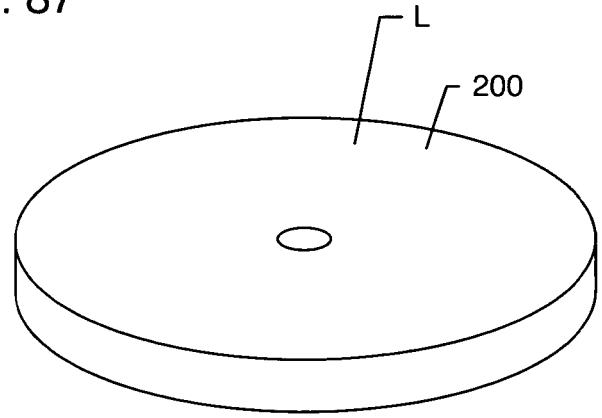
FIG. 88 is a perspective view of the lossy ferrite inductor illustrated in FIG. 86.

FIG. 88 is a close-up isometric view of the lossy ferrite inductor 200 illustrated in FIG. 86.

Figure 89:
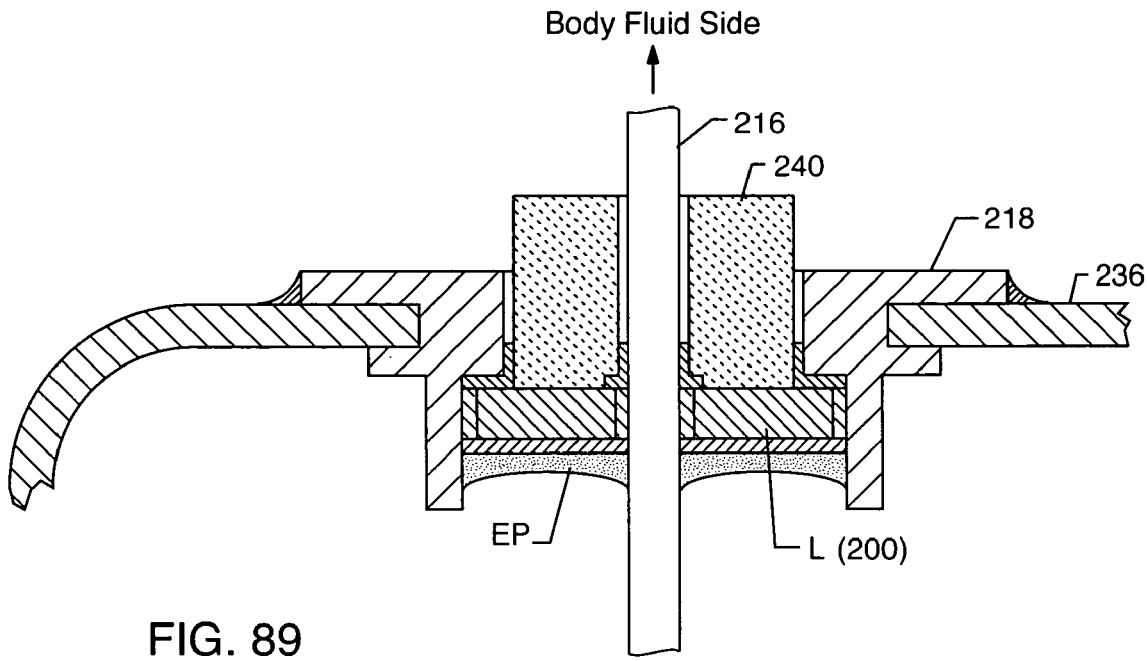
FIG. 89 is a sectional view similar to that shown in FIG. 86, except that the lossy ferrite inductor is imbedded within the flange of the hermetic terminal.

FIG. 89 is very similar to FIG. 86 except that the lossy ferrite inductor 200 is shown embedded within the flange 218 of the hermetic terminal 202. An optional epoxy fill EP can be added for cosmetic purposes.

Figure 90:
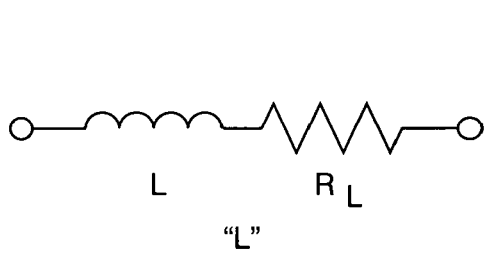
FIG. 90 is an electrical schematic diagram of the "L" circuit structure of FIG. 89.

FIG. 90 is the schematic diagram of FIG. 89.

Figure 91:
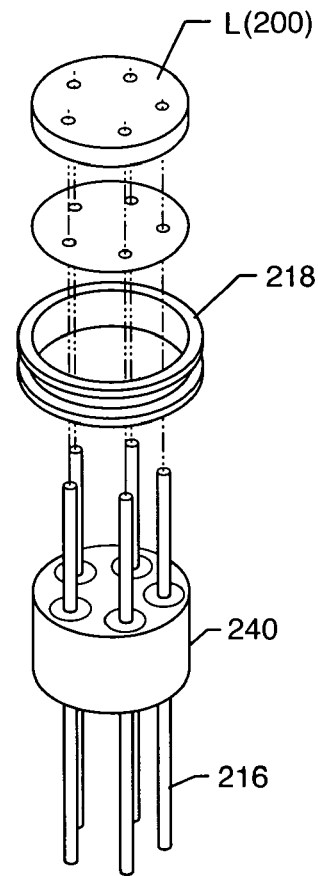
FIG. 91 is an exploded perspective view of a five-lead terminal including a lossy ferrite inductor ready for co-bonding to the terminal.

FIG. 91 is a five-leaded device showing a lossy ferrite inductor 200 ready for co-bonding to the hermetic terminal 202. The hermetic terminal 202 consists of a titanium ferrule 218 and alumina ceramic insulator 240. Hermetic sealing is achieved by co-brazing using a pure gold braze of the elements.

Figure 92:
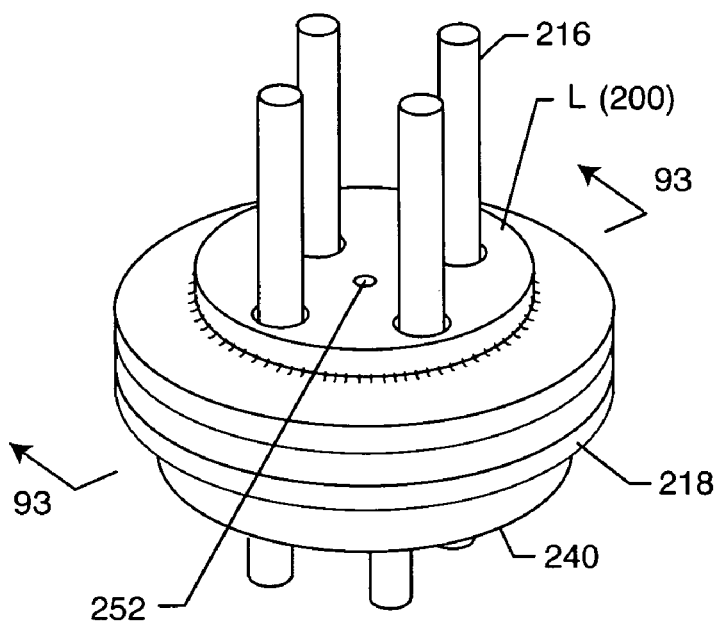
FIG. 92 is a perspective view of a hermetic terminal wherein the lossy ferrite inductor is imbedded within the flange, and including a leak detection vent hole to facilitate helium leak detection.

FIG. 92 shows a lossy ferrite inductor L (200) which is embedded within the flange 218 of the implantable medical device. This is better illustrated in the cross-sectional view shown in FIG. 93. One can see that the lossy ferrite inductor L (200) is embedded and encapsulated in a material so that it cannot move. Such material is a non-conductive epoxy material which is simply used to mechanically hold the lossy ferrite inductor 200 in place. There is no electrical attachment required or desirable between the lossy ferrite inductor and the flange 218. In fact, for all of the lossy ferrite inductors 200 as shown herein, the lossy ferrite inductor 200 has been treated with a suitable conformal coating material 244, such as Paralene to improve its dielectric breakdown strength or resistance to application of voltages.

Figure 93:
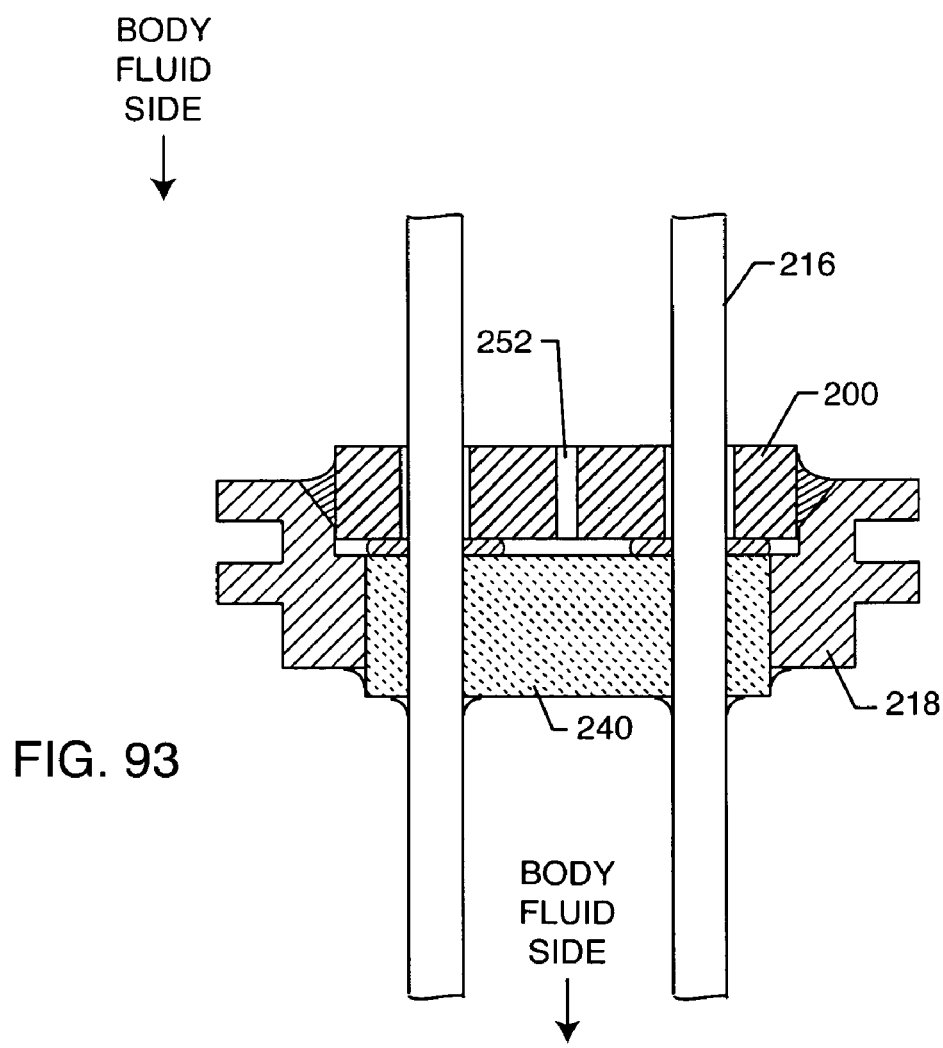
FIG. 93 is a sectional view taken generally along the line 93-93 of FIG. 92.

Referring now back to FIGS. 92 and 93, one can see that the lossy ferrite inductor L (200) has a novel leak detection vent hole 252 to facilitate helium leak detection.

Referring now to FIG. 94, one can see an inline quadpolar lossy ferrite inductor 200 similar to that previously described in FIG. 59, except that the feedthrough capacitor has been removed.

FIG. 95 is the schematic diagram of the lossy ferrite inductor L (200) of FIG. 94.

FIG. 96 shows an improved lossy ferrite inductor 200 which could be co-bonded to the hermetic terminal 202 shown in FIG. 94. The modified lossy ferrite inductor L (220) has been adapted to accommodate additional turns. The slot features keep these turns separated so adjacent turns will not short out. Using the lossy ferrite inductor 200 configuration illustrated in FIG. 96, two, three or even more turns can be used.

Figure 97:
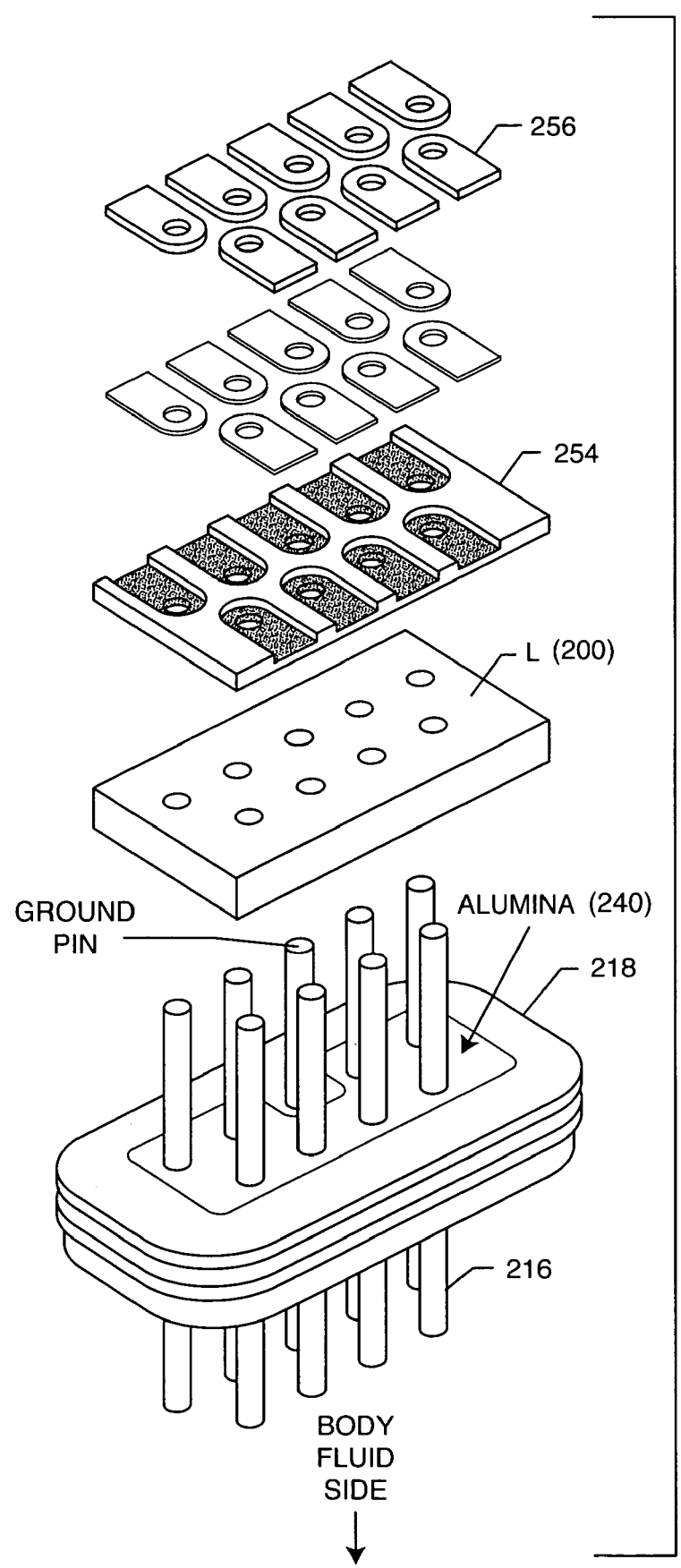
FIG. 97 is an exploded perspective view similar to that illustrated in FIG. 62, except that the internally grounded feedthrough capacitor has been removed.

FIG. 97 is very similar to that previously described in FIG. 62, except that the internally grounded feedthrough capacitor C has been removed.

FIG. 98A through 98D illustrate various examples of the shapes that the lossy ferrite inductor L (200) can take on. The lossy ferrite inductor 200 is preferably made of pressed powders. These powders are mixed with a binder system which is shape formed by pressing the powder into a die. The die can take on any shape of which is limited only by one's imagination. FIG. 98A illustrates a round lossy ferrite inductor. FIG. 98C is rectilinear. FIG. 98B is oval or elliptical and FIG. 98D indicates that any other shape with cutouts, T shapes or even triangles are possible. After the pressed pellet is formed, the lossy ferrite inductor is fired at high temperature sintering it into a hard monolithic structure.

Figure 99:
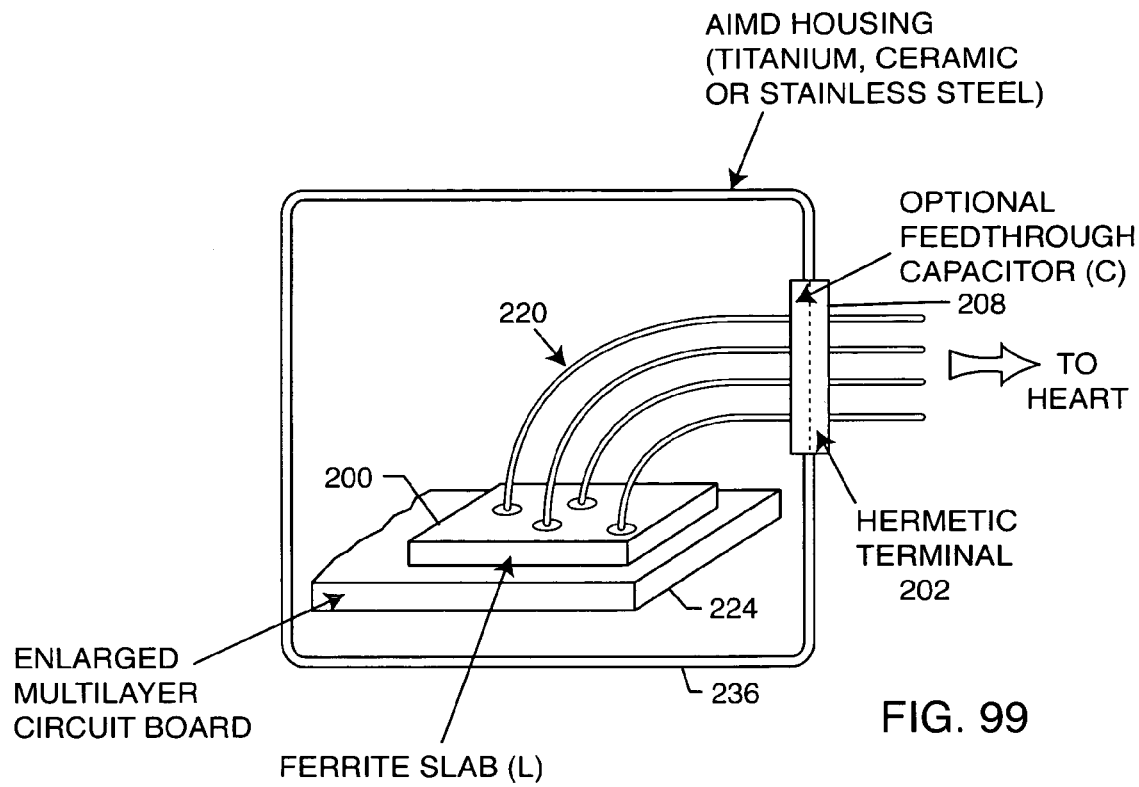
FIG. 99 is an illustration of the housing of a cardiac pacemaker with a hermetic terminal and a loss ferrite slab mounted to an internal circuit board.

FIG. 99 illustrates the housing 236 of a cardiac pacemaker 204 with a hermetic terminal 202 which is typically laser welded into the titanium housing 236. In this embodiment, however, the lossy ferrite inductor 200 is shown bonded onto a multilayer circuit board 224 (shown greatly enlarged). Of course, the implantable medical device 204 would have many other internal components, including a battery, reed switch, hybrid circuits, etc. The purpose of FIG. 99 is to indicate that the lossy ferrite inductor 200 will perform to raise the inductance anywhere it is placed in the circuit.

Figure 100:
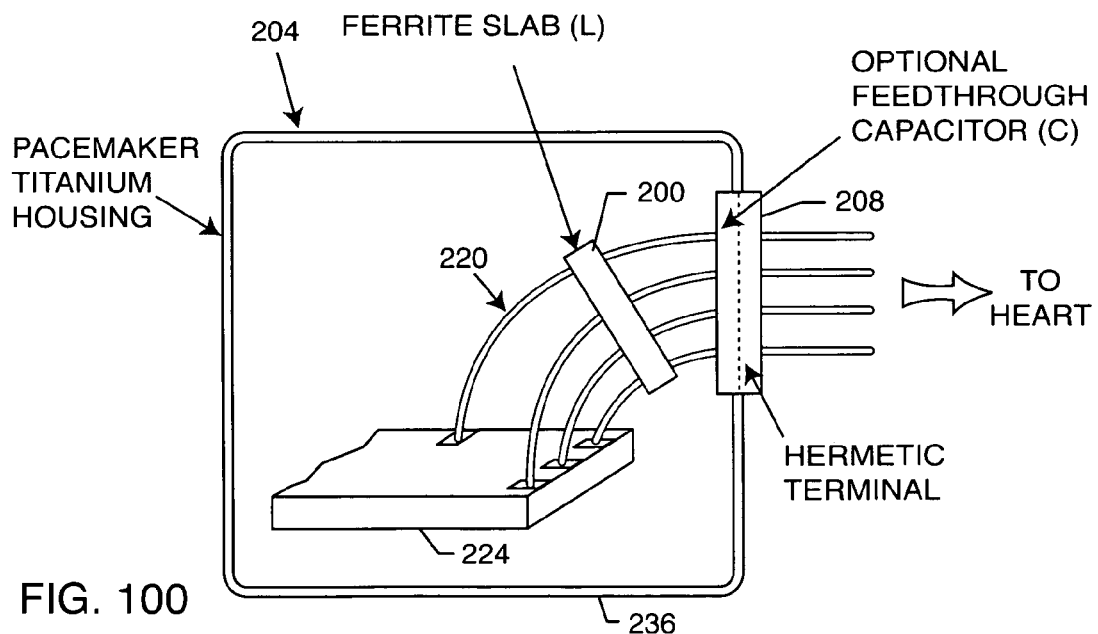
FIG. 100 is an illustration similar to FIG. 99, illustrating that the lossy ferrite inductor can be placed intermediate to the hermetic terminal and the circuit boards or other components within the active implantable medical device.

FIG. 100 illustrates that the lossy ferrite inductor 200 can be placed intermediate between the hermetic terminal 202 and circuit boards 224 or other components within the implantable medical device and perform to raise the impedance.

FIGS. 99 and 100 also show an optional feedthrough capacitor 208 which is well known in the art as a high frequency EMI filter. When the lossy ferrite inductor 200 is used in combination with the feedthrough capacitor 208, this makes a very effective L section filter as described in co-pending U.S. patent application Ser. No. 10/825,900. However, for the purpose of attenuation of MRI pulses, it would be desirable to have the lossy ferrite inductor 200 as shown in FIGS. 99 and 100 towards the body fluid side of the feedthrough capacitor 208. As previously described, this is important to reduce loop currents. Also, this isolates the relatively low impedance of the feedthrough capacitor 208 from the implanted leadwire system thereby reducing heating effects of MRI in the leadwire system.

Figure 101:
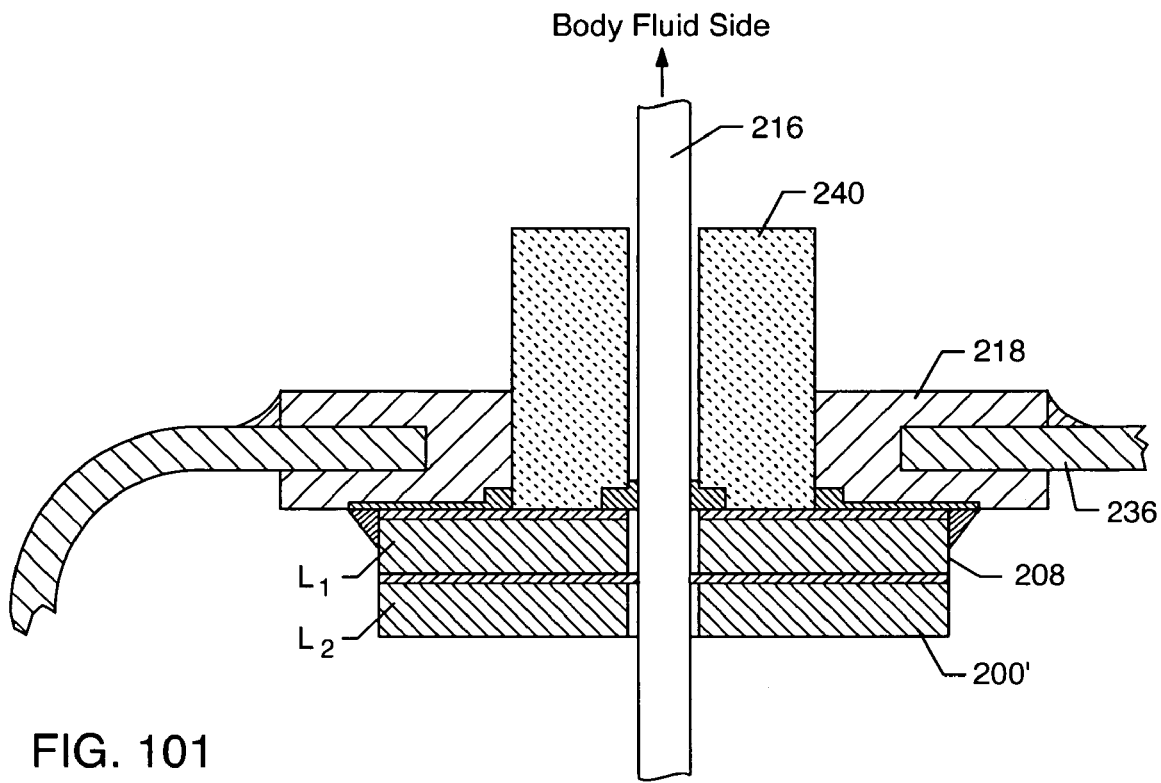
FIG. 101 is a cross-sectional view of an EMI filter embodying the present invention, illustrating multiple lossy ferrite inductors in stacked or laminated relationship.
Figure 103:
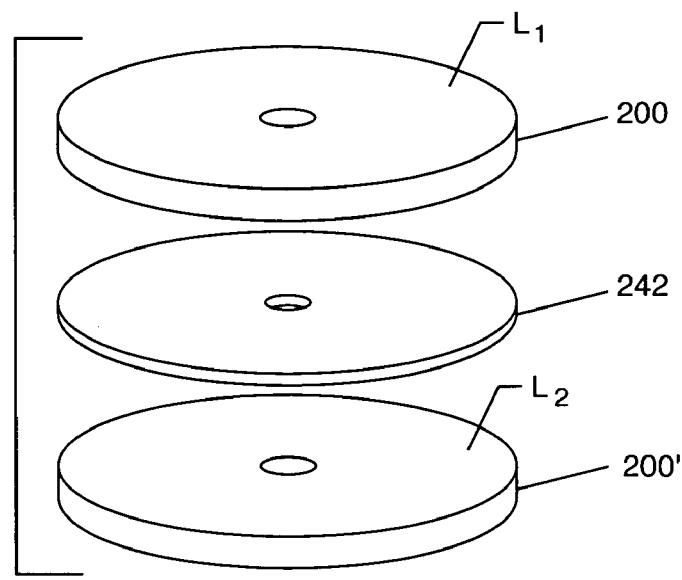
FIG. 103 is an exploded perspective view of the laminated lossy ferrite inductors of FIG. 101.

FIGS. 101 and 103 illustrate a novel feature of the present invention in that lossy ferrite inductors 200, 200' with a very small center hole can be manufactured and then layered to provide the overall height to optimize both the inductive and resistive properties. In FIG. 101 one sees that there are two ferrite slabs 200 and 200' which have been bonded together with a non-conductive insulating washer 242. This allows one to increase the overall height of the lossy ferrite inductor without running into the fixturing problems if one tried to manufacture this as a single element. As previously mentioned, for a single lossy ferrite inductor 200, the height and inside diameter ratio could be quite problematic in the manufacturing operation.

It will be obvious to one skilled in the art that two, three or a number of lossy ferrite inductors 200 can be co-bonded together to achieve any desired height and total inductance that is required.

Figure 102:
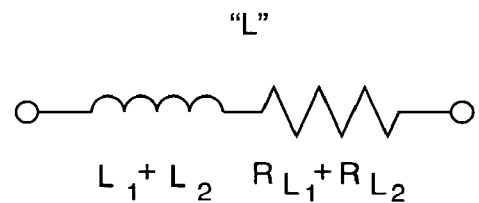
FIG. 102 is a schematic drawing of the "L" circuit EMI filter assembly of FIG. 101.

The schematic diagram shown in FIG. 102 illustrates the effect of having these two lossy ferrite inductors 200 and 200' acting in series with their two resistive properties acting in series. These elements simply add up which increases the overall inductance and the overall resistance of the lossy ferrite inductor. However, this does not change the basic EMI low pass filter circuit configuration. In other words, the addition of a second lossy ferrite inductor 200' means that the EMI filter of FIG. 101 still acts as a single element section filter. It is only when you separate the ferrite slabs by a capacitor element that you increase the number of poles or elements of the EMI filter, as described further herein.

Referring now back to FIG. 101, one can see that a plurality of lossy ferrite inductors 200 and 200' can be co-bonded together. These slabs can be of various initial permeabilities and properties. For example, the first slab 200 could be of manganese zinc material and slab 200' could be of cobalt zinc material. These two materials have markedly different electrical properties. One material has higher inductance at low frequency whereas the other material has higher inductance at higher frequencies. By co-bonding lossy ferrite inductors 200 and 200' of various materials together, one can optimize inductance throughout wider frequency ranges. The same is true of the resistive property $R_{L1}$ and $R_{L2}$ of the two lossy ferrite inductors 200 and 200'. Each type of ferrite material has different resistance versus frequency properties. By combining various materials one can also optimize the amount of resistance versus frequency.

Figure 104:
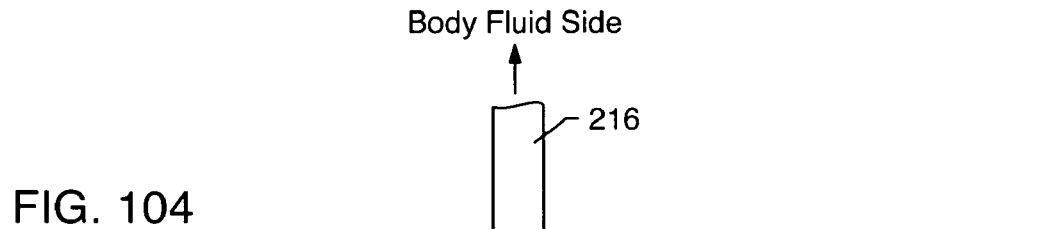
FIG. 104 is a cross-sectional view of an EMI filtered hermetic terminal assembly modified by shortening the alumina insulator thereof to provide a convenient bonding surface to install a second lossy ferrite inductor on the body fluid side of the assembly.
Figure 105:
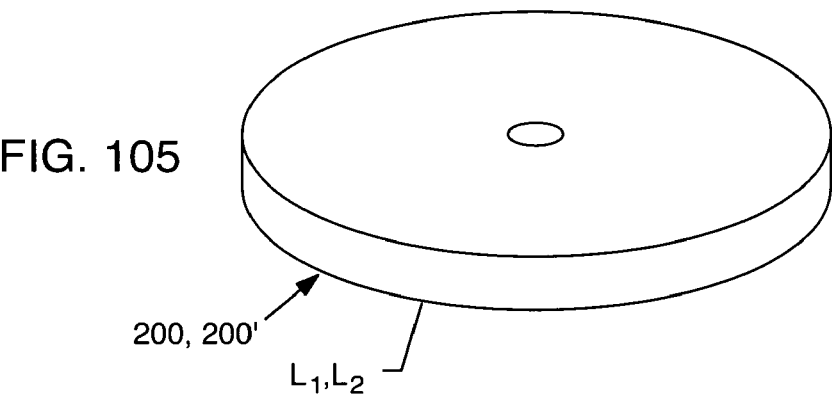
FIG. 105 illustrates the second lossy ferrite inductor of FIG. 104.
Figure 106:
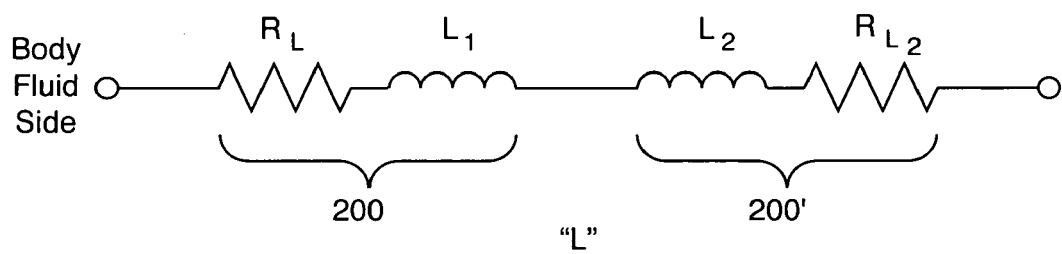
FIG. 106 is a schematic drawing of the filtered hermetic terminal assembly of FIG. 104.
Figure 107:
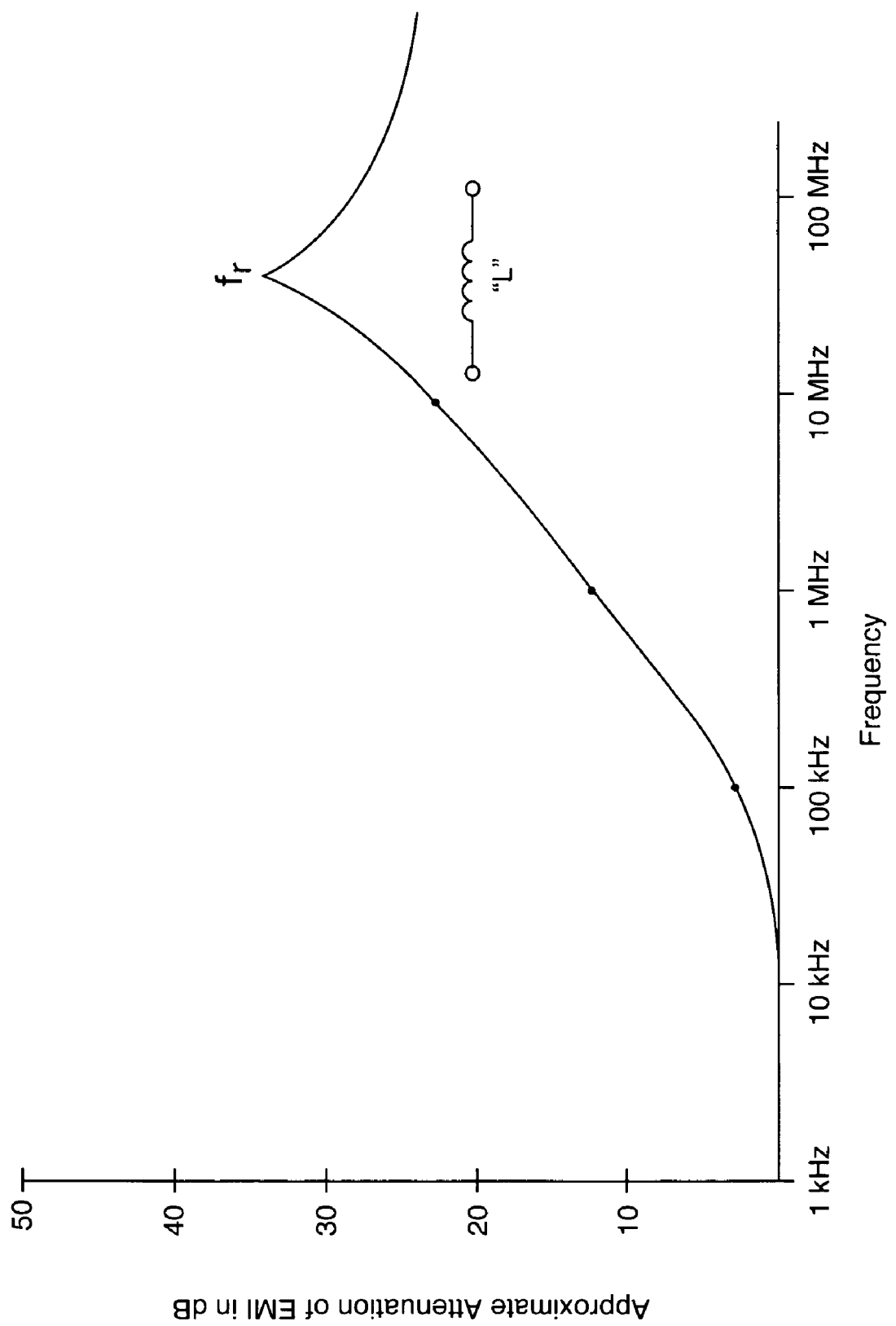
FIG. 107 is a curve showing attenuation of EMI of one filter of FIG. 104 in dB verses frequency.

Another novel method of building a single element ("L") circuit filter is the dual surface mount approach, illustrated in FIG. 104. In this case, the alumina insulator 240 has been placed completely inside a surrounding ferrule 218. Two lossy ferrite inductors 200 and 200' are then co-bonded to the insulator 240, with one preferably oriented toward AIMD circuitry as illustrated. An optional epoxy cap 258 can be placed over the top of the ferrite inductor 200, primarily for cosmetic purposes. The resulting circuit is illustrated in the schematic diagram of FIG. 106, which as shown in FIG. 107 gives rise to an attenuation slope of 20 dB/decade. FIG. 105 is an isometric view of loss inductor slabs 200 and 200' of FIG. 104.

Figure 108:
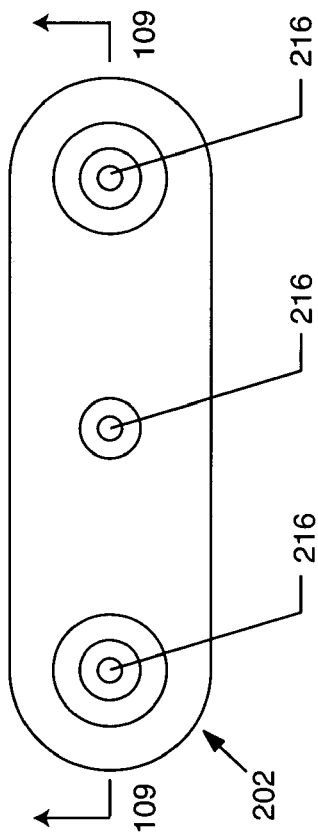
FIG. 108 is a plan view of an inline multi-polar EMI filter with a grounded pin.
Figure 109:
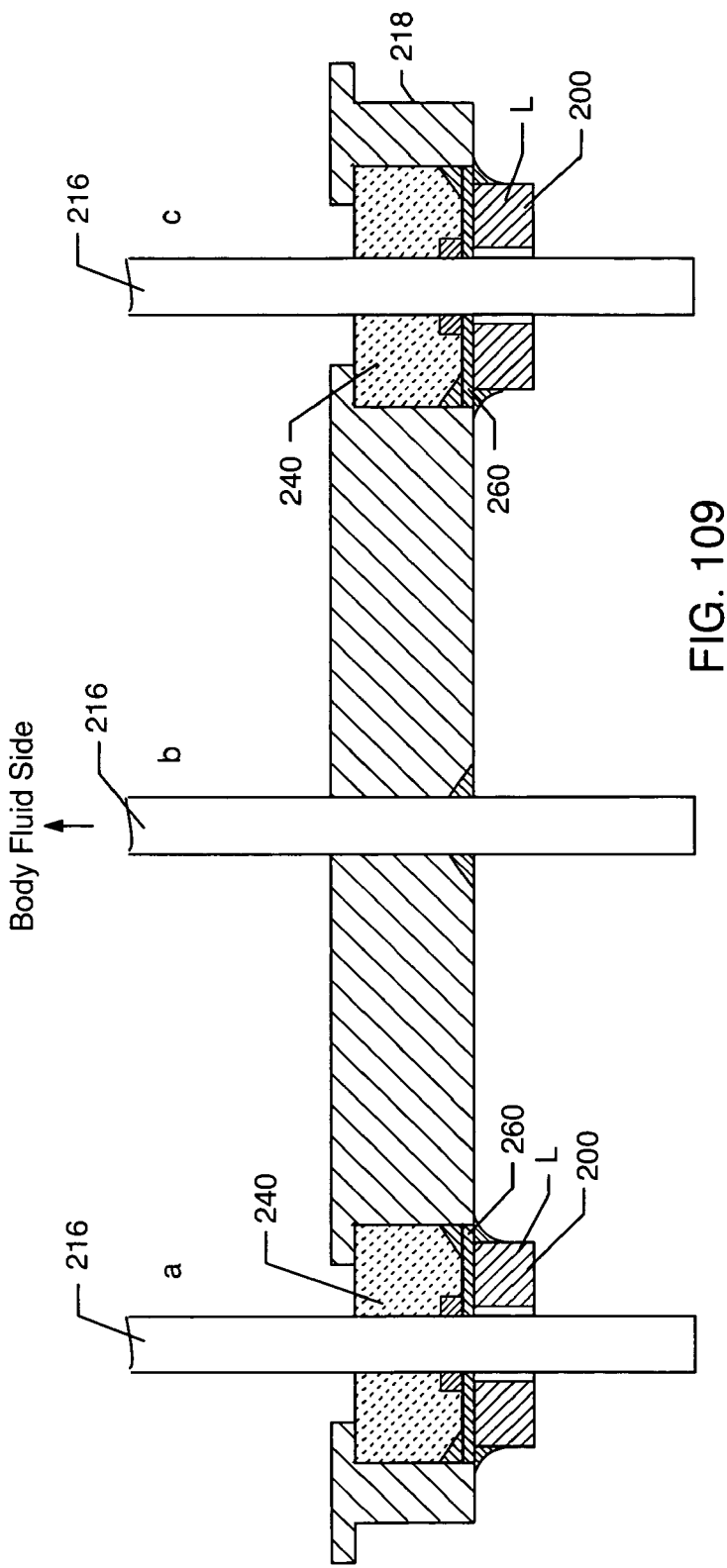
FIG. 109 is a cross-sectional view taken generally along line 109-109 of FIG. 108.
Figure 110:
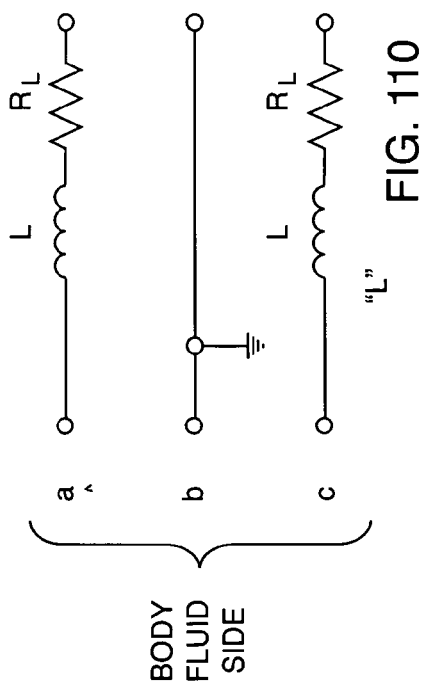
FIG. 110 is a schematic diagram of the "L" EMI filter assembly of FIGS. 108 and 109.

It is also possible to use discrete lossy ferrite inductors 200 as opposed to a single lossy ferrite inductor. FIGS. 108-110 illustrate an inline multi-polar hermetic terminal assembly 202 suitable for human implant such as in a cochlear hearing device. FIG. 109 is a cross-section of this device with multiple unipolar lossy ferrite inductors 200 co-bonded to the hermetic seal 240 in accordance with the present invention, such as by washer 260. FIG. 110 is the schematic drawing of the device shown in FIGS. 108 and 109, illustrating two parallel inductor filters. The schematic of FIG. 110 is shown conveniently as a bipolar or two line filter. In fact, in modern implantable pacemakers, a new therapy known as biventricular pacing has become very popular which requires additional leads. In addition, cochlear implants typically incorporate fourteen to sixteen leadwires. Accordingly, additional leadwires 216 are required. It is now common to see hermetic terminal assemblies with anywhere from four to sixteen leadwires.

Figure 111:
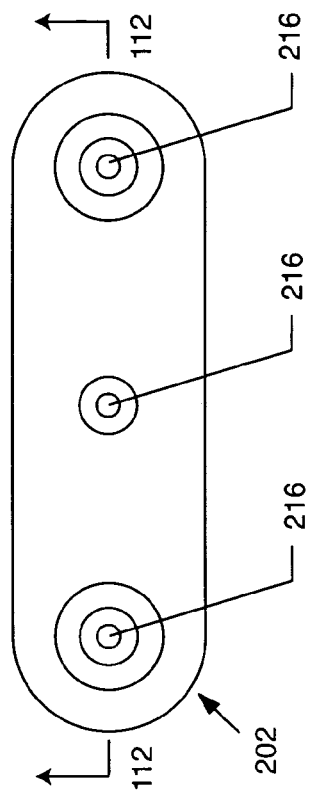
FIG. 111 is a top plan view of a multi-polar "L" EMI filter with a grounded pin, similar to FIG. 108.
Figure 112:
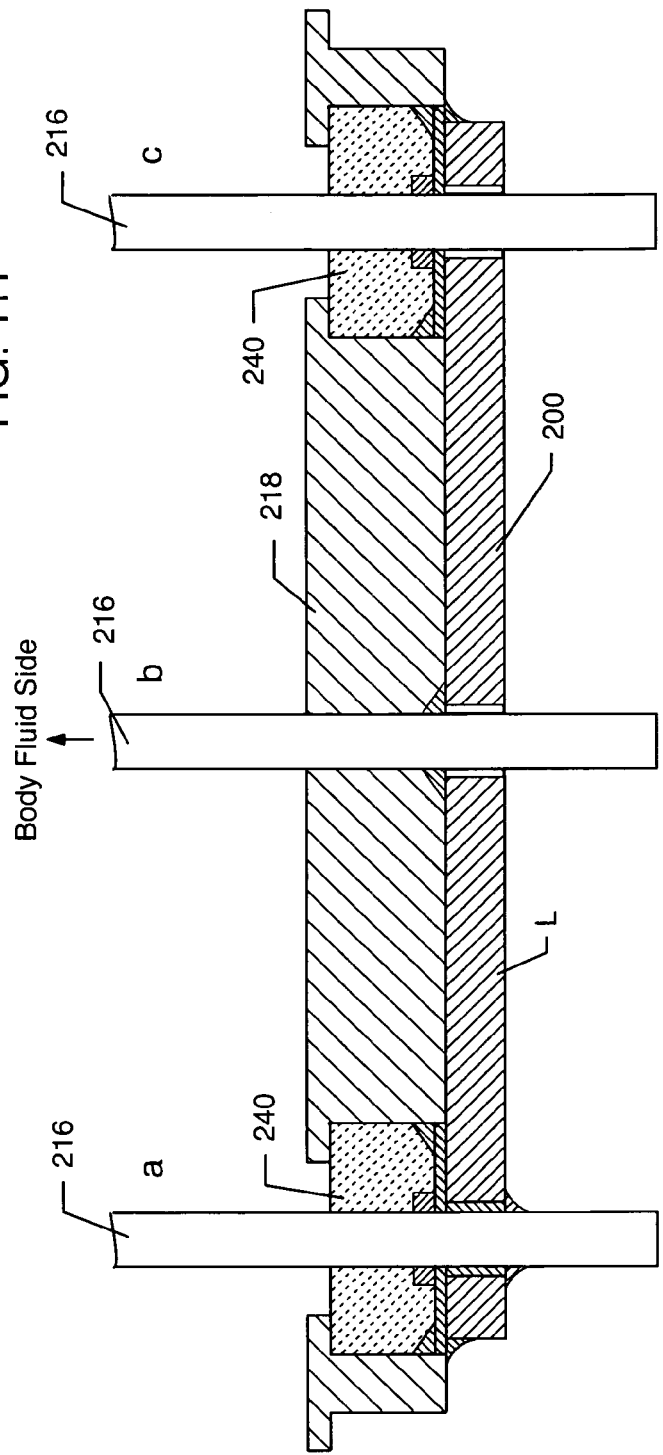
FIG. 112 is a cross-sectional view taken generally along line 112-112 of FIG. 111, illustrating the use of a lossy ferrite inductor instead of individual inductor beads.
Figure 113:
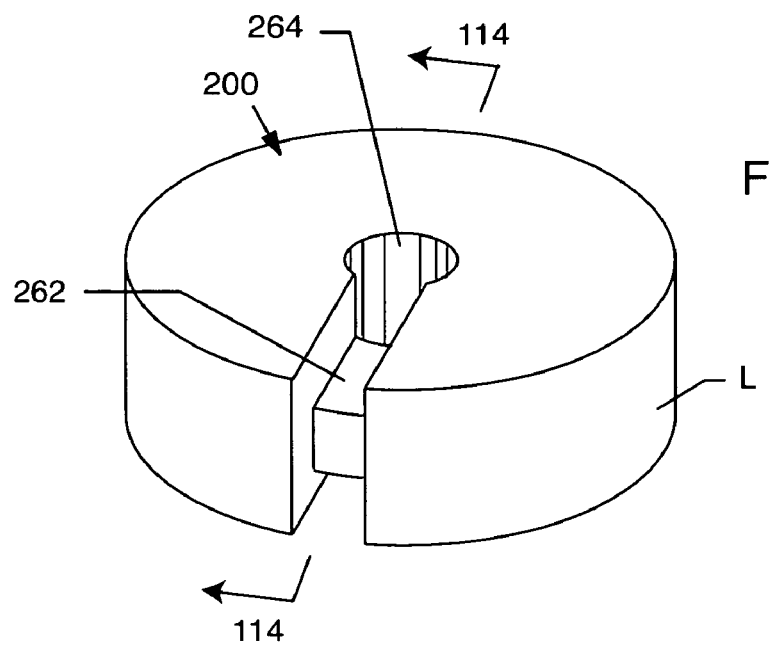
FIG. 113 is a perspective view of a novel lossy ferrite inductor having a notch in accordance with a preferred embodiment of the present invention.

FIGS. 111 and 112 illustrate the same device shown in FIGS. 108 and 109, except that instead of discrete lossy ferrite inductor elements 200, an elongated lossy ferrite inductor has been bonded to the unipolar hermetic seals 240. In this case, instead of using individual lossy ferrite inductors 200, a single lossy ferrite inductor 200 is employed which slips over and bonds to all of the alumina insulators 240 at one time.

As previously mentioned, the amount of series resistive loss and inductance that one achieves is very important to achieve overall attenuation. This is different than the attenuation slope measured in dB per decade. As one increases the capacitance and the inductance, the starting point (3 dB point) goes down in frequency and the overall attenuation increases dramatically. As an example, if one had a very low value of capacitance and a very low value of inductance, one might only have 5 dB at 100 MHz. Even though one had a two-element filter, which increases at 40 dB per decade, one would in this case be limited to only 45 dB at 1000 MHz (a decade higher than 100 MHz). However, if one was able to increase the capacitance value and increase the inductance value, one might have a starting attenuation at 100 MHz of 20 dB. This would mean that at 1000 MHz, one would have 60 dB of attenuation, which is very substantial indeed. Accordingly, there is a need for as much series resistive loss and inductance as possible in the lossy ferrite inductor element. It is not possible with conventional inductors to wind multiple turns around a lossy ferrite inductor once it has been co-bonded or mounted to a ceramic capacitor and the hermetic terminal of a human implantable medical device.

Figure 117:
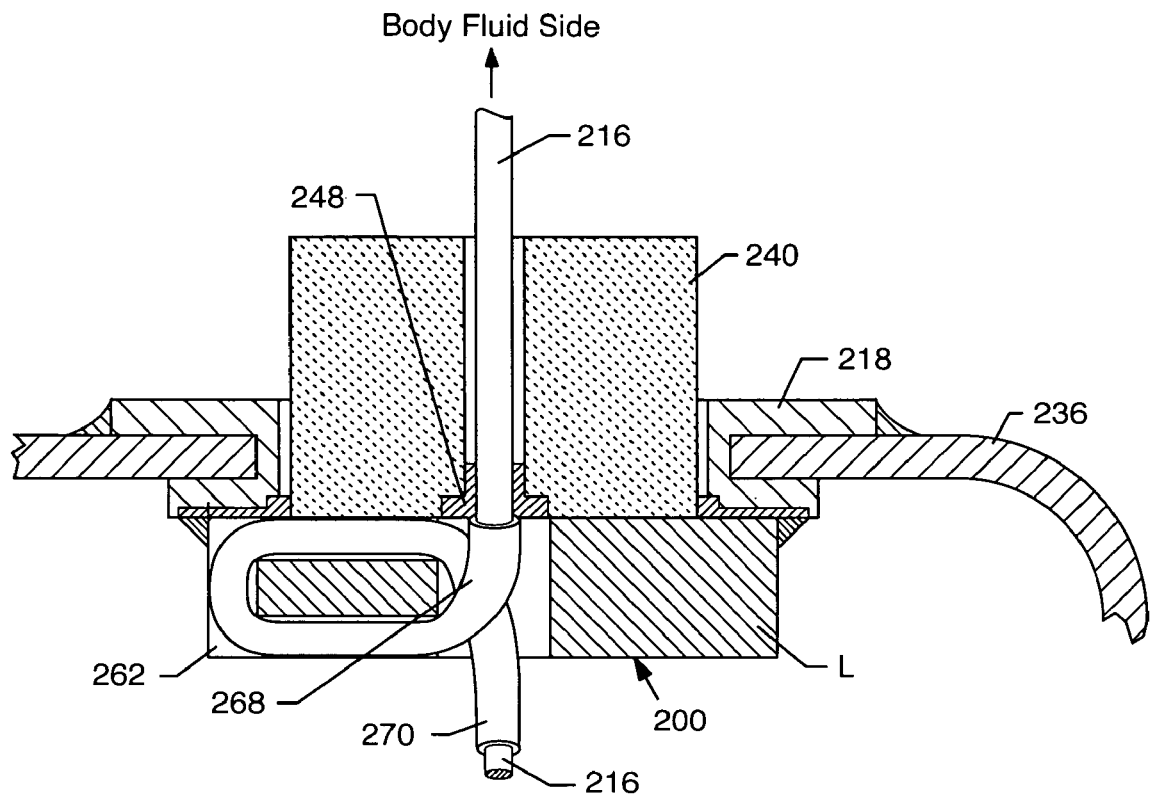
Figure 118:

FIGS. 113-116 illustrate a preferred embodiment of the present invention wherein a novel pressed indentation or notch 262 has been formed during the powder pressing or subsequent machining of the lossy ferrite inductor 200 and then sintered into a solid, monolithic inductor structure. Lossy ferrite inductors 200 are generally made of proprietary powders, which are put into multi-stage toggle presses. This pelletizing process (with binders) forms the ferrite element which is then sintered at very high temperatures creating a hard monolithic structure. It is a simple matter of mold tooling to form the notch 262 illustrated in FIGS. 114 and 115. As can be seen in FIG. 117, this makes it possible to bond the lossy ferrite inductor 200 directly to the alumina insulator 240 placing it over a single leadwire 216. It is then relatively easy to pass the leadwire 216 back around through and up through the center hole 264 of the lossy ferrite inductor 200 thereby adding another turn. In this case, we have described a two-turn inductor which increases the inductance by a factor of four ($2^2$).

Figure 114:
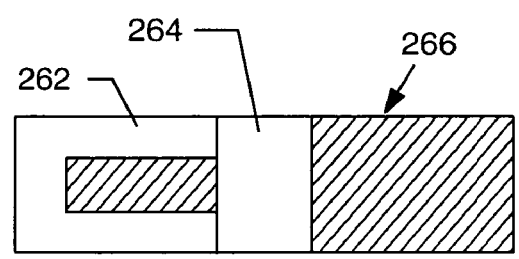
FIG. 114 is a cross-sectional view taken generally along the line 114-114 of FIG. 113.
Figure 115:
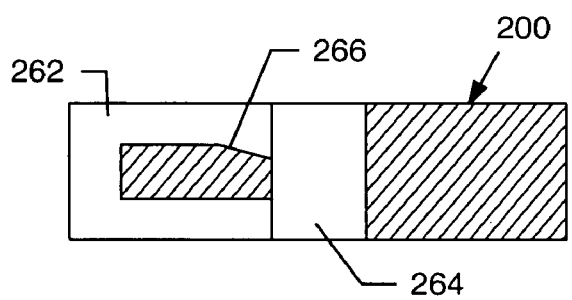
FIG. 115 is a view similar to FIG. 114, incorporating a ramp for facilitating feed of a multiple turn leadwire through the center hole of the lossy ferrite inductor.
Figure 116:
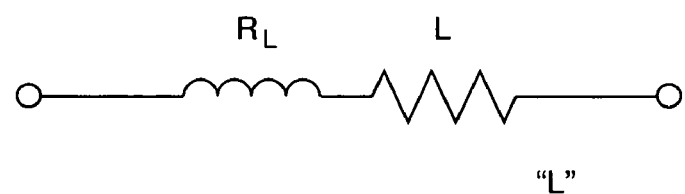
FIG. 116 is an electrical schematic drawing of the lossy ferrite inductor of FIG. 113.

FIG. 115 illustrates an improved embodiment of the novel lossy ferrite inductor 200 shown in FIG. 114 incorporating a ramp 266 upward thereby making it easier to feed the leadwire 216 back around and up through the center hole 264 of the lossy ferrite inductor 200. It is very important that a notch 262 not be cut all the way through which would form an air gap in the circular toroid. It is very important for a toroidal lossy ferrite inductor 200 that it form a very low reluctance path for magnetic fields. Field inductance in this case will still occur throughout the toroid wherein the magnetic field is constrained within the toroidal lossy ferrite inductor 200. By eliminating the air gap, we can provide a very high amount of inductance in a very efficient manner.

A unique aspect of all implantable medical device hermetic terminals is that the lead 216 is pre-manufactured to form a hermetic seal. In certain hermetic terminals, the lead 216 is attached to the alumina insulator 240 by gold brazing 248. In turn, the alumina insulator 240 is gold brazed to a titanium ferrule 218. In applications other than implantable medical device hermetic terminals, it is easy to manufacture multi-turn inductors because a loose leadwire is available for one or more turns around a toroidal inductor. However, in the case of an implantable medical device, a major problem arises in how to bond the lossy ferrite inductor directly to the insulator 240 and then to make a multiple turn. The novel molded notch feature, illustrated in FIG. 113, demonstrates a methodology in which the insulator 240 can be placed down over the leadwire 216 which is straight and then the leadwire 216 can be looped back through and around the notch 262 and brought out through the top yielding a two turn toroidal lossy ferrite inductor as shown in FIG. 117. As previously mentioned, the inductance is directly related to the square of the number of turns. The lossy ferrite inductor 200 shown in FIG. 117 is known in the art as a two-turn inductor. By squaring the number two, this means that this would have four times the amount of inductance as simply passing a leadwire 216 directly through the center 264.

It should be pointed out that the leadwires that are typically used in implantable medical devices must be of suitable biocompatible materials. Typical leadwires are platinum, platinum-iridium, tantalum, niobium and the like. As these leadwires 216 form multiple turns through the center of the lossy ferrite inductor 200, as illustrated in FIG. 117, it is very important that the turns do not touch one another. If for example, in FIG. 117 where the leadwire 216 loops around and crosses past itself in area 268 physically touched together, then this shorted turn would once again become a single turn inductor. This would not affect the inherent operation of the pacemaker, however, it would result in reduced EMI filter attenuation.

Figure 119:
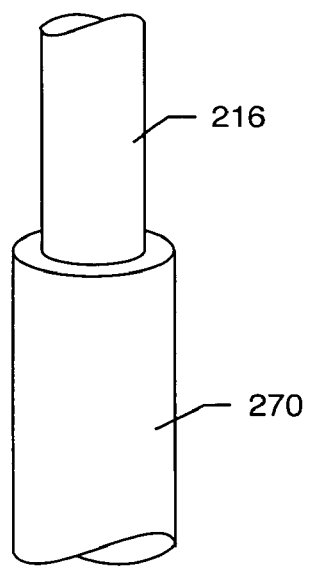

Accordingly, there is a need to insulate the turns where they pass each other through the center 264 of the lossy ferrite inductor 200. There are a number of ways of doing this. One way would be to slip on an insulating sleeve 270 as shown in FIG. 117 and shown expanded in FIG. 119. Suitable insulating sleeves 270 can be made of Polyimide, Teflon, Kapton, or the like and are very thin. They also have excellent dielectric strength characteristics and can be easily slipped over the wire 216. Other methods would include conformal coating of the wire 216 with a thin insulating material. It should be noted that there is very little voltage difference between the adjacent turns of the wire 216 passing through the lossy ferrite inductor 200. Therefore, not very much insulation or dielectric withstanding voltage requirement is necessary. Accordingly, a very thin coating of Paralene, polyimide, epoxy or other insulating material is all that is really required. Another methodology would be to carefully place the turns through the center of the lossy ferrite inductor 200 and then subsequently add an encapsulant or sealant such that the un-insulated wire turns cannot move into electrical contact with one another and therefore become shorted.

Figure 120:
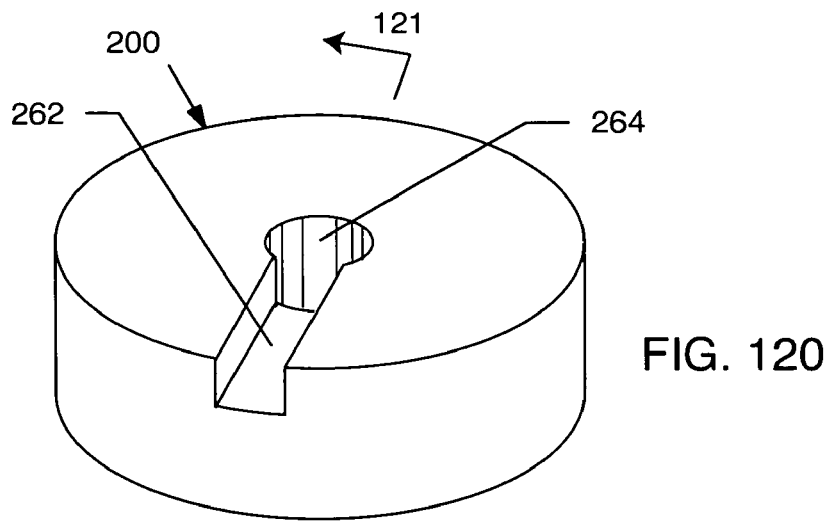
Figure 121:
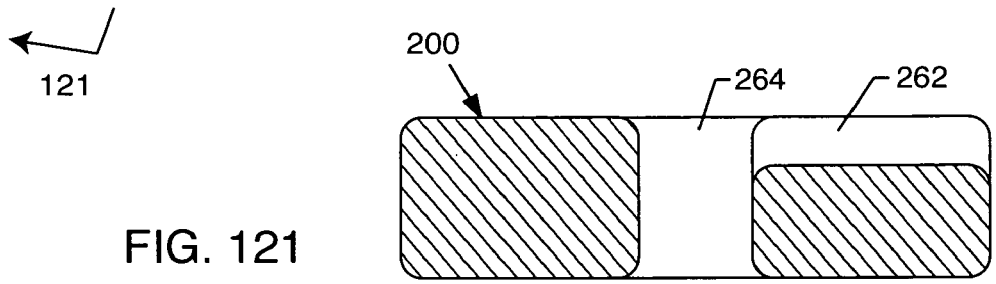
Figure 122:
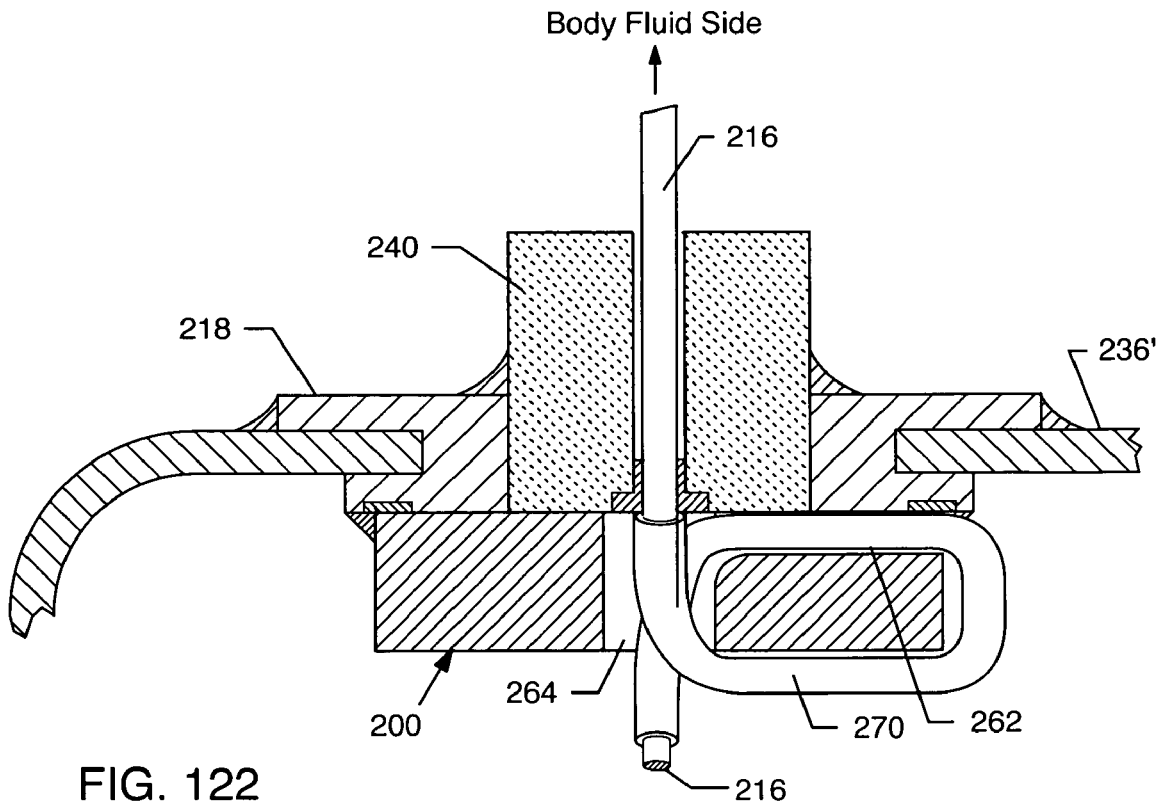

With reference now to FIGS. 120-122, yet another inductor lossy ferrite inductor 200 is illustrated having a notch 262 formed therein which is different in configuration than that illustrated and described above. As illustrated in FIG. 122, the lossy ferrite inductor 200 is co-bonded to the alumina insulator 240, similar to that illustrated in FIG. 113, but the leadwire 216 is brought through the center 264 of the lossy ferrite inductor 200 and then wrapped back around through the convenience notch 262 and back through the center hole 264 of the lossy ferrite inductor 200, therefore, forming a two-turn inductor.

As previously noted a two-turn inductor has four times the amount of inductance as a single turn inductor. The difference between this particular lossy ferrite inductor 200 and the one shown in FIG. 117, is that the notch 262 is only on one side of the lossy ferrite inductor 200. This has the effect of putting the leadwire 216 across the top of the lossy ferrite inductor 200. In some applications, where there is sufficient room inside the pacemaker, this would be desirable. However, in the preferred embodiment shown in FIG. 117 one would not have this leadwire 216 coming across the top of the lossy ferrite inductor 200. The choice is whether to use the configuration in FIG. 113, with a slot on top and bottom, as compared to the single slot shown in FIGS. 120 and 121. There is little performance difference in terms of attenuation in these two approaches.

Figure 123:
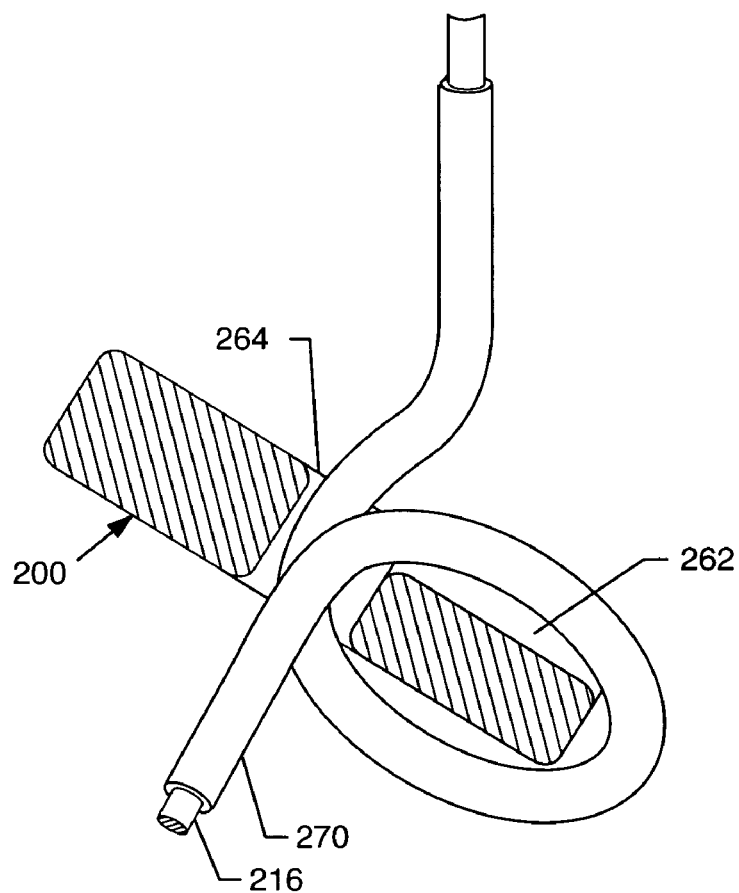

FIG. 123 illustrates an alternative method of manufacturing the two-turn inductor EMI filter previously illustrated in FIG. 122. In FIG. 122, a long leadwire 216 is elongated through the alumina insulator 240. An insulative tubing 270 is placed over the leadwire 216. It is desirable that insulative tubing 270 has a very low coefficient of friction. Such materials would be Polyimide, Teflon, Kapton or the like. A turn would be looped through the center and back around through the lossy ferrite inductor 200, as shown. It is desirable that lossy ferrite inductor 200 have rounded corners to facilitate slipping the lossy ferrite inductor down along the tubing to seat it on top of the alumina insulator. Once the loose loop is formed, one can simply grasp the end of the leadwire 216 and push downward on the lossy ferrite inductor 200, so that it slips along until it seats against the top of the insulator 240. The leadwire 216 can then be snugged up so that it fits within the notch space 262.

Figure 124:
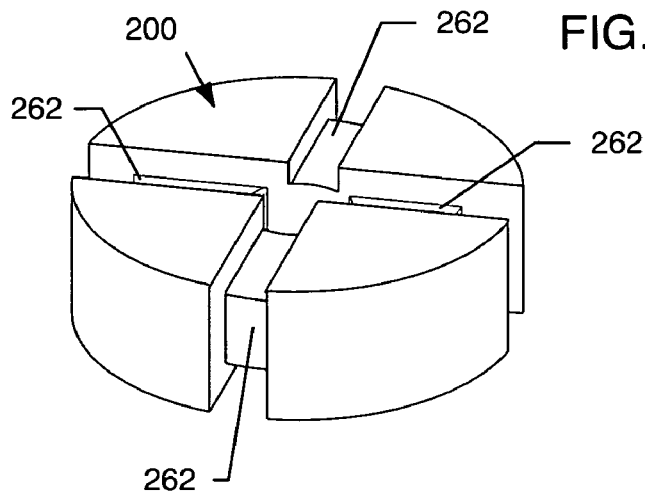
Figure 125:
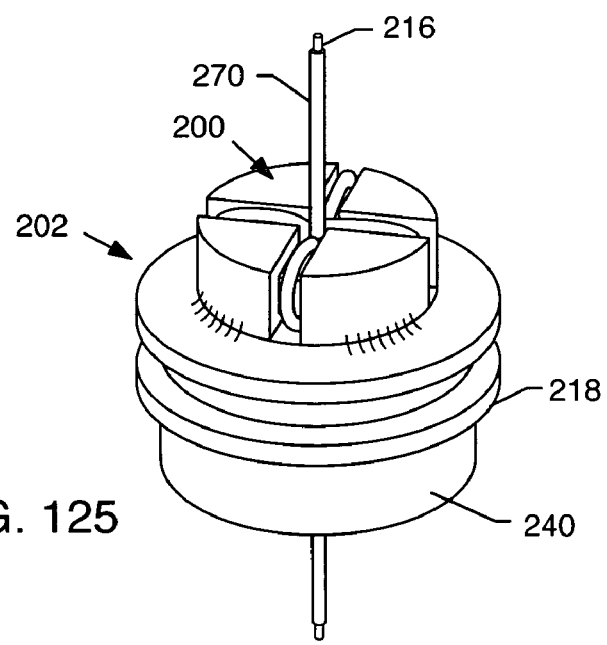

It is also possible to add additional turns. FIG. 124 illustrates a novel unipolar lossy ferrite inductor 200 with four novel slots 262. Accordingly, in this design, one could place four additional turns for a total of five turns through the lossy ferrite inductor 200. If we square the number of five this means that we would have twenty five times the inductance of a straight leadwire ferrite. FIG. 125 illustrates the novel five-turn lossy ferrite inductor 200 of FIG. 124 mounted to the hermetic terminal 202 of an implantable medical device.

Figure 126:
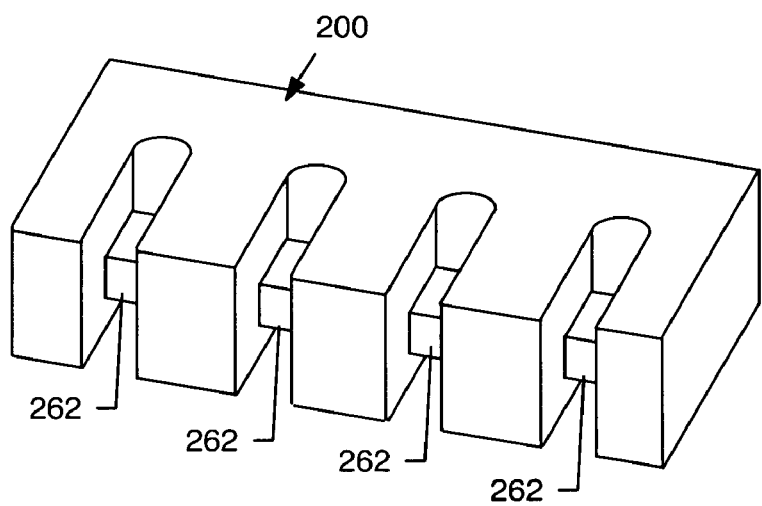

FIG. 126 illustrates a rectangular quadpolar lossy ferrite inductor 200 incorporating the features of the present invention. This allows each of the four individual EMI filters to have a two turn toroid, which will increase the inductance by a factor of four (2 turns squared).

The structure of FIGS. 127 through 130 are very similar to those previously described in FIGS. 92 and 93.

Referring to FIG. 127, the quadpolar lossy ferrite inductor 200 is loosely seated on top of insulator 240 without any bonding material. That is, lossy ferrite inductor 200 sits loosely on top of insulator 240. This is better illustrated in the cross-section shown in FIG. 128. There is an air gap 272 which is formed between the quadpolar insulator 240 and lossy ferrite inductor 200. As one can see, insulator 240 is relatively thick. This design can be used in cases where there is plenty of room in terms of height inside of the active implantable medical device.

Referring to FIG. 128, it is required that the lossy ferrite inductor 200 be retained so that it not fall off or separate away from the insulator 240 during shock and vibration loading. Accordingly, a number of different methods of holding the lossy ferrite inductor 200 in place are shown. One such method would be to place epoxy pre-forms 274 over each or a few of the four leadwires 216. A cross section of this heat cured epoxy pre-form 274 is also shown in FIG. 128. Another methodology would be to insert a metallic push nut 276 onto one or more of the leadwires 216. Another methodology would be to take a swaging tool and form a crimp or swage in the leadwire 278 as shown. This swage 278 is also shown in the cross section in FIG. 127. Another methodology would be to insert a retaining clip 280 as shown in FIG. 127.

In a multi-polar terminal assembly, it is not necessary to put a retention device on all of the pins. For example, in a six lead or hexpolar device, it may only be necessary to install a retaining feature on two of the leads. This depends on calculations based on the particular shock and vibration requirement of the implantable medical device. It is typical that shock requirements be between 1000 and 1500 g. One would have to calculate the mass of the ferrite slab and then calculate the amount of force that would be applied during such shock loading (F=ma). One can then make a decision as to the number of retaining devices that are required.

FIGS. 129 and 130 describe another embodiment of the quadpolar terminal assembly previously described in FIGS. 127 and 128. In this case, the lossy ferrite inductor 200 is retained by forming or bending one or more of the leadwires 216. It is a very common practice in medical implantable devices that the leadwires be formed or bent in a variety of shapes and configurations so that they line up with appropriate connection points to the internal electronic circuitry of the AIMD. Referring to FIG. 130 one can see that the bend 282 in leadwire 216 firmly holds lossy ferrite inductor 200 in place.

FIG. 131 illustrates a novel ferrite inductor slab 200 of the present invention. This is best understood by referring to the cross-sectional drawing of FIG. 132. This accomplishes a similar objective as previously described for the increased tortuous path novel and lossy ferrite inductor described in FIG. 77. Referring once again to FIG. 132, one can see that the pressed powder in sintered lossy ferrite inductor 200 has a novel counterbore feature CB as illustrated. There is a small diameter hole y which is optional. The smaller diameter counter-bore hole y allows the novel ferrite inductor slab 200 to be self-centering or self-locating. This keeps the pins 216 centered within the counterbore CB. This is important in order to guarantee that there is an increased tortuous path between pin to pin and between pin to ferrule 218. Referring to pin 216, one can see that in order for a high voltage arc to occur along surfaces that high voltage arc would have to travel first across surface a then up through b then across c and down surface d and then across surface e to pin 216'. This greatly increases the path length compared to previous embodiments where it would be possible to arc straight across surface c particularly if the ferrite slab was off center and touching off on the pin.

It will be obvious to those skilled in the art, that the counterbore feature CB could go all the way to the bottom. In other words, eliminating the smaller diameter y. In this case, centering the fixture would be required to ensure that the novel ferrite slab was exactly centered on the pins in order to guarantee that the tortuous path exists. The novel lossy ferrite inductor as illustrated in FIG. 132 has another key advantage and that is that it also increases the tortuous path between the pins and the ferrule ground surface 218. Referring once again to FIG. 132, one can see that for a high voltage arc to occur across the surfaces between pin 216' and the ferrule 218 that the arc would have to travel first up surface y then across g then down h before it contacted the point of opposite polarity on the ferrule 218. As previously mentioned, all of the lossy ferrite inductors that are described herein have been coated with a suitable insulation material such as Paralene D or equivalent. It will be obvious to those skilled in the art that the novel sintered ferrite inductor slab shown in FIGS. 131 and 132 are applicable to all of the drawings of the present invention. It will also be obvious to one skilled in the art, that the novel ferrite slab as illustrated in FIG. 132 could also be placed on the body fluid side.

Referring now back to FIG. 22 one can see that simply by properly centering the lossy ferrite inductor 200 on leadwires 216 that one can also accomplish a torturous path. Referring once again to FIG. 131, the counterbore areas are simply an automated way to provide sintering. As shown in FIG. 22 if appropriate production fixturing and tooling is used such that the ferrite slab 200 is properly centered then one also achieves a torturous path. Referring to FIG. 22 the torturous path between the two leadwires 216 would be accomplished across surfaces a, b, c, d and e. Accordingly, a similar torturous path would exist between the leadwire and ground which is also the feedthrough capacitor outside diameter metallization 206. This path would consist f, g, h and i. Accordingly, it is a novel aspect of the present invention that a centered lossy ferrite inductor which has appropriate conformal insulative coating can also be used to create a torturous path and grade the high voltage fields that would exist in a typical implantable medical device. Such high voltage fields can occur in the output of a high voltage implantable defibrillator. However, even in a low level pacemaker application, high voltage fields often appear at these terminals due a external defibrillation. Automatic external defibrillator (AEDs) are now present in airplanes, airports, and even in homes.

With reference to FIG. 133, in an implantable defibrillator application one can think of the circuit as having a high energy storage capacitor which stores roughly 30-40 joules of energy that is fully charged at the time the implantable defibrillator makes the decision to provide a high voltage shock to the patient. At this moment in time, the feedthrough capacitor C (208) as illustrated in FIG. 2 is completely uncharged. When the implantable defibrillator delivers its high voltage therapy this means that the feedthrough capacitor C (208) must charge up almost instantaneously. It also presents a potential problem for the ICD timing circuitry. A the implantable defibrillator output wave front charges capacitor C (208), some of this energy is reflected back towards its sensitive timing circuits. It has been demonstrated that this can disrupt the proper operation of the ICD. In certain cases, it has been documented that the ICD electronics can mis-time, can re-set or even permanently fail.

For these reasons, it is commonly known in the art that in implantable defibrillator applications the value of the feedthrough filter capacitor C is limited. In a typical pacemaker application C, may be as high as 9,000 picofarads. However, in an implantable defibrillator application the capacitance value is generally limited to 1,000 to 2,000 picofarads. The lower capacitance value places less loading on the implantable defibrillator circuit and creates less problems with circuit timing.

A novel feature of the present invention is that the inductor 200 which is placed towards the electronic circuitry of the implantable defibrillator, acts to decouple the feedthrough capacitor 208. The novel lossy and resistive properties of inductor slab 200 slow the ICD pulse rise time into the uncharged feedthrough capacitor 208. The lossy inductor slab 200 also helps to reduce the amount of circuit oscillation or ring back as the feedthrough capacitor 208 overcharges and then tries to discharge back into the ICD timing circuitry. Accordingly, it is a feature of the present invention that the novel lossy inductor slab technology also not only provides a higher level attenuation to EMI signals but also serves to protect the sensitive circuits of an implantable defibrillator.

In conjunction with this, it is now possible to actually raise the value of the feedthrough capacitance 208 to a higher value in order to provide a higher degree of the EMI filtering and immunity.

FIG. 134 shows the cross section of the L circuit EMI filter of FIG. 133.

FIG. 135 illustrates the schematic diagram of the quadpolar filter of FIG. 134.

The aforementioned discussion relating to the decoupling of the implantable defibrillator also applies to other circuit configurations. For example, in a T circuit configuration one also has desirably a lossy ferrite inductor slab disposed between the feedthrough capacitor element and the sensitive output circuitry of the implantable defibrillator. It will be obvious to one skilled in the art that in any of the circuit configurations where an inductor isolates the output of the implantable defibrillator from the rest of the EMI low pass filter circuitry then desirable decoupling is achieved.

Referring now to FIG. 136, one can see that this is a double L (LL) circuit configuration.

FIG. 137 is a schematic diagram for the LL filter of FIG. 136.

As previously mentioned, in the presence of both the static and pulsed MRI fields, circulating currents are set up in the implanted leadwire system. Referring to FIG. 9, these currents circulate in a loop on the body fluid side from leadwire 226 which we can consider to be the distal TIP and then back through the distal RING 228. As mentioned it is a desirable feature of the present invention to have the feedthrough capacitor $C_1$ be isolated from this loop since the feedthrough capacitor C, prevents a very low impedance and tends to increase the current in the leadwire system at RF frequencies.

Referring once again to FIG. 136, it is a novel method of the present invention that the values of the components in the LL filter do not have to be the same. That is the value of the first feedthrough capacitor 208 is desirably relatively low such as 1,000 picofarads wherein the value of the second feedthrough capacitor 208' is relatively large such as 4,000 to 5,000 picofarads. In addition as one can see the lossy ferrite inductor 200 is disposed towards the body fluid side is thicker as compared with the second lossy inductor 200'. It is desirable to have as much inductance and loss disposed towards the body fluid side in order to minimize the MRI currents that would circulate in the aforementioned loop.

A primary design methodology would be to maximize the lossy and inductive properties of the first ferrite inductor 200 and minimize the capacitance value of the first feedthrough capacitor 208. For cell phone and other high frequency attenuation, it is acceptable to have a relatively low value for the first feedthrough capacitor 208. The second feedthrough capacitor 208' would then be a much larger capacitance value and then represent a much lower impedance to ground with reference to leadwires 216 and 216'. However, the larger value feedthrough capacitor 208' is isolated behind two lossy ferrite inductors, that is ferrite inductors 200 and 200'.

Accordingly, it is a feature of the present invention that as much isolation to the capacitors be provided in order to minimize the MRI currents in the leadwire system. Minimization of MRI induced currents will mean that there is less heating along the leadwires and also less current that flows through body tissue at the sensitive TIP to RING area.

In other applications it might be desirable to have the first feedthrough capacitor 208 be of a larger value than the second feedthrough capacitor 208'. For example, in an application where MRI is not an important consideration, EMI and circuit matching considerations to the pacemaker input impedance may become paramount.

From the foregoing it will be appreciated that the novel feedthrough terminal assemblies and related processes discussed herein advantageously incorporate a lossy ferrite inductor with resistive and inductive properties that work to increase the impedance of an associated implanted leadwire system. In particular, the lossy ferrite inductor substantially raises both the inductance and resistivity of the feedthrough terminal assembly at MRI field frequencies. Further, the lossy ferrite inductor can be combined with a feedthrough filter capacitor assembly. When used in such a combination, the leadwires extend through the capacitor in conductive relation with the first set of electrode plates, and an associated ferrule, AIMD housing or ground plane is placed in conductive relation with the second set of electrode plates. Such assemblies are particularly suitable for human implantable device applications such as cardiac pacemakers, implantable defibrillators, hearing devices, neurostimulators, drug pumps, ventricular assist devices, implantable sensing systems, gastric pacemakers, prosthetic devices and the like.

Importantly, the feedthrough terminal assemblies of the present invention can be configured to form L, Pi, T, LL, or higher order low pass filter circuits, as desired.

Although several different embodiments of the present invention have been illustrated and described in detail, various modifications may be made without departing from the spirit and scope of the invention. Accordingly, the invention is not to be limited, except as by the appended claims.

What is claimed is:

1. A feedthrough terminal assembly for an active implantable medical device (AIMD), comprising:
   a plurality of leadwires extending from electronic circuitry of the AIMD; and
   a lossy ferrite inductor through which the leadwires extend in non-conductive relation for increasing the impedance of the leadwires at selected RF frequencies and reducing magnetic flux core saturation of the lossy ferrite inductor through phase cancellation of signals carried by the leadwires;
   wherein the lossy ferrite inductor is disposed on a body fluid side of the feedthrough assembly as part of an "L", "$L_2$", "T", "LL", "5 element" or "n element" low pass filter circuit.

2. The assembly of claim 1, wherein the active implantable medical device comprises a cardiac pacemaker, an implantable defibrillator, a congestive heart failure device, a hearing implant, a neurostimulator, a drug pump, a ventricular assist device, an insulin pump, a spinal cord stimulator, an implantable sensing system, an artificial heart, an incontinence device, a bone growth stimulator, a gastric pacemaker or a prosthetic device.

3. The assembly of claim 1, wherein the leadwires comprise a first leadwire extending from the electronic circuitry of the AIMD through a housing of the AIMD to a point within a human body, and a second leadwire conductively coupled to at least a portion of the AIMD housing and the AIMD circuitry.

4. The assembly of claim 1, including a conformal coating over the lossy ferrite inductor, wherein the conformal coating comprises Paralene C, D, E, or N.

5. The assembly of claim 1, including an insulator disposed between the lossy ferrite inductor and the leadwires.

6. The assembly of claim 1, including one or more additional lossy ferrite inductors through which the leadwires extend in non-conductive relation.

7. The assembly of claim 6, wherein the lossy ferrite inductors are disposed adjacent to one another.

8. The assembly of claim 7, wherein the lossy ferrite inductors are each comprised of materials having different physical or electrical properties.

9. The assembly of claim 6, including a hermetic insulator disposed between the leadwires and a ferrule, wherein the lossy ferrite inductors are disposed on opposite sides of the insulator.

10. The assembly of claim 1, including a hermetic insulator disposed between the leadwires and a ferrule, wherein the lossy ferrite inductor is bonded to the insulator to form a beam-like structure.

11. The assembly of claim 1, wherein the lossy ferrite inductor includes an aperture through which a leak detection gas can be detected.

12. The assembly of claim 1, wherein at least one of the leadwires is wound about the lossy ferrite inductor to form multiple turns, and wherein adjacent portions of the wound leadwire are electrically insulated from one another.

13. The assembly of claim 12, wherein the lossy ferrite inductor includes a notch for receiving the wound leadwire.

14. The assembly of claim 12, wherein the lossy ferrite inductor includes multiple notches therein.

15. The assembly of claim 12, wherein at least two leadwires are wound about the lossy ferrite inductor to form one or more turns, and wherein the turn count for the at least two leadwires is not equal.

16. The assembly of claim 1, including means for maintaining the lossy ferrite inductor in close association with the AIMD without laminating or bonding the inductor to another component.

17. The assembly of claim 16, wherein the maintaining means comprises a mechanical lock, a deformation in the leadwire, a cured polymer, or a wire bond pad attached to the leadwire.

18. The assembly of claim 1, wherein at least two of the leadwires are routed through the lossy ferrite inductor in opposite directions.

19. The assembly of claim 18, wherein the at least two leadwires comprise TIP and RING leadwires for the active implantable medical device.

20. The assembly of claim 1, including a cancellation antenna extending through the lossy ferrite inductor in non-conductive relation.

21. The assembly of claim 1, including a feedthrough filter capacitor having a first set of electrode plates conductively coupled to at least one of the leadwires, and a second set of electrode plates conductively coupled to a housing, ferrule or ground plane of the active implantable medical device.

22. The assembly of claim 21, wherein the assembly forms an "L", "Pi", "T", "LL", "5 element" or higher order "n element" low pass filter circuit.

23. The assembly of claim 21, wherein the lossy ferrite inductor is bonded to the capacitor to form a beam-like structure.

24. The assembly of claim 21, wherein the capacitor and the lossy ferrite inductor are at least partially housed within a ferrule.

25. The assembly of claim 24, including an insulative cap disposed over the lossy ferrite inductor opposite the capacitor.

26. The assembly of claim 21, including a second lossy ferrite inductor through which the leadwires extend in non-conductive relation, wherein the lossy ferrite inductors are disposed on opposite sides of the capacitor.

27. The assembly of claim 21 wherein the capacitor is disposed on a body fluid side of the feedthrough terminal assembly.

28. The assembly of claim 21, wherein the feedthrough capacitor comprises first and second feedthrough capacitors associated with the lossy ferrite inductor.

29. The assembly of claim 28, wherein the first and second feedthrough capacitors are disposed adjacent to opposite surfaces of the lossy ferrite inductor.

30. The assembly of claim 29, wherein at least one of the capacitors is internally grounded.

31. The assembly of claim 28, wherein the first and second capacitors each include a first set of electrode plates conductively coupled to at least one of the leadwires, and a second set of electrode plates conductively coupled to the AIMD housing, ferrule, or ground plane.

32. The assembly of claim 31, wherein the first capacitor comprises an externally grounded capacitor, and the second capacitor comprises an internally grounded capacitor, the feedthrough terminal assembly further including a conductive material extending through both the first and second feedthrough capacitors to conductively couple the second set of electrode plates of the second capacitor with the second set of electrode plates of the first capacitor.

33. The assembly of claim 28, wherein the lossy ferrite inductor comprises first and second lossy ferrite inductors arranged, with the capacitors, to form an "LL$_1$", "5 element" or "n element" low pass filter circuit, whereby the first inductor is disposed on the body fluid side of the first capacitor, and the second inductor is disposed between the first and second capacitors.

34. The assembly of claim 33, wherein the inductance of the first inductor is relatively large in comparison with the second inductor, and the capacitance of the first capacitor is relatively small in comparison with the second capacitor.

35. The assembly of claim 33, wherein the inductance of the first inductor is relatively small in comparison with the second inductor and the capacitance of the first capacitor is relatively large in comparison with the second capacitor.

36. The assembly of claim 21, wherein the capacitor's second set of electrode plates are externally grounded to and conductively coupled to the AIMD housing, ferrule or ground plane.

37. The assembly of claim 21, wherein the capacitor's second set of electrode plates are internally grounded and conductively coupled to the AIMD housing, ferrule, or ground plane.

38. The assembly of claim 1, including a wire bond pad conductively coupled to at least one of the leadwires.

39. The assembly of claim 1, wherein a surface of the inductor is configured to form a tortuous path between at least one of the leadwires and an adjacent conductor.

40. A process for filtering electromagnetic interference (EMI) in a plurality of leadwires extending from an active implantable medical device (AIMD) to different points within a human body, comprising the steps of:
    passing the leadwires through a common inductive element to increase the impedance of the leadwires at selected RF frequencies and reduce magnetic flux core saturation of the inductive element through phase cancellation of signals carried by the leadwires; and
    placing the inductive element on a body fluid side of a feedthrough assembly as part of an "L", "L$_2$", "T", "LL", "5 element" or "n element" low pass filter circuit, wherein the leadwires are subjected to occasional high power electromagnetic fields such as those produced by medical diagnostic equipment including magnetic resonance imaging, and wherein the inductive element has a diameter to thickness ratio of at least 1:1.

41. The process of claim 40, wherein the active implantable medical device comprises a cardiac pacemaker, an implantable defibrillator, a congestive heart failure device, a hearing implant, a neurostimulator, a drug pump, a ventricular assist device, an insulin pump, a spinal cord stimulator, an implantable sensing system, an artificial heart, an incontinence device, a bone growth stimulator, a gastric pacemaker, or a prosthetic device.

42. The process of claim 40, including the step of forming a tortuous path on a surface of the inductive element between at least one of the leadwires and an adjacent conductor.

43. The process of claim 40, including the step of conductively coupling a wire bond pad to at least one of the leadwires.

44. The process of claim 40, including the step of coating the inductive element with a Paralene C, D, E, or N material.

45. The process of claim 40, including the step of placing an insulator between the inductive element and at least one of the leadwires.

46. The process of claim 40, including the step of passing the leadwires through one or more additional inductive elements.

47. The process of claim 46, including the step of disposing the inductive elements adjacent to one another.

48. The process of claim 47, wherein the inductive elements are each comprised of materials having different physical or electrical properties.

49. The process of claim 46, including the step of placing a hermetic insulator between the leadwires and a ferrule such that the inductive elements are disposed on opposite sides of the insulator.

50. The process of claim 40, including the step of placing a hermetic insulator between the leadwires and a ferrule, and bonding the inductive element to the insulator to form a beam-like structure.

51. The process of claim 40, including the step of providing an aperture through the inductive element through which a leak detection gas can be detected.

52. The process of claim 40, including the step of winding at least one of the leadwires about the inductive element to form multiple turns.

53. The process of claim 40, including the step of maintaining the inductive element in close association with the AIMD without laminating or bonding the inductive element to another component.

54. The process of claim 50, including the steps of extending a first leadwire from electronic circuitry of the AIMD through a housing of the AIMD to a point within a human body, and conductively coupling a second leadwire to at least a portion of the AIMD housing and the AIMD circuitry.

55. The process of claim 40, including the step of winding the leadwires about the inductive element such that the turn count for the leadwires relative to one another is not equal.

56. The process of claim 40, including the step of routing the leadwires through the inductive element in opposite directions.

57. The process of claim 40, including the step of passing a cancellation antenna through the inductive element.

58. The process of claim 40, including the step of conductively coupling at least one of the leadwires to a first set of electrode plates of a feedthrough capacitor, and conductively coupling a second set of electrode plates of the feedthrough capacitor to a housing, ferrule or ground plane of the active implantable medical device.

59. The process of claim 58, including the step forming an "L", "Pi", "T", "LL", "5 element" or higher order "n element" low pass filter circuit.

60. The process of claim 58, including the step of bonding the capacitor to the inductive element to form a beam-like structure.

61. The process of claim 58, including the step of at least partially housing the capacitor and the inductive element within the ferrule.

62. The process of claim 61, including the step of placing an insulative cap over the inductive element opposite the capacitor.

63. The process of claim 58, including the step of passing the leadwires through a second inductive element in non-conductive relation, and disposing the inductive elements on opposite sides of the capacitor.

64. The process of claim 58, including the step of placing the capacitor on a body fluid side of a feedthrough terminal assembly.

65. The process of claim 58, including the step of associating a second feedthrough capacitor with the inductive element.

66. The process of claim 65, including the step of placing the feedthrough capacitors adjacent to opposite sides of the inductive element.

67. The process of claim 66, including the step of internally grounding at least one of the capacitors.

68. The process of claim 66, including the steps of conductively coupling at least one of the leadwires to first sets of electrode plates within the capacitors, and conductively coupling second sets of electrode plates within the capacitors to the AIMD housing, ferrule or ground plane.

69. The process of claim 68, including the steps of externally grounding one of the capacitors and internally grounding another one of the capacitors.

70. The process of claim 65, including the steps of placing a first inductive element on a body fluid side of the first capacitor, and placing a second inductive element between the first and second capacitors to form an "$LL_1$", "5 element" or "n element" low pass filter circuit.

71. The process of claim 65, wherein the inductance of the first inductive element is relatively large in comparison with the second inductive element, and the capacitance of the first capacitor is relatively small in comparison with the second capacitor, to protect the AIMD circuitry from ring-back of energy from either of the feedthrough capacitors induced by occasional high power electromagnetic fields or signals.

72. A feedthrough terminal assembly for an active implantable medical device (AIMD), comprising:
    a plurality of leadwires extending from electronic circuitry of the AIMD;
    a lossy ferrite inductor through which the leadwires extend in non-conductive relation for increasing the impedance of the leadwires at selected RF frequencies and reducing magnetic flux core saturation of the lossy ferrite inductor through phase cancellation of signals carried by the leadwires; and
    one or more additional lossy ferrite inductors through which the leadwires extend in non-conductive relation, wherein the lossy ferrite inductors are disposed adjacent to one another, and wherein the lossy ferrite inductors are each comprised of materials having different physical or electrical properties.

73. A feedthrough terminal assembly for an active implantable medical device (AIMD), comprising:
    a plurality of leadwires extending from electronic circuitry of the AIMD; and
    a lossy ferrite inductor through which the leadwires extend in non-conductive relation for increasing the impedance of the leadwires at selected RF frequencies and reducing magnetic flux core saturation of the lossy ferrite inductor through phase cancellation of signals carried by the leadwires, wherein the lossy ferrite inductor includes an aperture through which a leak detection gas can be detected.

74. A feedthrough terminal assembly for an active implantable medical device (AIMD), comprising:
    a plurality of leadwires extending from electronic circuitry of the AIMD;
    a lossy ferrite inductor through which the leadwires extend in non-conductive relation for increasing the impedance of the leadwires at selected RF frequencies and reducing magnetic flux core saturation of the lossy ferrite inductor through phase cancellation of signals carried by the leadwires; and
    a cancellation antenna extending through the lossy ferrite inductor in non-conductive relation.

75. A feedthrough terminal assembly for an active implantable medical device (AIMD), comprising:
    a plurality of leadwires extending from electronic circuitry of the AIMD;
    a lossy ferrite inductor through which the leadwires extend in non-conductive relation for increasing the impedance of the leadwires at selected RF frequencies and reducing magnetic flux core saturation of the lossy ferrite inductor through phase cancellation of signals carried by the leadwires;
    a feedthrough filter capacitor having a first set of electrode plates conductively coupled to at least one of the leadwires, and a second set of electrode plates conductively coupled to a housing, ferrule or ground plane of the active implantable medical device; and
    a second lossy ferrite inductor through which the leadwires extend in non-conductive relation, wherein the lossy ferrite inductors are disposed on opposite sides of the capacitor.

76. A feedthrough terminal assembly for an active implantable medical device (AIMD), comprising:
    a plurality of leadwires extending from electronic circuitry of the AIMD;
    a lossy ferrite inductor through which the leadwires extend in non-conductive relation for increasing the impedance of the leadwires at selected RF frequencies and reducing magnetic flux core saturation of the lossy ferrite inductor through phase cancellation of signals carried by the leadwires; and
    a feedthrough filter capacitor having a first set of electrode plates conductively coupled to at least one of the leadwires, and a second set of electrode plates conductively coupled to a housing, ferrule or ground plane of the active implantable medical device, wherein the capacitor is disposed on a body fluid side of the feedthrough terminal assembly.

77. A process for filtering electromagnetic interference (EMI) in a plurality of leadwires extending from an active implantable medical device (AIMD) to different points within a human body, comprising the steps of:
    passing the leadwires through a common inductive element to increase the impedance of the leadwires at selected RF frequencies and reduce magnetic flux core saturation of the inductive element through phase cancellation of signals carried by the leadwires;
    passing the leadwires through one or more additional inductive elements; and
    disposing the inductive elements adjacent to one another;
    wherein the inductive elements are each comprised of materials having different physical or electrical properties.

78. A process for filtering electromagnetic interference (EMI) in a plurality of leadwires extending from an active implantable medical device (AIMD) to different points within a human body, comprising the steps of:
    passing the leadwires through a common inductive element to increase the impedance of the leadwires at selected RF frequencies and reduce magnetic flux core saturation of the inductive element through phase cancellation of signals carried by the leadwires; and
    providing an aperture through the inductive element through which a leak detection gas can be detected.

79. A process for filtering electromagnetic interference (EMI) in a plurality of leadwires extending from an active implantable medical device (AIMD) to different points within a human body, comprising the steps of:

passing the leadwires through a common inductive element to increase the impedence of the leadwires at selected RF frequencies and reduce magnetic flux core saturation of the inductive element through phase cancellation of signals carried by the leadwires;

conductively coupling at least one of the leadwires to a first set of electrode plates of a feedthrough capacitor, and conductively coupling a second set of electrode plates of the feedthrough capacitor to a housing, ferrule or ground plane of the active implantable medical device;

passing the leadwires through a second inductive element in non-conductive relation; and disposing the inductive elements on opposite sides of the capacitor.

80. A process for filtering electromagnetic interference (EMI) in a plurality of leadwires extending from an active implantable medical device (AIMD) to different points within a human body, comprising the steps of:

passing the leadwires through a common inductive element to increase the impedence of the leadwires at selected RF frequencies and reduce magnetic flux core saturation of the inductive element through phase cancellation of signals carried by the leadwires;

conductively coupling at least one of the leadwires to a first set of electrode plates of a feedthrough capacitor, and conductively coupling a second set of electrode plates of the feedthrough capacitor to a housing, ferrule or ground plane of the active implantable medical device; and associating a second feedthrough capacitor with the inductive element.

* * * * *

UNITED STATES PATENT AND TRADEMARK OFFICE
CERTIFICATE OF CORRECTION

PATENT NO. : 7,765,005 B2
APPLICATION NO. : 11/097999
DATED : July 27, 2010
INVENTOR(S) : Robert A. Stevenson It is certified that error appears in the above-identified patent and that said Letters Patent is hereby corrected as shown below:

In column 46, line 30 (claim 54), replace "50" with -- 40 --.

In column 47, line 22 (claim 71), replace "65" with -- 70 --.

Signed and Sealed this
Ninth Day of August, 2011

David J. Kappos
*Director of the United States Patent and Trademark Office*